US012724033B2

(12) United States Patent
Hershberger et al.

(10) Patent No.: US 12,724,033 B2
(45) **Date of Patent: *Sep. 1, 2026**

(54) CHEMILUMINESCENT COMPOUNDS FOR MULTIPLEXING

(71) Applicant: ABBOTT LABORATORIES, Abbott Park, IL (US)

(72) Inventors: Stefan J. Hershberger, Abbott Park, IL (US); Richard A. Haack, Abbott Park, IL (US); Qiaoqiao Ruan, Abbott Park, IL (US); Quinn Best, Abbott Park, IL (US); Brian M. Bax, Abbott Park, IL (US); Kerry M. Swift, Abbott Park, IL (US); Sergey Y. Tetin, Abbott Park, IL (US)

(73) Assignee: ABBOTT LABORATORIES, Abbott Park, IL (US)

( * ) Notice: Subject to any disclaimer, the term of this patent is extended or adjusted under 35 U.S.C. 154(b) by 1162 days.

This patent is subject to a terminal disclaimer.

(21) Appl. No.: 17/633,071

(22) PCT Filed: Aug. 6, 2020

(86) PCT No.: PCT/US2020/045296

§ 371 (c)(1),
(2) Date: Feb. 4, 2022

(87) PCT Pub. No.: WO2021/026402

PCT Pub. Date: Feb. 11, 2021

(65) Prior Publication Data

US 2022/0291223 A1 Sep. 15, 2022

Related U.S. Application Data

(60) Provisional application No. 62/883,926, filed on Aug. 7, 2019.

(51) Int. Cl.

| | |
|---|---|
| ***G01N 33/58*** | (2006.01) |
| ***C09B 11/08*** | (2006.01) |
| ***C09B 15/00*** | (2006.01) |
| ***C09B 57/08*** | (2006.01) |
| ***C09K 11/07*** | (2006.01) |
| ***G01N 33/543*** | (2006.01) |

(52) U.S. Cl.

CPC ............ *G01N 33/582* (2013.01); *C09B 11/08* (2013.01); *C09B 15/00* (2013.01); *C09K 11/07* (2013.01); *G01N 33/54346* (2013.01)

(58) Field of Classification Search

CPC ......... C09B 11/08; C09B 11/22; C09B 11/24; C09B 11/28; C09B 15/00; C09B 19/00; C09B 23/04; C09B 23/06; C09B 57/08; C09B 57/10; C09K 11/07; G01N 33/54346; G01N 33/582

See application file for complete search history.

(56) References Cited

U.S. PATENT DOCUMENTS

| | | | | |
|---|---|---|---|---|
| 4,510,251 | A | | 4/1985 | Kirkemo et al. |
| 5,006,309 | A | | 4/1991 | Khalil et al. |
| 5,063,081 | A | | 11/1991 | Cozzette et al. |
| 5,089,424 | A | | 2/1992 | Khalil et al. |
| 5,270,163 | A | | 12/1993 | Gold et al. |
| 5,294,404 | A | | 3/1994 | Grandone et al. |
| 5,468,646 | A | | 11/1995 | Mattingly et al. |
| 5,475,096 | A | | 12/1995 | Gold et al. |
| 5,567,588 | A | | 10/1996 | Gold et al. |
| 5,595,877 | A | | 1/1997 | Gold et al. |
| 5,620,850 | A | | 4/1997 | Bamdad et al. |
| 5,637,459 | A | | 6/1997 | Burke et al. |
| 5,683,867 | A | | 11/1997 | Biesecker et al. |
| 5,705,337 | A | | 1/1998 | Gold et al. |
| 6,156,800 | A | | 12/2000 | Weichert et al. |
| 6,165,800 | A | * | 12/2000 | Jiang .................... G01N 33/542 546/37 |
| 7,070,921 | B2 | | 7/2006 | Huang et al. |
| 8,287,808 | B2 | | 10/2012 | Krupenkin et al. |
| 8,445,199 | B2 | | 5/2013 | Collier et al. |
| 9,157,910 | B2 | | 10/2015 | Dowell et al. |
| 9,207,246 | B2 | | 12/2015 | Collier et al. |
| 9,239,284 | B2 | | 1/2016 | Livingston |
| 9,964,537 | B2 | | 5/2018 | Collier et al. |
| 2003/0170881 | A1 | | 9/2003 | Davis et al. |
| 2004/0018577 | A1 | | 1/2004 | Emerson Campbell et al. |
| 2004/0038294 | A1 | | 2/2004 | Evangelista et al. |
| 2005/0054078 | A1 | | 3/2005 | Miller et al. |

(Continued)

FOREIGN PATENT DOCUMENTS

| | | |
|---|---|---|
| EP | 1403254 | 3/2004 |
| WO | WO 98/54574 | 12/1998 |

(Continued)

OTHER PUBLICATIONS

Adamczyk et al., Chemiluminescence quenching of pteroic acid-N-sulfonyl-acridinium-9-carboxamide conjugates by folate binding protein. Bioorg Med Chem Lett. May 3, 2004;14(9):2313-7.
Adamczyk et al., Chemiluminescent acridinium-9-carboxamide boronic acid probes: application to a homogeneous glycated hemoglobin assay. Bioorg Med Chem Lett. Mar. 1, 2006;16(5):1324-8.
Adamczyk et al., Immunoassay reagents for thyroid testing. 2. Binding properties and energetic parameters of a T4 monoclonal antibody and its Fab fragment with a library of thyroxine analog biosensors using surface plasmon resonance. Bioconjug Chem. Mar.-Apr. 1997;8(2):133-45.
Adamczyk et al., Intrinsic factor-mediated modulation of cyanocobalamin-N-sulfonyl-acridinium-9-carboxamide chemiluminescence. Bioorg Med Chem Lett. Aug. 2, 2004;14(15):3917-21.
Adamczyk et al., Neopentyl 3-Triflyloxypropanesulfonate. A Reactive Sulfopropylation Reagent for the Preparation of Chemiluminescent Labels. J. Org. Chem. 1998, 63(16), 5636-5639.

(Continued)

*Primary Examiner* — Shafiqul Haq
*Assistant Examiner* — Nam P Nguyen
(74) *Attorney, Agent, or Firm* — Lisa Mueller; Tristan A. Fuierer; Casimir Jones SC

(57) ABSTRACT

Disclosed herein are compounds, conjugates, and methods that may be used to detect the presence of an analyte in a sample, such as a biological sample.

19 Claims, 9 Drawing Sheets

(56) References Cited

U.S. PATENT DOCUMENTS

2006/0121544 A1 6/2006 Boge et al.
2006/0160164 A1 7/2006 Miller et al.
2014/0273035 A1 9/2014 Dowell et al.
2015/0330986 A1 11/2015 Grote
2017/0153248 A1 6/2017 Goix et al.
2018/0017552 A1 1/2018 Duffy et al.
2022/0276256 A1* 9/2022 Pope .................... G01N 33/582

FOREIGN PATENT DOCUMENTS

WO WO 2007/136386 11/2007
WO WO 2009/111431 9/2009
WO WO 2010/040227 4/2010
WO WO 2011/137533 11/2011
WO WO 2013/066441 5/2013
WO WO 2014/062551 4/2014
WO WO 2014/066704 5/2014
WO WO 2016/161400 10/2016
WO WO 2016/161402 10/2016

OTHER PUBLICATIONS

Adamczyk et al., Regiodependent luminescence quenching of biotinylated N-sulfonyl-acridinium-9-carboxamides by avidin. Org Lett. Oct. 16, 2003;5(21):3779-82.
Bag et al., A BODIPY-luminol chemiluminescent resonance energy-transfer (CRET) cassette for imaging of cellular superoxide. Org Biomol Chem. Feb. 14, 2015;13(6):1763-7.
Bouvet et al., Polyreactivity is not an artefact. J Immunol Methods. Aug. 1, 2001;254(1-2):199-201.
Browne et al., Spectrally resolved chemiluminescent probes for sensitive multiplex molecular quantification. Anal Chem. Nov. 6, 2012;84(21):9222-9.
Cai et al., Introduction of functional groups into polymer films via deep-UV photolysis or electron-beam lithography: modification of polystyrene and poly(3-octylthiophene) by a functionalized perfluorophenyl azide. Chem. Mater. 1992, 4(4), 879-884.
Casesnoves et al., Influence of anti-insulin antibodies on insulin immunoassays in the autoimmune insulin syndrome. Ann Clin Biochem. Nov. 1998;35 ( Pt 6):768-74.
Demers et al., E. Thyroglobulin (Tg) Measurement. Thyroid, 2003; 13: 57-67.
Despres et al., Antibody interference in thyroid assays: a potential for clinical misinformation. Clin Chem. Mar. 1998;44(3):440-54.
Dexter. A Theory of Sensitized Luminescence in Solids. J. Chem. Phys. 1953, 21, 836-850.
Dodeigne et al., Chemiluminescence as diagnostic tool. A review. Talanta. Mar. 6, 2000;51(3):415-39.
Dong et al., Sulfur(VI) fluoride exchange (SuFEx): another good reaction for click chemistry. Angew Chem Int Ed Engl. Sep. 1, 2014;53(36):9430-48.
Fahie-Wilson et al., Hyperprolactinaemia due to macroprolactins: some progress but still a problem. Clin Endocrinol (Oxf). Jun. 2003;58(6):683-5.
Faulkner et al., Mechanisms of chemiluminescent electron-transfer reactions. I. Role of the triplet state in energy-deficient systems. J. Am. Chem. Soc. 1971, 93(9), 2097-2102.
Feldt-Rasmussen et al., Serum thyroglobulin (Tg) in presence of thyroglobulin autoantibodies (TgAb). Clinical and methodological relevance of the interaction between Tg and TgAb in vitro and in vivo. J Endocrinol Invest. Dec. 1985;8(6):571-6.
Fischer et al., Direct Transformation of Esters into Heterocyclic Fluorophores. Angew Chem Int Ed Engl. Feb. 23, 2018;57(9):2436-2440.
Glezer et al., Pitfalls in pituitary diagnosis: peculiarities of three cases. Clin Endocrinol (Oxf). Jul. 2002;57(1):135-9.
Gottlin et al., Isolation of novel EGFR-specific VHH domains. J Biomol Screen. Jan. 2009;14(1):77-85.
Haack et al., Chemoselective reaction of bifunctional carboxysulfonic acid systems: Preparation of useful intermediates for chemiluminescent, fluorescent and UV absorbing bifunctional linkers. Tetrahedron Letters, 2020, vol. 61, No. 40. 8 pages.
Haugen et al., 2015 American Thyroid Association Management Guidelines for Adult Patients with Thyroid Nodules and Differentiated Thyroid Cancer: The American Thyroid Association Guidelines Task Force on Thyroid Nodules and Differentiated Thyroid Cancer. Thyroid. Jan. 2016;26(1):1-133.
Haugland, The Handbook of Fluorescent Probes and Research Chemicals, Publisher, Molecular Probes, Inc., Eugene, Oreg. Jun. 1992. TOC only. 4 pages.
Heller. Electrical wiring of redox enzymes. Acc. Chem. Res. 1990. 23(5), 128-134.
Hiblot et al., Luciferases with Tunable Emission Wavelengths. Angew Chem Int Ed Engl. Nov. 13, 2017;56(46):14556-14560.
Hjiyiannakis et al., Thyroglobulin antibodies in differentiated thyroid cancer. Clin Oncol (R Coll Radiol). 1999;11(4):240-4.
Huang et al., Digital Microfluidic Dynamic Culture of Mammalian Embryos on an Electrowetting on Dielectric (EWOD) Chip. PLoS One. May 1, 2015;10(5):e0124196. 15 pages.
Huang et al., Gold nanoparticles based chemiluminescent resonance energy transfer for immunoassay of alpha fetoprotein cancer marker. Anal Chim Acta. Feb. 7, 2011;686(1-2):115-20.
International Preliminary Report on Patentability for PCT/US2020/045296. Mailed Feb. 17, 2022. 8 pages.
International Search Report and Written Opinion for PCT/US2020/045296. Mailed Dec. 3, 2020. 13 pages.
International Search Report and Written Opinion for PCT/US2020/045297. Mailed Oct. 15, 2020. 14 pages.
KRICKA. Human anti-animal antibody interferences in immunological assays. Clin Chem. Jul. 1999;45(7):942-56.
Kuwahara et al., Autoantibody against testosterone in a woman with hypergonadotropic hypogonadism. J Clin Endocrinol Metab. Jan. 1998;83(1):14-6.
Levinson et al., Towards a better understanding of heterophile (and the like) antibody interference with modern immunoassays. Clin Chim Acta. Nov. 2002;325(1-2):1-15.
Lippi et al., Macroprolactin: searching for a needle in a haystack? Clin Chem Lab Med. Apr. 2016;54(4):519-22.
Liu et al., Proximity hybridization-regulated chemiluminescence resonance energy transfer for homogeneous immunoassay. Talanta. Jul. 1, 2016;154:455-60.
Marquette et al., Recent advances in multiplex immunoassays. Bioanalysis. May 2012;4(8):927-36.
Masters et al., Investigation of sex-hormone binding globulin interference in direct radioimmunoassays for testosterone and estradiol. Clin Chem. Jun. 1989;35(6):979-84.
Mattingly et al., Preparation of 5- and 6-(aminomethyl)fluorescein. Bioconjug Chem. Sep.-Oct. 1992;3(5):430-1.
Natrajan et al., A comparison of chemiluminescent acridinium dimethylphenyl ester labels with different conjugation sites. Org Biomol Chem. Mar. 7, 2015;13(9):2622-33.
Nealson et al., Bacterial bioluminescence: its control and ecological significance. Microbiol Rev. Dec. 1979;43(4):496-518.
Nishioka et al., New luminescent europium(III) chelates for DNA labeling. Inorg Chem. May 15, 2006;45(10):4088-96.
Ohashi et al., "Paradoxical" GH suppression by secretagogues in acromegaly? Horm Metab Res. Jul. 1993;25(7):393-4.
Oliner, A.A.(ed), Acoustic Surface Waves. Springer. 1978. TOC only. 8 pages.
Peng et al., EWOD (electrowetting on dielectric) digital microfluidics powered by finger actuation. Lab Chip. Mar. 21, 2014;14(6):1117-22.
Perros et al., Guidelines for the management of thyroid cancer. Clin Endocrinol (Oxf). Jul. 2014;81 Suppl 1:1-122.
Phillips et al., Energy transfer from chemiluminescent species in polymers. Nature. Sep. 9, 1967;215(5106):1163-5.
Preliminary Report on Patentability for PCT/US2020/045297. Mailed Feb. 17, 2022. 8 pages.
Rauhut. Chemiluminescence from concerted peroxide decomposition reactions. Acc. Chem. Res. 1969, 2(3), 80-87.

(56) References Cited

OTHER PUBLICATIONS

Ryall et al., Reappraisal of the causes of the "hook effect" in two-site immunoradiometric assays. Anal Biochem. Dec. 1982;127(2):308-15.
Sakata et al., Autoantibodies against thyroid hormones or iodothyronine. Implications in diagnosis, thyroid function, treatment, and pathogenesis. Ann Intern Med. Oct. 1985;103(4):579-89.
Sapin. Anti-insulin antibodies in insulin immunometric assays: a still possible pitfall. Eur J Clin Chem Clin Biochem. May 1997;35(5):365-7.
Schaadt et al., Assessment of the influence of thyroglobulin (Tg) autoantibodies and other interfering factors on the use of serum Tg as tumor marker in differentiated thyroid carcinoma. Thyroid. Jun. 1995;5(3):165-70.
Schneckenburger. Fluorescence Techniques in Biomedical Diagnostics: Instrumentation, Analysis and Unresolved Issues. Springer Ser Fluoresc. 2008, 6, 533-548.
Seliger et al., Stereo-specificity and firefly bioluminescence, a comparison of natural and synthetic luciferins. Proc Natl Acad Sci U S A. Aug. 1961;47(8):1129-34.
Shieh et al., Fluorogenic azidofluoresceins for biological imaging. J Am Chem Soc. Oct. 24, 2012;134(42):17428-31.
Sklenarova et al. Quantum dots as chemiluminescence enhancers tested by sequential injection technique: Comparison of flow and flow-batch conditions. J. Lumin. 2017, 184, 235-241.
Slaats et al., Interference of sex-hormone binding globulin in the "Coat-A-Count" testosterone no-extraction radioimmunoassay. Clin Chem. Feb. 1987;33(2 Pt 1):300-2.
Spindel et al., In vitro FRET sensing, diagnostics, and personalized medicine. Förster Resonance Energy Transfer—From Theory to Applications 2013, 271-322.
St-Jean et al., High prolactin levels may be missed by immunoradiometric assay in patients with macroprolactinomas. Clin Endocrinol (Oxf). Mar. 1996;44(3):305-9.
Sturgeon et al., Analysis of hCG: clinical applications and assay requirements. Ann Clin Biochem. Jul. 1998;35 ( Pt 4):460-91.
Suliman et al., Frequent misdiagnosis and mismanagement of hyperprolactinemic patients before the introduction of macroprolactin screening: application of a new strict laboratory definition of macroprolactinemia. Clin Chem. Sep. 2003;49(9):1504-9.
Symons. Interference with the Laboratory Assessment of Thyroid Funciton. Clin Biochem Rev., 1989; 10: 44-49.
Tate et al., Interferences in immunoassay. Clin Biochem Rev. May 2004;25(2):105-20.
Tseng et al., In vivo imaging of endogenous enzyme activities using luminescent 1,2-dioxetane compounds. J Biomed Sci. Jun. 24, 2015;22(1):45. 11 pages.
Turro et al., Modern Molecular Photochemistry of Organic Molecules. University Science Books, Mill Valley, California, 2010. TOC only. 25 pages.
Vaishya et al., Macroprolactin; a frequent cause of misdiagnosed hyperprolactinemia in clinical practice. J Reprod Infertil. Oct. 2010;11(3):161-7.
Vedejs et al., Reactive triflate alkylating agents. J. Org Chem., 1977, 42(19), 3109-3113.
Vining. Steroid Radioimmunoassay. Clin. Biochem. Rev., 1981; 2: 39-49.
Wingert et al., Enhanced chemiluminescent resonance energy transfer in hollow calcium phosphate nanoreactors and the detection of hydrogen peroxide. Nanotechnology, 2007, 18, 295707-295713.
Yigitbasi. Multiplex immunoassay and bead based multiplex. Trends in Immunolabelled and Related Techniques, 2012, 351-360.
Zhao et al., A nonenzymatic chemiluminescent reaction enabling chemiluminescence resonance energy transfer to quantum dots. Chemistry. Jun. 1, 2010;16(21):6142-5.

* cited by examiner

CPSP Acr

Example 56
Acr-CP-Fl(5 / 6)

Example 55
Acr-CP-Fl(4)

| Emission Wavelenght | 400-500 nm Region | 500-800 nm Region |
|---|---|---|
| Acr | 95% | 5% |
| Acr-CP-Fl(5 / 6) | 95% | 5% |
| Acr-CP-Fl(4) | 94% | 6% |

Example 12
Acr–Pip–Fl(5 / 6)

Example 13
Acr–EDA–Fl(5 / 6)

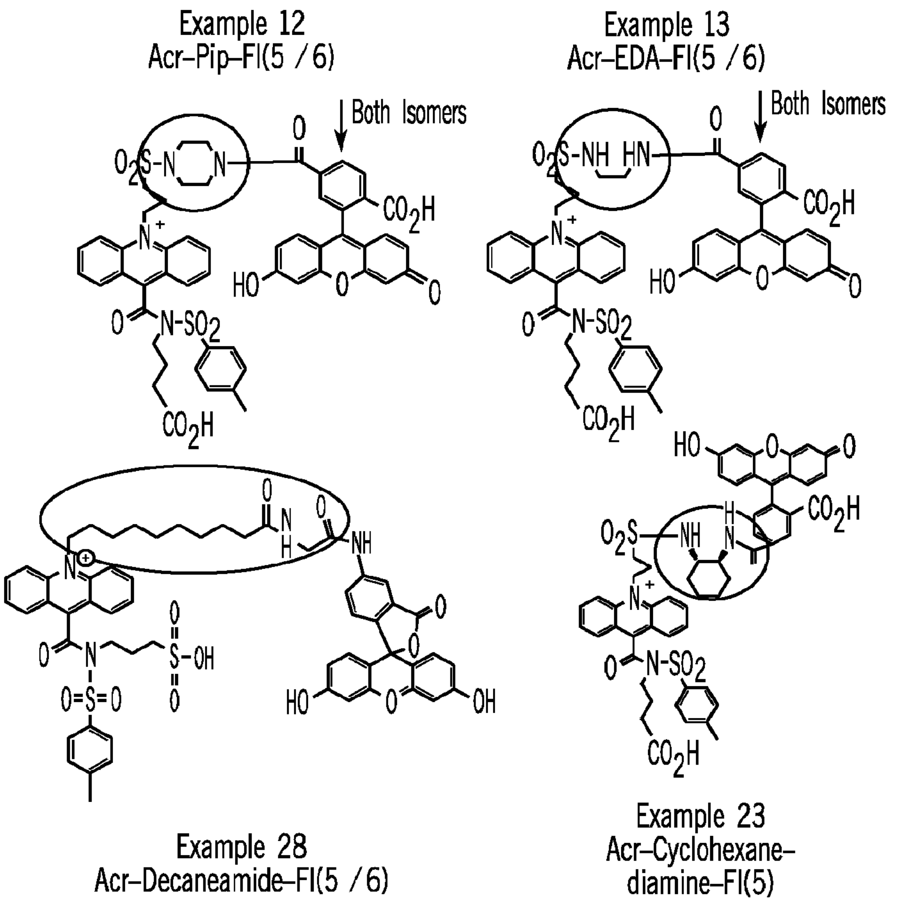

Example 28
Acr–Decaneamide–Fl(5 / 6)

Example 23
Acr–Cyclohexane–diamine–Fl(5)

| | Emission 440 nm Region | Emission 530 nm Region | Realitve Intensity |
|---|---|---|---|
| Acr–Pip–Fl(5 / 6) | 1% | 99% | 87% |
| Acr–EDA–Fl(5 / 6) | 1% | 99% | 40% |
| Acr–Deacaneamide–Fl(5 / 6) | 1% | 99% | n.d. |
| Acr–Cyclohexane–diamine–Fl(5) | 2% | 98% | n.d. |

n.d. = not determined
Relative intensity to CPSP acridinium at a similar concentration as measured using a Berthold Mithras LB940 microplate luminometer.

FIGURE 5

CHEMILUMINESCENT COMPOUNDS FOR MULTIPLEXING

CROSS-REFERENCE TO RELATED APPLICATION

This application claims the benefit of U.S. Provisional Patent Application No. 62/883,926, filed Aug. 7, 2019, which is incorporated by reference herein.

BACKGROUND

The ability to multiplex, measure two or more analytes from one sample in a single test, is highly sought after within the in vitro diagnostic market. Multiplex tests allow greater throughput, reduced time per result, and fewer consumables. The potential also exists to reduce internal costs and improve overall margin. One method to differentiate multiple signals in one test is via reporter molecule emission wavelength. To achieve a wavelength shift using chemiluminescence, triggerable chemiluminescent compounds with red-shifted emission wavelength are desired.

BRIEF SUMMARY OF THE INVENTION

The disclosure provides compound of formula (I), or a salt thereof:

(I)

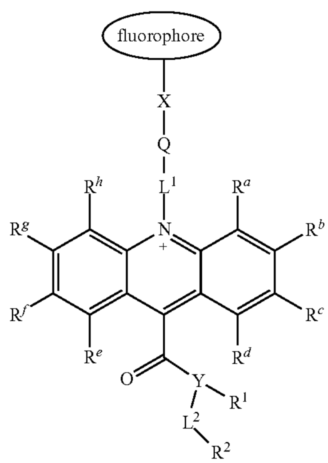

wherein: X is —NH— or a diamine linker; Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; when Y is oxygen or sulfur, $R^1$ is absent; Q is —$SO_2$— or —CO—; $L^1$ and $L^2$ are each independently selected from alkylene and heteroalkylene; $R^2$ is selected from —COOZ and —CN; Z is selected from hydrogen, alkyl, alkenyl, alkynyl, aryl, heteroaryl, cycloalkyl, heterocyclyl, arylalkyl, heteroarylalkyl, cycloalkylalkyl, heterocyclylalkyl, aryloxy, and heteroalkyl; and $R^a$, $R^b$, $R^c$, $R^d$, $R^e$, $R^f$, $R^g$, and $R^h$ are each independently selected from hydrogen, $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; wherein each alkyl, alkenyl, alkynyl, aryl, heteroaryl, cycloalkyl, heterocyclyl, arylalkyl, heteroarylalkyl, cycloalkylalkyl, heterocyclylalkyl, aryloxy, heteroalkyl, alkylene, and heteroalkylene is independently optionally substituted with 1, 2, 3, 4, or 5 substituents.

The disclosure also provides a conjugate of formula (II), or a salt thereof:

(II)

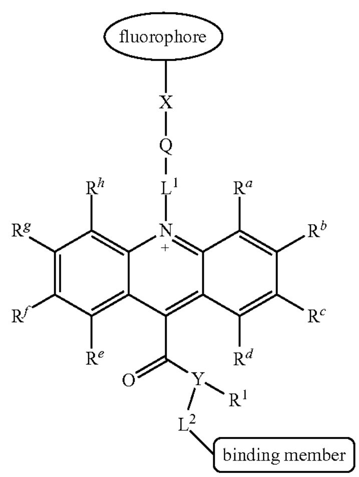

wherein: X is —NH— or a diamine linker; Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; when Y is oxygen or sulfur, $R^1$ is absent; Q is —$SO_2$— or —CO—; $L^1$ is selected from alkylene and heteroalkylene; $L^3$ is a linker; $R^a$, $R^b$, $R^c$, $R^d$, $R^e$, $R^f$, $R^g$ and $R^h$ are each independently selected from hydrogen, $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; and the binding member is a molecule capable of binding to a target analyte; wherein each alkyl, alkenyl, alkynyl, aryl, heteroaryl, cycloalkyl, heterocyclyl, arylalkyl, heteroarylalkyl, cycloalkylalkyl, heterocyclylalkyl, alkylene, and heteroalkylene is independently optionally substituted with 1, 2, 3, 4, or 5 substituents.

The disclosure further provides methods of detecting two or more analytes in a biological sample using the aforementioned conjugates.

BRIEF DESCRIPTION OF THE DRAWINGS

FIG. 5 shows structures and emission data for compounds in which a fluorophore is attached to a substituted acridinium moiety via various linkers.

DETAILED DESCRIPTION

Figure 1:
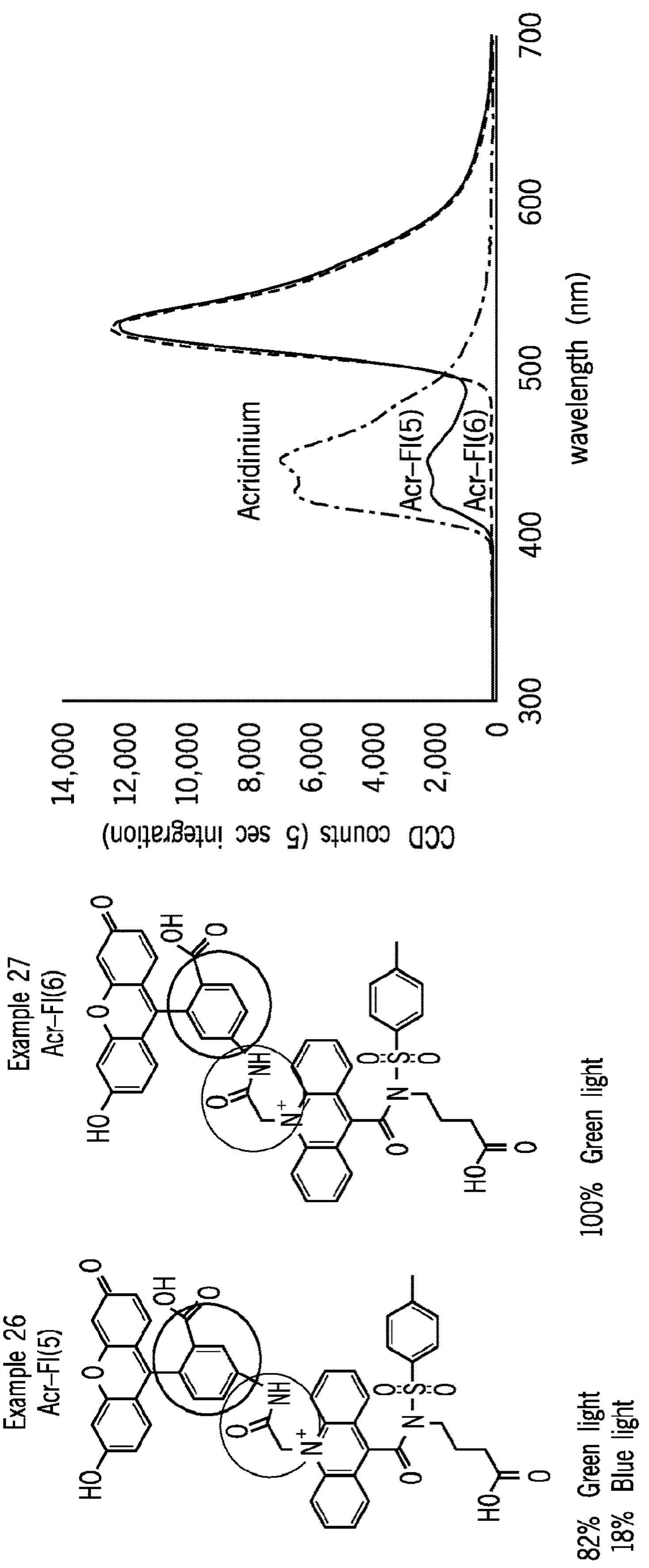
FIG. 1 shows structures and fluorescence data for 5- and 6-isomers of fluorescein attached to a substituted acridinium moiety via an acetamide linker.
Figure 2:
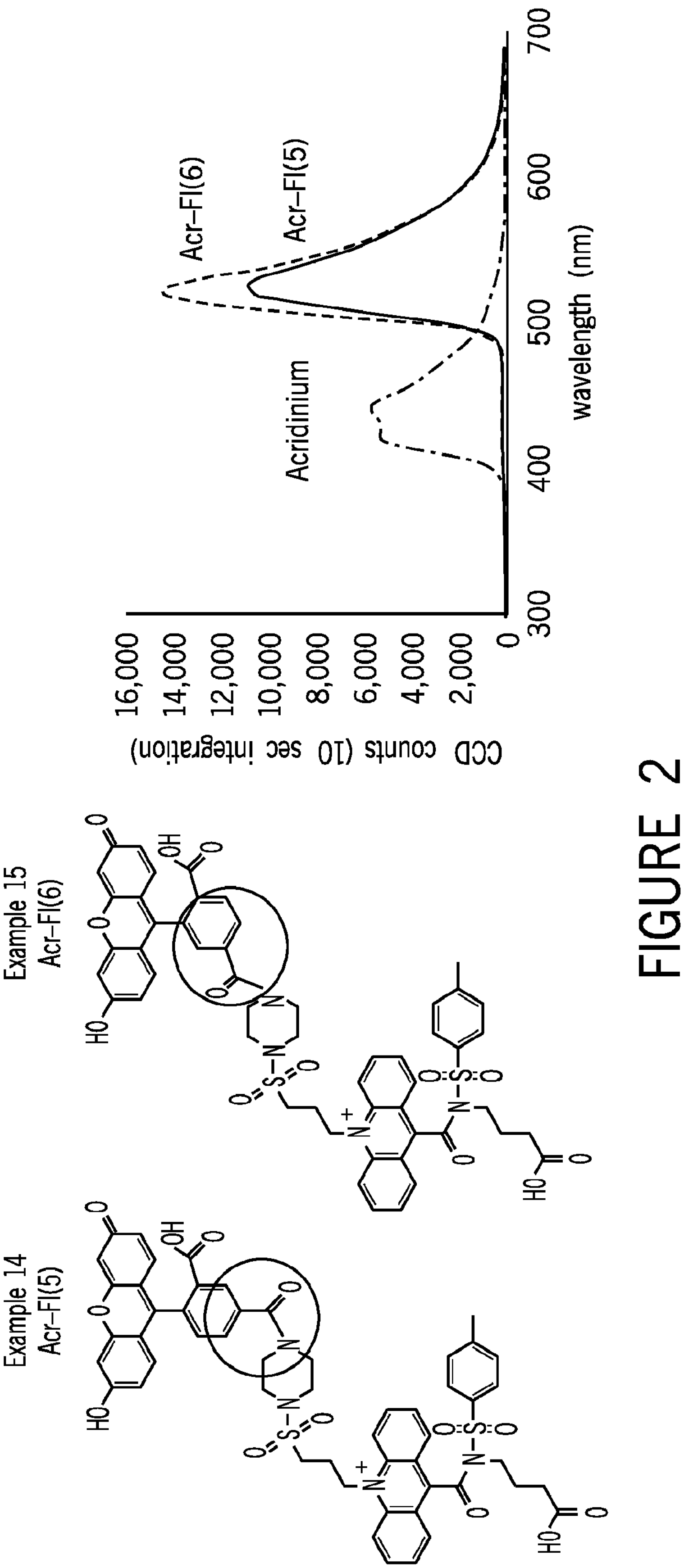
FIG. 2. shows structures and fluorescence data for 5- and 6-isomers of fluorescein attached to a substituted acridinium moiety via a piperazine linker.

Disclosed herein are compounds, conjugates, and methods that may be used to detect the presence of an analyte in a sample, such as a biological sample. The compounds include an acridinium moiety and a fluorophore that are linked via a rigid diamine linker. Upon chemiluminescent triggering of the acridinium moiety, light output can be shifted to the emission wavelength of the attached fluorophore. The compounds can be conjugated to a molecule capable of specific binding to an analyte of interest in a sample, such that the presence or absence of the analyte can be determined. Use of multiple conjugates in a single assay, having different fluorophores, may allow for detection of two or more analytes from one sample in a single test, which may be particularly useful for in vitro diagnostics.

Chemiluminescence has been studied extensively since the middle of the 20th century. Enzyme induced chemiluminescence, bioluminescence, peroxyoxylate chemistry, and acridinium chemistry are examples of chemiluminescent systems each defined by the ability to produce light through a chemical reaction. Chemiluminescence and bioluminescence research has led to a myriad of publications and patents and a better understanding of fireflies and angler fish (via bioluminescent bacteria) as well as commercial products such as glowsticks and immunoassays (Seliger et al. *Proc. Natl. Acad. Sci. USA,* 1961, 47, 1129-1134; Nealson et al. *Microbiol. Rev.* 1979, 43(4), 496-518; Rauhut, *Acc. Chem. Res.* 1969, 2(3), 80-87; Dodeigne et al. *Talanta* 2000, 51, 415-439). The mechanism of chemiluminescent emission varies per chemiluminescent system, but all theories result in an excited state molecule which relaxes to ground state while emitting a photon. The properties of the excited state molecule dictate the emission wavelength of the emitted photon.

The ability to tune the emission wavelength of chemiluminescent species is valuable for several applications including immunoassay multiplexing. A classic example of tunable emission wavelength chemiluminescence is glowsticks in which luminophores of various emission wavelengths can be used to produce a broad spectrum of glowstick colors in an intermolecular process. By careful selection of the molecule capable of becoming excited, one can select the wavelength of emission for chemiluminescent systems. Shifted emission may be achieved through chemiluminescent energy or electron transfer processes. These processes have been shown to function both intermolecularly and intramolecularly via various hypothesized mechanisms including permutations of Forster resonance energy transfer (FRET), Dexter electron transfer, chemiluminescent energy transfer (CRET), and chemically initiated electron exchange luminescence (CIEEL). Examples of such intramolecular systems include BRET based systems employing fluorophore tagged luciferase enzymes (Hiblot et al. *Angew. Chem. Int. Ed.* 2017, 56, 14556-14560), adamantyl dioxetane fluorophore constructs (Tseng et al. *J. Biomed. Sci.* 2015, 22 (1), 4), acridinium labeled quantum dots (Sklenarova et al. *J. Lumin.* 2017, 184, 235-241), and acridinium-labeled DNA systems (Browne et al. *Anal. Chem.* 2012, 84, 9222-9229). It may be possible to exploit the phenomenon of energy or electron transfer using acridinium as a chemical initiator and an intramolecularly linked fluorophore energy acceptor to produce an emission wavelength which is shifted from that of acridinium/acridone chemiluminescent emission.

Chemiluminescent energy/electron transfer has been studied since the mid-1960s with varying hypotheses as to the mechanism leading to shifted emission (Phillips et al. *Nature,* 1967, 215, 1163-1165; Freed et al. *J. Am. Chem. Soc.* 1971, 93(9), 2097-2102; U.S. Pat. No. 6,156,800). The dominating notion in acridinium initiated electron/energy transfer is that the length of the moiety linking the initiator (i.e. acridinium) to the acceptor (i.e. fluorophore) is the driving factor controlling shifted emission. However, without wishing to be limited by theory, the present inventors have compiled evidence that initiator (acridinium) to acceptor (fluorophore/luminophore) orientation relative to each other may be a key driving factor in shifted emission efficiency. Compounds shown herein, having a rigid diamine linker between the acridinium moiety and the fluorophore, can achieve 100% shifted emission, that is the shifted emission light output is 100% of that expected from acridinium alone with little to no observed light in the lower emission band for optimized systems. The requirement for orbital alignment and the observation of 100% shifted emission lends to the Dexter mechanism of electron transfer (Turro et al. Modern Molecular Photochemistry of Organic Molecules. University Science Books, Mill Valley, California, 2010; Dexter, *J. Chem. Phys.* 1953, 21, 836). Relative linker length does appear to play a role in the context that distance can drive apart proper orientation or allow greater degrees of freedom which limit the percentage of molecules in which fluorophore and initiator reside in the proper orientation to facilitate transfer. However, linker length can be viewed independently of orientation as longer linkers can fold/bend to produce the correct orientation while shorter linkers may hold the two moieties in an unfavorable orientation. Therefore, linker length itself does not drive shifted emission. In addition, linker type, fluorophore attachment point, and initiator attachment point may each impact moiety orientation and therefore may be important factors in preparing shifted-emission chemiluminescent compounds.

Definitions

"Comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Sorrell, Organic Chemistry, 2nd edition, University Science Books, Sausalito, 2006; Smith, March's Advanced Organic Chemistry: Reactions, Mechanism, and Structure, 7th Edition, John Wiley & Sons, Inc., New York, 2013; Larock, Comprehensive Organic Transformations, 3rd Edition, John Wiley & Sons, Inc., New York, 2018; Carruthers, Some Modern Methods of Organic Synthesis, 3rd Edition, Cambridge University Press, Cambridge, 1987; the entire contents of each of which are incorporated herein by reference.

The term "alkyl," as used herein, means a straight or branched saturated hydrocarbon chain containing from 1 to 16 carbon atoms ($C_1$-$C_{16}$ alkyl), for example 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$alkyl), 1 to 6 carbon atoms ($C_1$-$C_6$ alkyl), or 1 to 4 carbon atoms ($C_1$-$C_4$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

The term "alkenyl," as used herein, refers to a straight or branched hydrocarbon chain containing from 2 to 16 carbon atoms and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl," as used herein, refers to a straight or branched hydrocarbon chain containing from 2 to 16 carbon atoms and containing at least one carbon-carbon triple bond. Representative examples of alkynyl include, but are not limited to, ethynyl, propynyl, and butynyl.

The term "alkylene," as used herein, refers to a divalent group derived from a straight or branched chain hydrocarbon of 1 to 10 carbon atoms ($C_1$-$C_{10}$ alkylene), for example, of 1 to 6 carbon atoms ($C_1$-$C_6$ alkylene). Representative examples of alkylene include, but are not limited to, $—CH_2—$, $—CH_2CH_2—$, $—CH(CH_3)—$, $—CH_2CH_2CH_2—$, $—CH_2CH(CH_3)—$, $—CH_2CH_2CH_2CH_2—$, $—CH_2CH(CH_3)CH_2—$, $—CH_2CH_2CH(CH_3)—$, $—CH_2CH_2CH_2CH_2CH_2—$, $—CH_2CH(CH_3)CH_2CH_2—$, $—CH(CH_3)CH_2CH_2CH_2—$, $—CH_2CH_2CH_2CH_2CH_2CH_2—$, $—CH_2CH_2CH(CH_3)CH_2CH_2—$, $—CH_2CH(CH_3)CH_2CH_2CH_2—$, and $—CH(CH_3)CH_2CH_2CH_2CH_2—$.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "aryl," as used herein, refers to a phenyl group, or a bicyclic or tricyclic aromatic fused ring system. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl and phenanthreneyl.

The term "arylalkyl," as used herein, refers to an aryl group, as defined herein, appended to the parent molecular moiety through an alkyl group, as defined herein. Representative examples of arylalkyl include, but are not limited to, phenylmethyl (i.e. benzyl) and phenylethyl.

The term "aryloxy," as used herein, means an aryl group, as defined herein, appended to the parent molecular moiety through an oxygen atom.

The term "cycloalkyl," as used herein, refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[1.1.1]pentanyl, bicyclo[2.2.1]heptanyl, bicyclo[3.2.1]octanyl, and bicyclo[5.2.0]nonanyl.

The term "cycloalkenyl," as used herein, means a non-aromatic monocyclic or multicyclic carbocyclic ring system containing at least one carbon-carbon double bond and preferably having from 5-10 carbon atoms per ring. Exemplary monocyclic cycloalkenyl rings include, but are not limited to, cyclopentenyl, cyclohexenyl, cycloheptenyl, and bicyclo[2.2.1]heptenyl.

As used herein, the term "cycloalkylalkyl" refers to a cycloalkyl group, as defined herein, appended to the parent molecular moiety through an alkylene group, as defined herein. Representative examples of cycloalkylalkyl include, but are not limited to, cyclohexylmethyl.

The term "diamine linker," as used herein, refers to a linker moiety having an amine functional group (—NH— or —NR—) at each end. The diamine linker may be linear, branched, or cyclic.

The term "halogen" or "halo," as used herein, means F, Cl, Br, or I.

The term "haloalkyl," as used herein, means an alkyl group, as defined herein, in which one or more hydrogen atoms are replaced by a halogen. For example, one, two, three, four, five, six, seven or eight hydrogen atoms can be replaced by a halogen, or all hydrogen atoms can be replaced by a halogen. Representative examples of haloalkyl include, but are not limited to, fluoromethyl, difluoromethyl, trifluoromethyl, chloromethyl, dichloromethyl, trichloromethyl, 2-fluoroethyl, 2,2-difluoroethyl, 2,2,2-trifluoroethyl, perfluoroethyl, 2-fluoro-2-methylpropyl, and 3,3,3-trifluoropropyl.

The term "haloalkoxy," as used herein, means at least one haloalkyl group, as defined herein, is appended to the parent molecular moiety through an oxygen atom. Representative examples of haloalkoxy include, but are not limited to, trifluoromethoxy.

The term "heteroalkyl," as used herein, refers to an alkyl group, as defined herein, in which at least one carbon atom has been replaced with a heteroatom such as N, O, P, or S.

Representative examples of heteroalkyls include, but are not limited to, alkyl ethers, secondary and tertiary alkyl amines, amides, and alkyl sulfides.

The term "heteroalkylene," as used herein, refers to an alkylene group, as defined herein, in which at least one carbon atom has been replaced with a heteroatom such as N, O, P, or S. Representative examples of heteroalkylene groups include polyethylene oxide and polypropylene oxide chains, polyethyleneimine groups, and the like.

The term "heteroaryl," as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O, and S (e.g. 1, 2, 3, or 4 heteroatoms independently selected from O, S, and N). The five-membered aromatic monocyclic rings have two double bonds and the six membered six membered aromatic monocyclic rings have three double bonds. The bicyclic heteroaryl groups are exemplified by a monocyclic heteroaryl ring appended fused to a monocyclic aryl group, as defined herein, or a monocyclic heteroaryl group, as defined herein. The tricyclic heteroaryl groups are exemplified by a monocyclic heteroaryl ring fused to two rings independently selected from a monocyclic aryl group, as defined herein or a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, chromenyl, imidazopyridine, imidazothiazolyl, indazolyl, indolyl, isobenzofuranyl, isoindolyl, isoquinolinyl, naphthyridinyl, purinyl, pyridoimidazolyl, quinazolinyl, quinolinyl, quinoxalinyl, thiazolopyridinyl, thiazolopyrimidinyl, thienopyrrolyl, and thienothienyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

The term "heteroarylalkyl," as used herein, refers to a heteroaryl group, as defined herein, appended to the parent molecular moiety through an alkylene group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocycles are connected to the parent molecular moiety through any carbon atom or any nitrogen atom contained within the rings.

As used herein, the term "heterocyclylalkyl" refers to a heterocyclyl group, as defined herein, appended to the parent molecular moiety through an alkylene group, as defined herein. Representative examples of heterocyclylalkyl include, but are not limited to, piperidin-4-ylmethyl, piperazin-1-ylmethyl, 3-methyl-1-pyrrolidin-1-ylbutyl, (1R)-3-methyl-1-pyrrolidin-1-ylbutyl, (1S)-3-methyl-1-pyrrolidin-1-ylbutyl, and 3-morpholinopropyl.

The term "hydroxy," as used herein, means an —OH group.

The term "hydroxyalkyl," as used herein, refers to an alkyl group, as defined herein, substituted with at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

In some instances, the number of carbon atoms in a group (e.g., alkyl, alkoxy, or cycloalkyl) is indicated by the prefix "Cx-Cy-", wherein x is the minimum and y is the maximum number of carbon atoms in the group. Thus, for example, "$C_1$-$C_3$-alkyl" refers to an alkyl group containing from 1 to 3 carbon atoms.

The term "substituent" refers to a group substituted on an atom of the indicated group.

When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below). Substituent groups include, but are not limited to, halogen, =O, =S, cyano, nitro, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, arylalkyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, carboxy (—COOH), ketone, amide, carbamate, phosphoryl, selenyl, and acyl.

Compounds

Disclosed herein is a compound of formula (I):

(I)

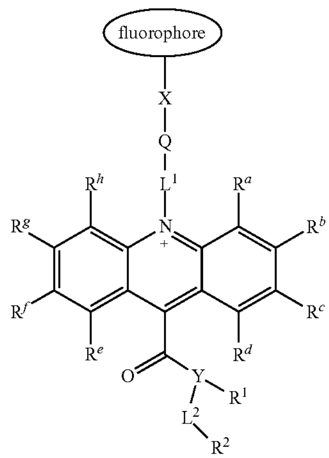

or a salt thereof, wherein: X is —NH— or a diamine linker; Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; when Y is oxygen or sulfur, $R^1$ is absent; Q is —$SO_2$— or —CO—; $L^1$ and $L^2$ are each independently selected from alkylene and heteroalkylene; $R^2$ is selected from —COOZ and —CN; Z is selected from hydrogen, alkyl, alkenyl, alkynyl, aryl, heteroaryl, cycloalkyl, heterocyclyl, arylalkyl, heteroarylalkyl, cycloalkylalkyl, heterocyclylalkyl, aryloxy, and heteroalkyl; and $R^a$, $R^b$, $R^c$, $R^d$, $R^e$, $R^f$, $R^g$, and $R^h$ are each independently selected from hydrogen, $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; wherein each alkyl, alkenyl, alkynyl, aryl, heteroaryl, cycloalkyl, heterocyclyl, arylalkyl, heteroarylalkyl, cycloalkylalkyl, heterocyclylalkyl, aryloxy, heteroalkyl, alkylene, and heteroalkylene is independently optionally substituted with 1, 2, 3, 4, or 5 substituents.

The group X is —NH— or a diamine linker. In some embodiments, X is —NH—. In some embodiments, X is a diamine linker. In some embodiments, the diamine linker may have formula —NR'-L'—NR"—, wherein R' and R" are each independently selected from hydrogen and methyl, and L' is selected from alkylene, heteroalkylene, cycloalkylene, and cycloalkenylene. In some embodiments, the diamine linker may by a cyclic diamine linker (e.g., a monocyclic or bicyclic diamine linker). In some embodiments, the diamine linker may be a rigid diamine linker. Exemplary rigid diamine linkers include the following:

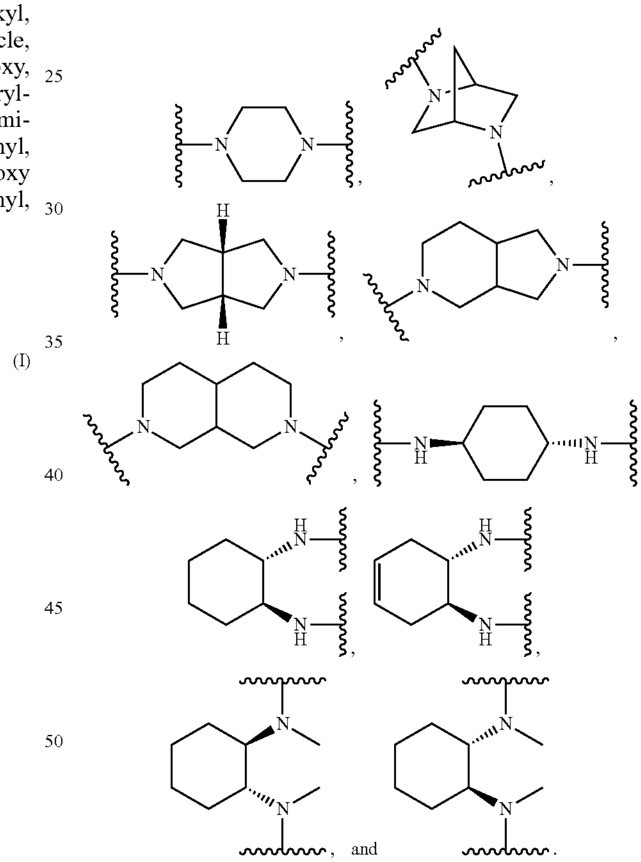

In some embodiments, X is selected from:

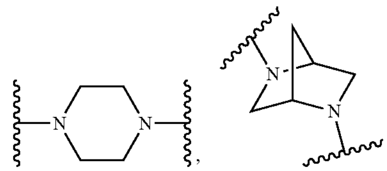

-continued

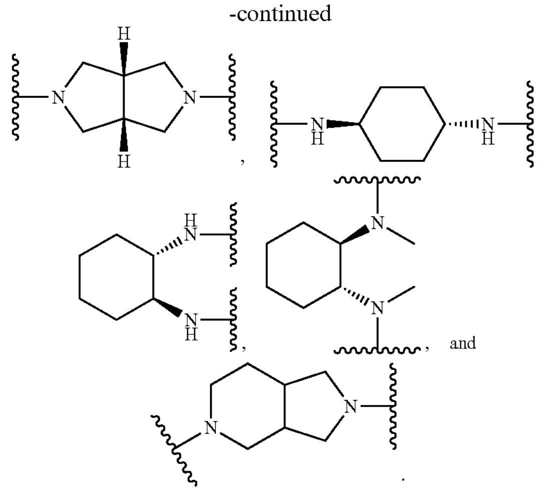

and

In some embodiments, X is:

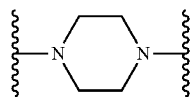

The group Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; and when Y is oxygen or sulfur, $R^1$ is absent.

In some embodiments, Y is nitrogen and $R^1$ is —$SO_2$-A. In some embodiments, A is aryl. In some embodiments, A is phenyl. In some embodiments, A is unsubstituted or substituted with 1, 2, 3, 4, or 5 substituents selected from $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, and amino. In some embodiments, A is phenyl that is substituted with 1 substituent selected from $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, and amino. In some embodiments, A is phenyl that is substituted with 1 substituent selected from $C_1$-$C_4$ alkyl. In some embodiments, A is phenyl that is substituted with 1 methyl group. In some embodiments, A is p-tolyl.

$R^2$ is selected from —COOZ and —CN, and Z is selected from hydrogen, alkyl, alkenyl, alkynyl, aryl, heteroaryl, cycloalkyl, heterocyclyl, arylalkyl, heteroarylalkyl, cycloalkylalkyl, heterocyclylalkyl, aryloxy, and heteroalkyl. In some embodiments, $R^2$ is —COOZ. In some embodiments, Z is selected from hydrogen and $C_1$-$C_4$ alkyl. In some embodiments, Z is hydrogen.

In some embodiments, Q is —CO—. In some embodiments, Q is —$SO_2$—.

$L^1$ and $L^2$ are each independently selected from alkylene and heteroalkylene. In some embodiments, $L^1$ and $L^2$ are each independently $C_1$-$C_4$-alkylene. In some embodiments, $L^1$ is —$CH_2CH_2CH_2$—. In some embodiments, $L^2$ is —$CH_2CH_2CH_2$—.

In some embodiments, each $R^a$, $R^b$, $R^c$, $R^d$, $R^e$, $R^f$, $R^g$, and $R^h$ is hydrogen.

In some embodiments, the compound is a compound of formula (Ia):

(Ia)

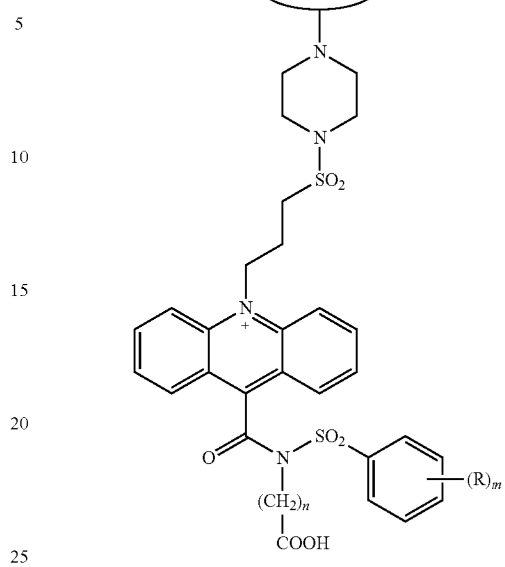

or a salt thereof, wherein: each R is independently selected from the group consisting of $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; m is 0, 1, 2, 3, 4, or 5; and n is 1, 2, 3, 4, 5, or 6.

In some embodiments, m is 1 or 2. In some embodiments, m is 1. In some embodiments, m is 1 and R is $C_1$-$C_4$ alkyl. In some embodiments, m is 1 and R is methyl. In some embodiments, n is 3.

In some embodiments, the compound is a compound of formula (Ib), or a salt thereof:

(Ib)

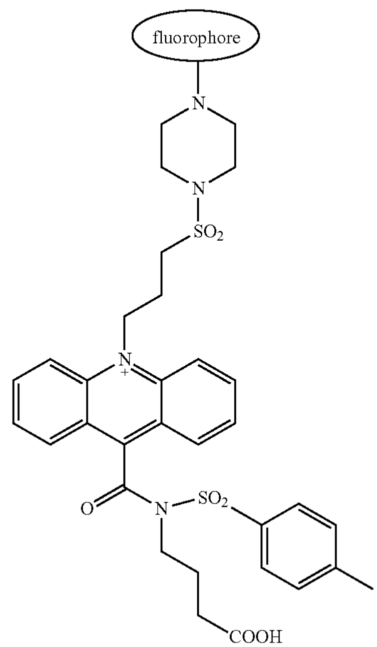

Any reference made herein to a compound of formula (I) should also be interpreted as reference to a compound of formula (Ia) or formula (Ib), whether expressly stated or not.

In some embodiments, in any of the compounds of formula (I), formula (Ia), or formula (Ib), the fluorophore is selected from a fluorescein, a rhodamine, a boron-dipyrromethene, a cyanine, an oxazine, a thiazine, a coumarin, a naphthalimide, a rhodol, a naphthalene, a squaraine, a porphyrin, a flavin, and a lanthanide-based dye.

Suitable fluorophores include, but are not limited to, QUASAR® dyes available from Biosearch Technologies, Novato, Calif.), fluorescein and fluorescein dyes (e.g., fluorescein isothiocyanate or FITC, naphthofluorescein, 4',5'-dichloro-2',7'-dimethoxy-fluorescein, 6-carboxyfluoresceins (e.g., FAM™), VIC®, NED™, carbocyanine, merocyanine, styryl dyes, oxonol dyes, phycoerythrin, erythrosin, eosin, rhodamine dyes (e.g., carboxytetramethylrhodamine or TAMRA™, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), OREGON GREEN® Dyes (e.g., OREGON GREEN 488, OREGON GREEN 500, OREGON GREEN 514), TEXAS RED®, TEXAS RED-X, SPECTRUM RED™, SPECTRUM GREEN™, cyanine dyes (e.g., CY-3™, CY-5™, CY-3.5™, CY-5.5™), ALEXA FLUOR® dyes (e.g., ALEXA FLUOR 350, ALEXA FLUOR 488, ALEXA FLUOR 532, ALEXA FLUOR 546, ALEXA FLUOR 568, ALEXA FLUOR 594, ALEXA FLUOR 633, ALEXA FLUOR 660 and ALEXA FLUOR 680), BODIPY® dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDye® (e.g., IRD40, IRD 700, IRD 800), and the like. Examples of other suitable fluorescent dyes that can be used and methods for linking or incorporating fluorescent dyes to oligonucleotides, such as probes, can be found in RP Haugland, "The Handbook of Fluorescent Probes and Research Chemicals", Publisher, Molecular Probes, Inc., Eugene, Oreg. (June 1992)). Fluorescent dyes as well as labeling kits are commercially available from, for example, Amersham Biosciences, Inc. (Piscataway, N.J.), Molecular Probes Inc. (Eugene, Oreg.), and New England Biolabs Inc. (Beverly, Mass.).

As those skilled in the art appreciate, a fluorophore can be attached to a molecule via reaction of two reactive moieties, one on the fluorophore and one on the remainder of the molecule. For example, many commercially available fluorophores are available with a reactive functional group such as a carboxylic acid, an isocyanate, an isothiocyanate, a maleimide, or an ester such as a succinimidyl, pentafluorophenyl or tetrafluorophenyl ester. The fluorophore can be chosen to include a reactive group that will react with a functional group on the remainder of the molecule. For example, a fluorophore isothiocyanate or a fluorophore succinimidyl ester can react with an amine group. It will be understood that the term "fluorophore" as used when describing the molecules disclosed herein includes both the fluorescent moiety itself and also any linking atoms that serve to connect the fluorescent moiety to the remainder of the molecule.

In some embodiments, the fluorophore is selected from:

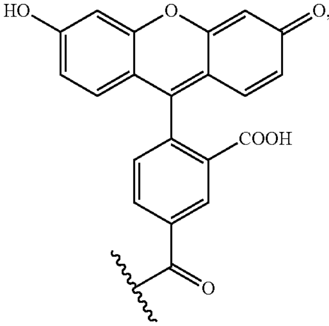

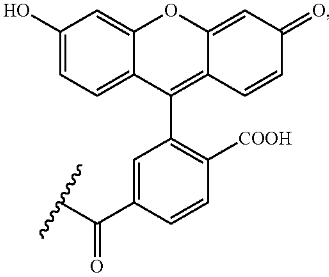

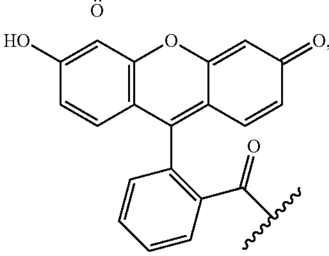

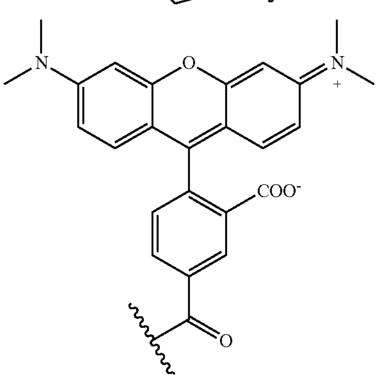

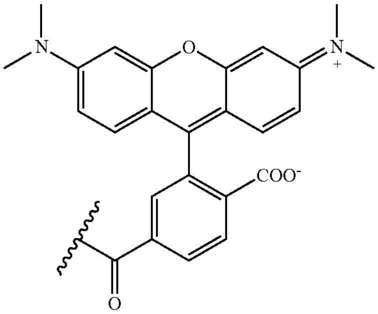

-continued
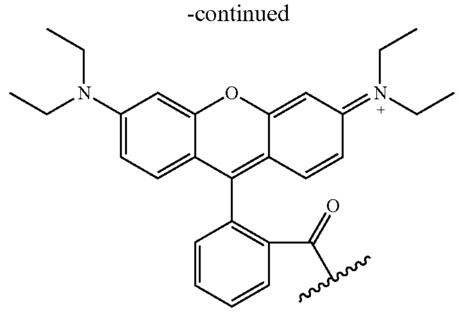
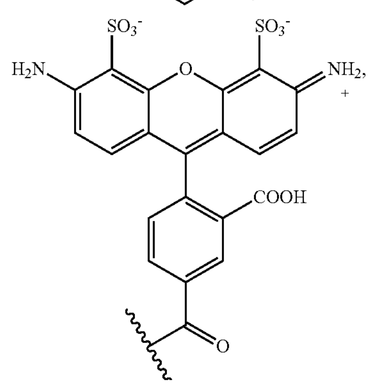
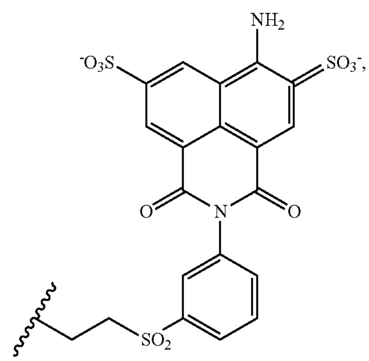
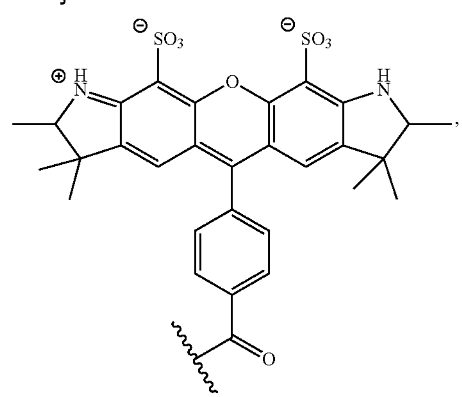
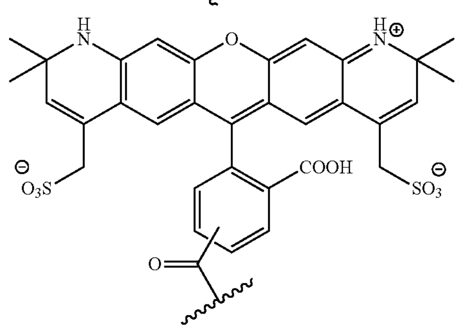
-continued
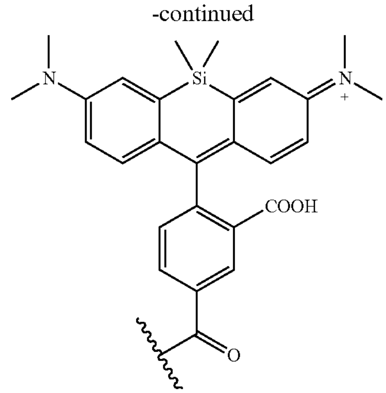
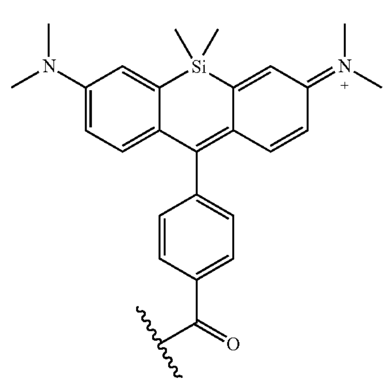
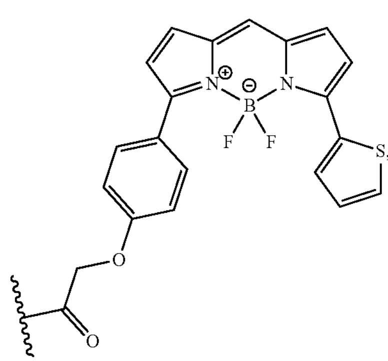
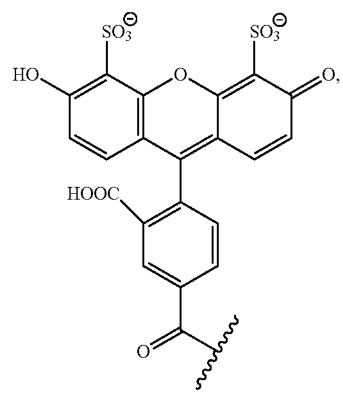

-continued

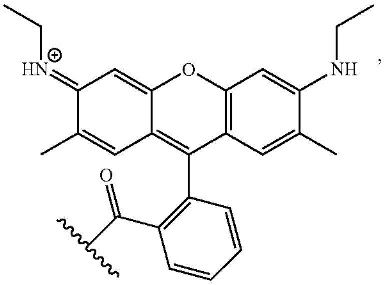

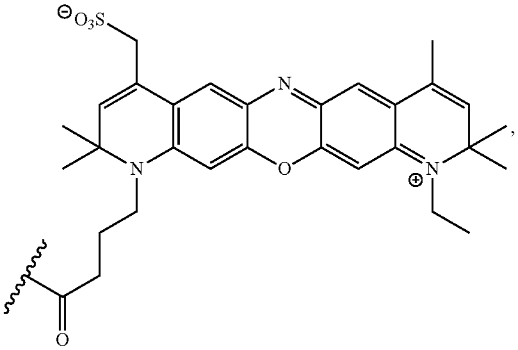

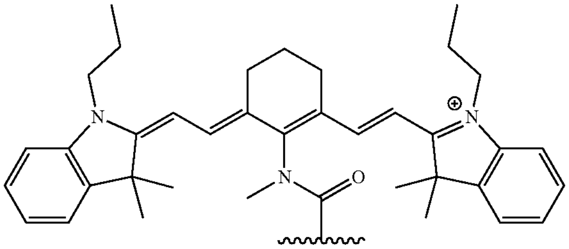

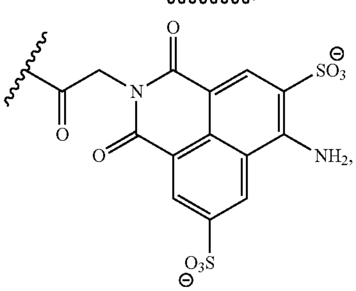

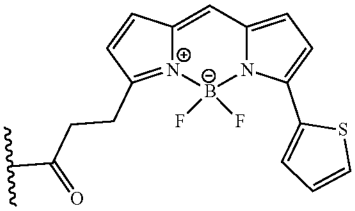

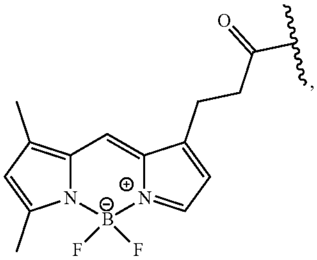

-continued

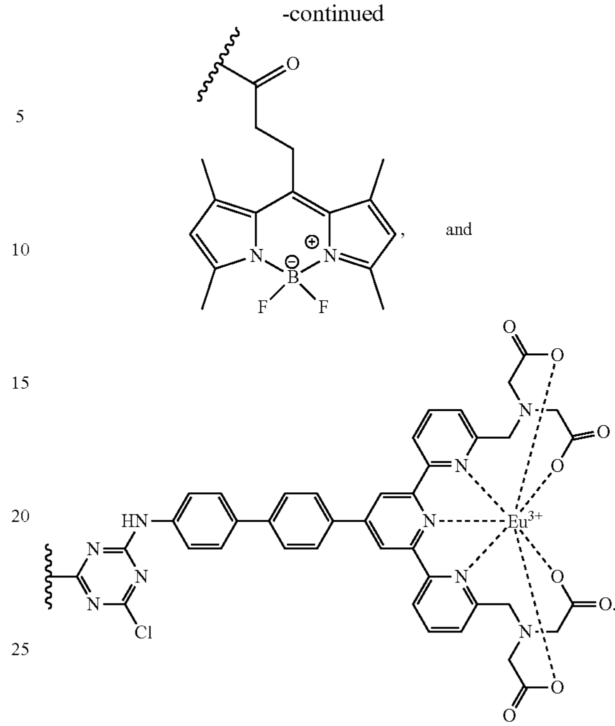

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", 5$^{th}$ edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms as well as geometric isomers, and that these also constitute an aspect of the invention.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^{2}H$, $^{3}H$, $^{13}C$, $^{4}C$, $^{5}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain advantages resulting from greater metabolic stability, for example increased in vivo half-life, and may therefore be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying examples using appropriate isotopically-labeled reagent in place of non-isotopically-labeled reagent.

A compound disclosed herein may be in the form of a salt. The salts may be prepared during the final isolation and purification of the compounds or separately, for example by reacting a basic group of the compound (e.g., an amino group) with a suitable acid or by reacting an acidic group of the compound (e.g., a carboxylic acid group) with a suitable base.

Acid salts may be prepared during the final isolation and purification of the compounds or separately by reacting a suitable group of the compound, such as an amino group, with a suitable acid. For example, a compound may be dissolved in a suitable solvent, such as but not limited to methanol and water, and treated with at least one equivalent of an acid, such hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

Compounds of formula (I) may be synthesized by a variety of methods, including those illustrated in Scheme 1, starting from the compound carboxypropylsulfopropyl-acridinium (CPSP-acridinium, 9-[N-tosyl-N-(3-carboxypropyl)]-10-(3-sulfopropyl)acridinium carboxamide), described by Adamczyk et al., *J. Org. Chem.* 1998, 63(16), 5636-5639.

Scheme 1.

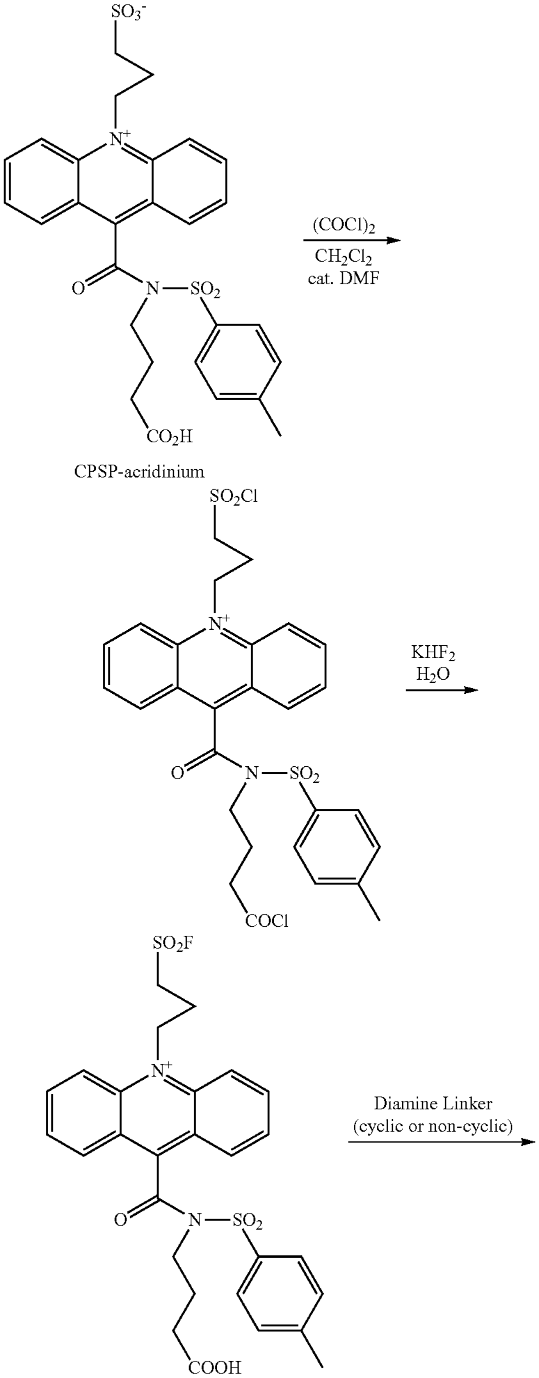

CPSP-acridinium

-continued

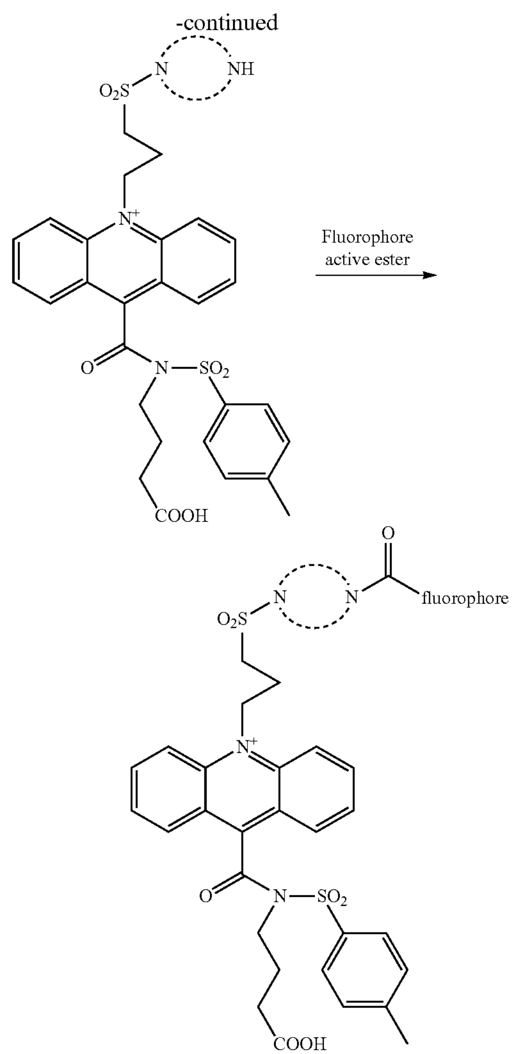

One skilled in the art will appreciate that Scheme 1 illustrates synthesis of certain compounds with particular substituent groups (e.g., $R^1$, $R^2$, $L^1$, $L^2$, X, and Y groups), but that compounds with other groups at the corresponding positions can be prepared in similar ways.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the disclosure can be accomplished by methods analogous to those described in the synthetic schemes described herein and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

Conjugates

Also disclosed herein are conjugates of formula (II):

(II)

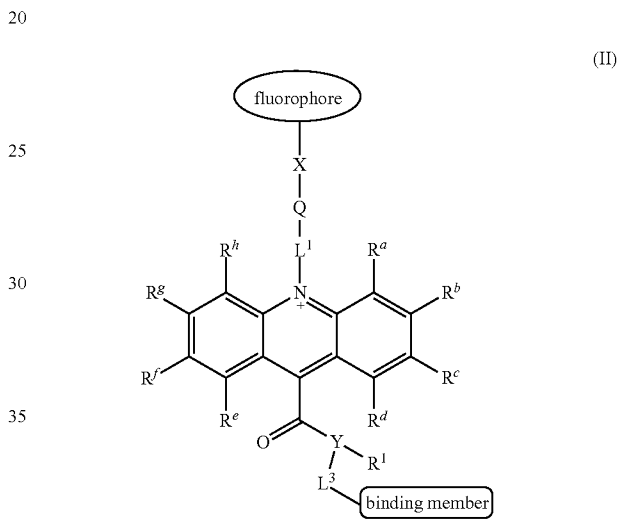

wherein: X is —NH— or a diamine linker; Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; when Y is oxygen or sulfur, $R^1$ is absent; Q is —$SO_2$— or —CO—; L' is selected from alkylene and heteroalkylene; $L^3$ is a linker; $R^a$, $R^b$, $R^c$, $R^d$, $R^e$, $R^f$, $R^g$, and $R^h$ are each independently selected from hydrogen, $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; and the binding member is a molecule capable of binding to a target analyte; wherein each alkyl, alkenyl, alkynyl, aryl, heteroaryl, cycloalkyl, heterocyclyl, arylalkyl, heteroarylalkyl, cycloalkylalkyl, heterocyclylalkyl, alkylene, and heteroalkylene is independently optionally substituted with 1, 2, 3, 4, or 5 substituents.

The groups X, Y, $R^1$, A, $L^1$, $R^a$, $R^b$, $R^c$, $R^d$, $R^e$, $R^f$, $R^g$, $R^h$, and the fluorophore are the same as those described above for formula (I). Any group or combination of groups described above for compounds of formula (I) may also be included in a compound of formula (II).

In compounds of formula (II), $L^3$ is a linker. A wide variety of linkers can be used in the compounds of formula (II). In some embodiments, the linker may be a covalent bond. In some embodiments, the linker may be an alkylene linker, such as a $C_1$-$C_{40}$ alkylene linker, e.g., a $C_1$-$C_{30}$, $C_1$-$C_{20}$, $C_1$-$C_{12}$, $C_1$-$C_{10}$, $C_1$-$C_8$, $C_1$-$C_6$, or a $C_1$-$C_4$ alkylene linker. For example, the linker may be a a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, or $C_{40}$ alkylene linker.

In some embodiments, the linker may be a heteroalkylene linker, such as a polyethylene glycol linker. Such a linker may have a formula $—(CH_2CH_2O)_{n1}—CH_2CH_2—$, where n1 is an integer from 1 to 20. For example, in some embodiments, n1 is an integer from 1 to 20, 1 to 18, 1 to 16, 1 to 14, 1 to 12, 1 to 10, 1 to 9, 1 to 8, 1 to 7, 1 to 6, 1 to 5, or 1 to 4. In some embodiments, n1 is 1, 2, 3, 4, 5, 6, 7, 8, 9, 10, 11, 12, 13, 14, 15, 16, 17, 18, 19, or 20.

In some embodiments, the linker may include a moiety E, wherein E is the product of a reaction between two reactive groups. For example, the group E may be an amide, an ester, a carbamate, a triazole, a sulfonamide, a phosphoramide, a phosphate, or a sulfate.

The binding member is a molecule that can be used to detect an analyte of interest in the methods described herein. The terms "binding member," "specific binding partner," and "specific binding member" are used interchangeably herein and refer to one of two or more different molecules that specifically recognize the other molecule compared to substantially less recognition of other molecules. By "specifically bind" or "binding specificity," it is meant that the binding member binds the analyte molecule with specificity sufficient to differentiate between the analyte molecule and other components or contaminants of the sample. As will be appreciated by those in the art, an appropriate specific binding member will be determined by the analyte to be analyzed.

Binding members for a wide variety of target molecules are known or can be readily found or developed using known techniques. For example, when the target analyte is a protein, the binding members may include proteins, particularly antibodies or fragments thereof (e.g., antigen-binding fragments (Fabs), Fab' fragments, $F(ab')_2$ fragments), recombinant antibodies, chimeric antibodies, single-chain Fvs ("scFv"), single chain antibodies, single domain antibodies, such as variable heavy chain domains ("VHH"; also known as "VHH fragments") derived from animals in the Camelidae family (VHH and methods of making them are described in Gottlin et al., *Journal of Biomolecular Screening,* 14:77-85 (2009)), recombinant VHH single-domain antibodies, disulfide-linked Fvs ("sdFv"), anti-idiotypic ("anti-Id") antibodies, and functionally active epitope-binding fragments of any of the above, full-length polyclonal or monoclonal antibodies, antibody-like fragments, etc., other proteins, such as receptor proteins, Protein A, or Protein C. In embodiments where the analyte is a small molecule, such as a steroid, bilin, retinoid, or lipid, the first and/or the second binding member may be a scaffold protein (e.g., a lipocalin) or a receptor. In some cases, a binding member for protein analytes may be a peptide. For example, when the target analyte is an enzyme, suitable binding members may include enzyme substrates and/or enzyme inhibitors which may be a peptide, a small molecule, and the like. In some cases, when the target analyte is a phosphorylated species, a binding member may comprise a phosphate-binding agent. For example, the phosphate-binding agent may comprise metal-ion affinity media (see, e.g., U.S. Pat. No. 7,070,921 and U.S. Patent Application No. 2006/0121544). In other embodiments, the binding member may be a vitamin, a nutrient, a nutrient metabolite, a nucleic acid, a carbohydrate, a dendrimer, a dendritic structure, a glycoprotein, an antigen, a receptor, an enzyme, a pharmaceutical (e.g., an antibiotic), or a drug of abuse.

In certain cases, a specific binding member may be an aptamer, such as those described in U.S. Pat. Nos. 5,270,163; 5,475,096; 5,567,588; 5,595,877; 5,637,459; 5,683,867; and 5,705,337. The term "aptamer" as used herein refers to a nucleic acid or peptide molecule that can bind to pre-selected targets including small molecules, proteins, and peptides among others with high affinity and specificity. Nucleic acid aptamers (e.g., single-stranded DNA molecules or single-stranded RNA molecules) may be developed for capturing virtually any target molecule. Aptamers bind target molecules in a highly specific, conformation-dependent manner, typically with very high affinity, although aptamers with lower binding affinity can be selected. Aptamers may distinguish between target analyte molecules based on very small structural differences such as the presence or absence of a methyl or hydroxyl group and certain aptamers can distinguish between D- and L-enantiomers and diastereomers. Aptamers may bind small molecular targets, including drugs, metal ions, and organic dyes, peptides, biotin, and proteins. Aptamers can retain functional activity after biotinylation, fluorescein labeling, and when attached to glass surfaces and microspheres.

Nucleic acid aptamers are oligonucleotides that may be single stranded oligodeoxynucleotides, oligoribonucleotides, or modified oligodeoxynucleotides or oligoribonucleotides. A "modified" oligodeoxynucleotide or oligoribonucleotide refers to nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl; 2-O-alkyl; 2-O-allyl; 2'-S-alkyl; 2'-S-allyl; 2'-fluoro-; 2'-halo or 2-azido-ribose, carbocyclic sugar analogues, anomeric sugars; epimeric sugars such as arabinose, xyloses or lyxoses, pyranose sugars, furanose sugars, and sedoheptulose.

Peptide aptamers may be designed to interfere with protein interactions. Peptide aptamers may be based on a protein scaffold onto which a variable peptide loop is attached, thereby constraining the conformation of the aptamer. In some cases, the scaffold portion of the peptide aptamer is derived from bacterial thioredoxin A (TrxA).

When the analyte is a carbohydrate, suitable binding members include, for example, antibodies, lectins, and selectins. As will be appreciated by those of ordinary skill in the art, any molecule that can specifically associate with an analyte of interest may potentially be used as a binding member.

In some embodiments, the conjugate comprises an additional specific binding member, which may serve as a carrier moiety for the dye construct. The additional specific binding member may be covalently linked to any of the specific binding members described above, or non-covalently linked to compounds such as, for example, lysosomes, hydrogels, or a dendrimer with dye intercalated within dendrimer cavities.

In certain embodiments, suitable analyte/binding member complexes can include, but are not limited to, antibodies/antigens, antigens/antibodies, receptors/ligands, ligands/receptors, proteins/nucleic acid, enzymes/substrates and/or inhibitors, carbohydrates (including glycoproteins and glycolipids)/lectins and/or selectins, proteins/proteins, proteins/small molecules, etc.

Methods

The disclosure provides methods of detecting one or more analytes of interest in a biological sample using the conjugates described herein.

Analyte of Interest

The terms “analyte,” “target analyte,” and “analyte of interest,” are used interchangeably and refer to the analyte being measured in the methods disclosed herein. As will be appreciated by those in the art, any analyte that can be specifically bound by a binding member (e.g., a first specific binding member and a second specific binding member) may be detected and, optionally, quantified using the methods of the present disclosure.

In some embodiments, the analyte may be a biomolecule. Non-limiting examples of biomolecules include macromolecules such as proteins, lipids, and carbohydrates. In certain instances, analytes include hormones, antibodies, growth factors, cytokines, enzymes, receptors (e.g., neural, hormonal, nutrient, and cell surface receptors) or their ligands, cancer markers (e.g., PSA, TNF-alpha), markers of myocardial infarction (e.g., troponin and creatine kinase), toxins, drugs (e.g., drugs of addiction), and metabolic agents (e.g., vitamins). Non-limiting embodiments of protein analytes include peptides, polypeptides, protein fragments, protein complexes, fusion proteins, recombinant proteins, phosphoproteins, glycoproteins, lipoproteins, or the like.

In certain embodiments, the analyte may be a post-translationally modified protein (e.g., phosphorylated, methylated, glycosylated protein) and a corresponding binding member (described above) may be an antibody specific to a post-translational modification. A modified protein may be bound to a first binding member immobilized on a solid support where the first binding member binds to the modified protein but not the unmodified protein. In other embodiments, a first binding member may bind to both the unmodified and the modified protein, and a second binding member may be specific to the post-translationally modified protein.

In some embodiments, the analyte may be a cell, such as, for example, a circulating tumor cell, pathogenic bacteria cell, or a fungal cell. In other embodiments, the analyte may be a virus (e.g., retrovirus, herpesvirus, adenovirus, lentivirus, Filovirus (Ebola), hepatitis virus (e.g., A, B, C, D, and E), or human papilloma virus (HPV)).

A non-limiting list of analytes that may be analyzed in accordance with the present disclosure include thyroglobulin, prolactin, Aβ42 amyloid beta-protein, fetuin-A, tau, secretogranin II, prion protein, alpha-synuclein, tau protein, neurofilament light chain, parkin, PTEN induced putative kinase 1, DJ-1, leucine-rich repeat kinase 2, mutated ATP13A2, Apo H, ceruloplasmin, peroxisome proliferator-activated receptor gamma coactivator-1 alpha (PGC-1α), transthyretin, vitamin D-binding protein, proapoptotic kinase R (PKR) and its phosphorylated PKR (pPKR), CXCL13, IL-12p40, CXCL13, IL-8, Dkk-3 (semen), p 14 endocan fragment, serum, ACE2, autoantibody to CD25, hTERT, CAI25 (MUC 16), VEGF, sIL-2, osteopontin, human epididymis protein 4 (HE4), alpha-fetoprotein (AFP), albumin, albuminuria, microalbuminuria, neutrophil gelatinase-associated lipocalin (NGAL), interleukin 18 (IL-18), kidney injury molecule-1 (KIM-1), liver fatty acid binding protein (L-FABP), LMP1, BARF1, IL-8, carcinoembryonic antigen (CEA), BRAF, CCNI, EGRF, FGF19, FRS2, GREB1, LZTS1, alpha-amylase, carcinoembryonic antigen (CEA), CA125, interleukin-8 (IL-8), thioredoxin, beta-2 microglobulin, tumor necrosis factor-alpha receptors, CA15-3, follicle-stimulating hormone (FSH), leutinizing hormone (LH), T-cell lymphoma invasion and metastasis 1 (TIAM1), N-cadherin, EC39, amphiregulin, dUTPase, secretory gelsolin (pGSN), PSA (prostate specific antigen), thymosin 015, insulin, plasma C-peptide, glycosylated hemoglobin (HBA1c), C-Reactive Protein (CRP), interleukin-6 (IL-6), ARHGDIB (Rho GDP-dissociation inhibitor 2), CFL1 (cofilin-1), PFN1 (profilin-1), GSTP1 (glutathione S-transferase P), S100A11 (protein S100-A11), PRDX6 (peroxiredoxin-6), HSPE1 (10 kDa heat shock protein, mitochondrial), LYZ (lysozyme C precursor), GPI (glucose-6-phosphate isomerase), HIST2H2AA (histone H2A type 2-A), GAPDH (glyceraldehyde-3-phosphate dehydrogenase), HSPG2 (basement membrane-specific heparan sulfate proteoglycan core protein precursor), LGALS3BP (galectin-3-binding protein precursor), CTSD (cathepsin D precursor), APOE (apolipoprotein E precursor), IQGAP1 (Ras GTPase-activating-like protein IQGAP1), CP (Ceruloplasmin precursor), and IGLC2 (IGLC1 protein), PCDGF/GP88, EGFR, HER2, MUC4, IGF-IR, p27(kipl), Akt, HER3, HER4, PTEN, PIK3CA, SHIP, Grb2, Gab2, PDK-1 (3-phosphoinositide dependent protein kinase-1), TSC1, TSC2, mTOR, MIG-6 (ERBB receptor feedback inhibitor 1), S6K, src, KRAS, MEK mitogen-activated protein kinase 1, cMYC, TOPO II topoisomerase (DNA) II alpha 170 kDa, FRAP1, NRG1, ESR1, ESR2, PGR, CDKN1B, MAP2K1, NEDD4-1, FOXO3A, PPPIRIB, PXN, ELA2, CTNNB1, AR, EPHB2, KLF6, ANXA7, NKX3-1, PITX2, MKI67, PHLPP, adiponectin (ADIPOQ), fibrinogen alpha chain (FGA), leptin (LEP), advanced glycosylation end product-specific receptor (AGER or RAGE), alpha-2-HS-glycoprotein (AHSG), angiogenin (ANG), CD14 molecule (CD14), ferritin (FTH1), insulin-like growth factor binding protein 1 (IGFBPI), interleukin 2 receptor, alpha (IL2RA), vascular cell adhesion molecule 1 (VCAM1) and Von Willebrand factor (VWF), myeloperoxidase (MPO), IL1α, TNFα, perinuclear anti-neutrophil cytoplasmic antibody (p-ANCA), lactoferrin, calprotectin, Wilm’s tumor-1 protein, aquaporin-1, MLL3, AMBP, VDAC1, *E. coli* enterotoxins (heat-labile exotoxin, heat-stable enterotoxin), influenza HA antigen, tetanus toxin, diphtheria toxin, botulinum toxins, Shiga toxin, Shiga-like toxin I, Shiga-like toxin II, *Clostridium difficile* toxins A and B, glial fibrillary acidic protein (GFAP), ubiquitin carboxy-terminal hydrolase L1 (UCH-L1), S100B, neurofilament light polypeptide (NF-L), Tau, pTau, Amyloid Beta 40 and 42, neuron-specific enolase (NSE), brain naturietic peptide (BNP), N-terminal (NT)-pro hormone BNP (NT-proBNP), CA19-9, placental growth factor (PlGF), sFlt-1, opioids, tacrolimus, protein induced by vitamin K absence-II (PIVKA-II), etc.

Other examples of analytes include drugs of abuse (e.g. cocaine), protein biomarkers (including, but not limited to, nucleolin, nuclear factor-kB essential modulator (NEMO), CD-30, protein tyrosine kinase 7 (PTK7), vascular endothelial growth factor (VEGF), MUC1 glycoform, immunoglobulin Heavy Chains (IGHM), Immunoglobulin E, avβ3 integrin, α-thrombin, HIV gp120, NF-κB, E2F transcription factor, HER3, Plasminogen activator inhibitor, Tenascin C,CXCL12/SDF-1, prostate specific membrane antigen (PSMA), and HGC-27); cells (including, but not limited to, non-small cell lung cancer (NSCLC), colorectal cancer cells, (DLD-1), H23 lung adenocarcinoma cells, Ramos cells, T-cell acute lymphoblastic leukemia (T-ALL) cells, CCRF-CEM, acute myeloid leukemia (AML) cells (HL60), small-cell lung cancer (SCLC) cells, NCIH69, human glioblastoma cells, U118-MG, PC-3 cells, HER-2-overexpressing human breast cancer cells, SK-BR-3, pancreatic cancer cells (Mia-PaCa-2)); and infectious agents (including, but not limited to, *Mycobacterium tuberculosis, Staphylococcus aureus, Shigella dysenteriae, Escherichia coli* O157:H7, *Campylobacter jejuni, Listeria monocytogenes, Pseudomonas aeruginosa, Salmonella* O8, and *Salmonella enteritidis*).

Samples

The terms "sample," "test sample," and "biological sample" are used interchangeably herein and refer to a fluid sample containing or suspected of containing an analyte of interest. In some cases, the sample may comprise a liquid, fluent particulate solid, or fluid suspension of solid particles. In certain embodiments, the sample may be a liquid sample or a liquid extract of a solid sample. In some cases, the sample may be processed prior to the analysis described herein. For example, the sample may be separated or purified from its source prior to analysis; however, in certain embodiments, an unprocessed sample containing the analyte may be assayed directly. The sample may be derived from any suitable source. For example, the sample source may be synthetic (e.g., produced in a laboratory), the environment (e.g., air, soil, fluid samples, e.g., water supplies, etc.), an animal (e.g., a mammal), a plant, or any combination thereof. In a particular example, the sample is a human bodily substance (e.g., bodily fluid, blood, serum, plasma, urine, saliva, sweat, sputum, semen, mucus, lacrimal fluid, lymph fluid, amniotic fluid, interstitial fluid, lung lavage, cerebrospinal fluid, feces, tissue, or organ). Tissues may include, but are not limited to, skeletal muscle tissue, liver tissue, lung tissue, kidney tissue, myocardial tissue, brain tissue, bone marrow, cervix tissue, skin, etc. In certain cases, the source of the sample may be an organ or tissue, such as a biopsy sample, which may be solubilized by tissue disintegration/cell lysis.

In some cases, the fluid sample may be diluted prior to use in an assay. For example, in embodiments where the source of an analyte molecule is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use.

In some cases, as mentioned above, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the sample is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

Solid Support

In certain embodiments, one or more compounds of formula (II) are immobilized on a solid support. The terms "solid phase" or "solid support" are used interchangeably herein and refer to any material that can be used to attach, attract, and/or immobilize one or more specific binding members. For example, a specific binding member can be part of the conjugate of Formula (II) disclosed herein. Any solid support known in the art can be used in the methods described herein, including but not limited to, solid supports made out of polymeric materials in the form of planar substrates or beads. In certain embodiments, the bead may be a particle, e.g., a microparticle. The terms "bead" and "particle" are used herein interchangeably and refer to a substantially spherical solid support. The terms "microparticle" and "microbead" are used interchangeably herein and refer to a microbead or microparticle that is allowed to occupy or settle in an array of wells, such as, for example, in an array of wells in a detection module. The microparticle or microbead may contain at least one compound of formula (II) containing at least one specific binding member that binds to an analyte of interest. When two or more analytes of interest are detected, the method may comprise one microparticle containing two or more different compounds of formula (II), containing first and second specific binding members that bind to a first analyte and a second microparticle containing third and fourth specific binding members that bind to a second analyte, and so on.

In some embodiments, the microparticle may be between about 0.1 nm and about 10 microns, between about 50 nm and about 5 microns, between about 100 nm and about 1 micron, between about 0.1 nm and about 700 nm, between about 500 nm and about 10 microns, between about 500 nm and about 5 microns, between about 500 nm and about 3 microns, between about 100 nm and 700 nm, or between about 500 nm and 700 nm. For example, the microparticle may be about 4-6 microns, about 2-3 microns, or about 0.5-1.5 microns. Particles less than about 500 nm may be referred to as "nanoparticles." Thus, the microparticle optionally may be a nanoparticle between about 0.1 nm and about 500 nm, between about 10 nm and about 500 nm, between about 50 nm and about 500 nm, between about 100 nm and about 500 nm, about 100 nm, about 150 nm, about 200 nm, about 250 nm, about 300 nm, about 350 nm, about 400 nm, about 450 nm, or about 500 nm.

In certain embodiments, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, NiO/Fe. Examples of ferrimagnetic materials include NiFe204, $CoFe_2O_4$, $Fe_3O_4$ (or $FeO·Fe_2O_3$). Beads can have a solid core portion that is magnetic and is surrounded by one or more non-magnetic layers. Alternately, the magnetic portion can be a layer around a non-magnetic core. The solid support on which a binding member (e.g., a compound of Formula (II)) is immobilized may be stored in dry form or in a liquid. The magnetic beads may be subjected to a magnetic field prior to or after contacting with the sample with a magnetic bead on which a binding member is immobilized.

The solid support may be contacted with a volume of the sample using any suitable method known in the art. The term "contacting," as used herein, refers to any type of combining action which brings a binding member immobilized thereon into sufficiently close proximity with an analyte of interest in a sample such that a binding interaction will occur if the analytes of interest specific for the binding members are present in the sample. Contacting may be achieved in a variety of different ways, including combining the sample with microparticles or exposing target analytes to microparticles comprising binding members by introducing the microparticles in close proximity to the analytes. The contacting may be repeated as many times as necessary.

Whatever method is used, the solid support is contacted with a volume of sample under conditions whereby one or more analytes, if present in the sample, bind to at least one specific binding member (e.g., part of conjugate of Formula (II) disclosed herein) immobilized on the surface of the solid support (e.g., microparticle). In one embodiment, contact between the solid support and the sample volume is maintained (i.e., incubated) for a sufficient period of time to allow for the binding interaction between the specific binding member and analyte to occur. In one embodiment, the sample volume is incubated on a solid support for at least 30 seconds and at most 10 minutes. For example, the sample may be incubated with the solid support for about 1, 2, 3, 4, 5, 6, 7, 8, or 9 minutes. In one embodiment, the sample may be incubated with the microparticles for about 2 minutes. In addition, the incubating may be in a binding buffer that facilitates the specific binding interaction, such as, for example, albumin (e.g., BSA), non-ionic detergents (Tween-20, Triton X-100), and/or protease inhibitors (e.g., PMSF). The binding affinity and/or specificity of a specific binding member may be manipulated or altered in the assay by varying the binding buffer. In some embodiments, the binding affinity and/or specificity may be increased or decreased by varying the binding buffer. Other conditions for the binding interaction, such as, for example, temperature and salt concentration, may also be determined empirically or may be based on manufacturer's instructions. For example, the contacting may be carried out at room temperature (21° C.-28° C., e.g., 23° C.-25° C.), 37° C., or 4° C.

In one embodiment, the solid support desirably comprises a plurality (e.g., 2 or more, 50 or more, 100 or more, 1,000 or more, or 5,000 or more) of specific binding members immobilized on the surface thereof which bind to an analyte of interest. Following a sufficient incubation time between the solid support and the sample, as discussed above, one or more analytes of interest present in the sample desirably are captured on the surface of the solid support via the specific binding members immobilized on the surface of the solid support. The term "immobilized," as used herein, refers to a stable association of a binding member with a surface of a solid support.

As discussed above, the methods disclosed herein are suitable for detecting two or more different analytes. Thus, in some embodiments, the method may comprise capturing a second, third, fourth, or subsequent analyte of interest on a surface of a second, third, fourth, or subsequent solid support, wherein (i) each of the first, second, third, fourth, and subsequent analytes is different from each other, and (ii) the second, third, fourth, or subsequent solid support comprises one or more specific binding members immobilized on the surface thereof which bind to the second, third, fourth, or subsequent analyte. The method may further comprise reacting the captured second, third, fourth, or subsequent analyte with a second, third, fourth, or subsequent conjugate, wherein the second, third, fourth, or subsequent conjugate comprises a specific binding member that is labeled with a fluorophore and binds to the second, third, fourth, or subsequent analyte, and wherein each fluorophore is different.

In certain embodiments, a solid support may also comprise a protective, blocking, or passivating layer that can eliminate or minimize non-specific attachment of non-capture components (e.g., analyte molecules, binding members) to the binding surface during the assay which may lead to false positive signals during detection or to loss of signal. Examples of materials that may be utilized in certain embodiments to form passivating layers include, but are not limited to, polymers (e.g., polyethylene glycol) that repel the non-specific binding of proteins; naturally occurring proteins (e.g., serum albumin and casein); surfactants (e.g., zwitterionic surfactants, sulfobetaines); naturally occurring long-chain lipids; polymer brushes, and nucleic acids, such as salmon sperm DNA.

In a particular embodiment, a specific binding member (e.g., a compound of formula (II) containing a specific binding member) may be attached to a solid support via a linkage, which may comprise any moiety, functionalization, or modification of the support and/or binding member that facilitates the attachment of the binding member to the support. The linkage between the binding member and the support may include one or more chemical or physical (e.g., non-specific attachment via van der Waals forces, hydrogen bonding, electrostatic interactions, hydrophobic/hydrophilic interactions; etc.) bonds and/or chemical spacers providing such bond(s). Certain embodiments utilize binding members that are proteins or polypeptides, and any number of techniques may be used to attach a polypeptide to a wide variety of solid supports (see, e.g., U.S. Pat. No. 5,620,850; and Heller, *Acc. Chem. Res.,* 23: 128 (1990)).

In some embodiments, the binding affinity between analyte molecules and binding members should be sufficient to remain bound under the conditions of the assay, including wash steps to remove molecules or particles that are non-specifically bound. In some cases, for example in the detection of certain biomolecules, the binding constant of the analyte molecule to its complementary binding member may be between at least about $10^4$ and about $10^6$ $M^{-1}$, at least about $10^5$ and about $10^9$ $M^{-1}$, at least about $10^7$ and about $10^9$ $M^{-1}$, greater than about $10^9$ $M^{-1}$, or greater.

Multiplexing

In some embodiments, the method involves determining the presence of and/or concentration of an analyte in a sample. In this regard, the method may comprise contacting the biological sample with at least one first specific binding member and at least one second specific binding member, wherein the at least one first specific binding member and the at least one second specific binding member each specifically bind to the analyte of interest, thereby producing one or more first complexes comprising first specific binding member-analyte-second specific binding member, wherein the second specific binding member comprises the any one of the above-described conjugates. In such embodiments, the method further comprises detecting the presence or absence of a signal from the second specific binding member, wherein detection of the signal indicates that the analyte is present in the sample and the absence of the signal indicates that the analyte is not present in the sample. In each of these embodiments, the specific binding member may be part of a compound of Formula (II).

In certain embodiments, the method may also be used for determining the presence and/or concentration of a plurality of different analytes present in a sample (i.e., multiplexing). In this regard, the disclosed methods may include two or more specific binding members and solid supports (e.g., 2, 3, 4, 5, or more) to detect two or more (e.g., 2, 3, 4, 5, or more) target analytes in a sample, which is referred to herein as a "multiplex immunoassay" or "multiplex assay." Each of the specific binding members binds to a different analyte, and each specific binding member and/or solid support (e.g., microparticle) may comprise a different detectable label.

In some embodiments, the disclosure provides a method of detecting two or more analytes of interest in a biological sample, which comprises: (a) contacting the biological sample either simultaneously or sequentially with (i) at least one first specific binding member that binds to a first analyte of interest to form at least one first complex; and (ii) at least one second specific binding member that binds to a second analyte of interest to form at least one second complex, wherein each of the first and second specific binding members comprise any one of the above-described conjugates, and wherein the fluorophore of the conjugate in each of the first and second specific binding members is different; and (b) detecting the presence or absence of a signal from each of the first and second specific binding members, wherein (i) detection of a signal from the first specific binding member indicates that the first analyte is present in the sample and the absence of a signal from the first specific binding member indicates that the first analyte is not present in the sample; and (ii) detection of a signal from the second specific binding member indicates that the second analyte is present in the sample and the absence of a signal from the second specific binding member indicates that the second analyte is not present in the sample.

In other embodiments, the disclosure provides a method of detecting two or more analytes of interest in a biological sample, which comprises: (a) contacting the biological sample with at least one first specific binding member and at least one second specific binding member, wherein the at least one first specific binding member and the at least one second specific binding member each specifically bind to a first analyte of interest, thereby producing one or more first complexes comprising the first specific binding member-first analyte-second specific binding member, wherein the second specific binding member comprises any one of the above-described conjugates; and (b) contacting the biological sample either simultaneously or sequentially with at least one third specific binding member and at least one fourth specific binding member, wherein the at least one third specific binding member and the at least one fourth specific binding member each specifically bind to a second analyte of interest, thereby producing one or more second complexes comprising the third specific binding member-second analyte-fourth specific binding member, wherein the fourth specific binding member comprises any one of the above-described conjugates, and wherein the fluorophore in the conjugate in each of the second and fourth specific binding members is different; and (c) detecting the presence or absence of a signal from each of the second and fourth specific binding members, wherein (i) detection of a signal from the second specific binding member indicates that the first analyte is present in the sample and the absence of a signal from the second specific binding member indicates that the first analyte is not present in the sample and (ii) detection of a signal from the fourth specific binding member indicates that the second analyte is present in the sample and the absence of a signal from the fourth specific binding member indicates that the second analyte is not present in the sample.

In certain embodiments, the methods described herein may be used to detect more than two analytes of interest. For example, when a biological sample comprises three analytes of interest, the method may further comprise contacting the biological sample either simultaneously or sequentially with at least one fifth specific binding member and at least one sixth specific binding member, wherein the at least one fifth specific binding member and the at least one sixth specific binding member each specifically bind to a third analyte of interest, thereby producing one or more third complexes comprising the fifth specific binding member-third analyte-sixth specific binding member, wherein the sixth specific binding member comprises any one of the above-described conjugates, and wherein the fluorophore of the conjugate in each of the second, fourth and sixth specific binding members are different; and detecting the presence or absence of a signal from each of the second, fourth, and sixth specific binding members, wherein (i) detection of a signal from the second specific binding member indicates that the first analyte is present in the sample and the absence of a signal from the second specific binding member indicates that the first analyte is not present in the sample; (ii) detection of a signal from the fourth specific binding member indicates that the second analyte is present in the sample and the absence of a signal from the fourth specific binding member indicates that the second analyte is not present in the sample; and (iii) detection of a signal from the sixth specific binding member indicates that the third analyte is present in the sample and the absence of a signal from the sixth specific binding member indicates that the third analyte is not present in the sample.

Following reaction of one or more captured analytes with a conjugate as described herein, any specific binding member (e.g., antibody or antibody fragment), or component of the conjugate not bound to the captured analyte may be removed, followed by an optional wash step. Any unbound antibody, antibody fragment, or component of the conjugates may be separated from the complexes by any suitable means such as, for example, droplet actuation, electrophoresis, electrowetting, dielectrophoresis, electrostatic actuation, electric field mediated, electrode mediated, capillary force, chromatography, centrifugation, aspiration, or surface acoustic wave (SAW)-based washing methods.

It will be appreciated that different conformations of the analyte capture and complex formation methods described above are within the scope of the present disclosure. Indeed, the various components of the solid supports, specific binding members, conjugates, and fluorophores described above may be arranged or utilized in any suitable combination, conformation, or format. For example, the disclosed methods may be performed in one step, delayed one step, or two step format. Assay reagents (e.g., microparticles, conjugates, fluorophores, etc.) may be pre-mixed or added sequentially as appropriate.

Analyte Detection and Quantification

The presence or amount of analyte of interest present in a sample can be determined (e.g., quantified) using any suitable method known in the art. Such methods include, but are not limited to, immunoassays. Any suitable immunoassay may be utilized, such as, for example, a sandwich immunoassay (e.g., monoclonal-polyclonal sandwich immunoassays), competitive inhibition immunoassay (e.g., forward and reverse), chemiluminescent immunoassay, a competitive binding assay, heterogeneous assay, and capture on the fly assay. Immunoassay components and techniques that may be used in the disclosed methods are further described in, e.g., International Patent Application Publication Nos. WO 2016/161402 and WO 2016/161400. The method may involve single molecule counting. In one aspect, the assay employed is in a clinical chemistry format.

As discussed herein, the disclosed compounds include an acridinium moiety and a fluorophore that are linked via a rigid diamine linker. Thus, upon chemiluminescent triggering of the acridinium moiety, light output can be shifted to the emission wavelength of the attached fluorophore. The use of acridinium compounds as detectable labels in a homogeneous chemiluminescent assay is described in, e.g., Adamczyk et al, Bioorg. Med. Chem. Lett. 16: 1324-1328 (2006); Adamczyk et al, Bioorg. Med. Chem. Lett. 4: 2313-2317 (2004); Adamczyk et al, Biorg. Med. Chem. Lett. 14: 3917-3921 (2004); and Adamczyk et al, *Org. Lett.* 5: 3779-3782 (2003)). In one embodiment, chemiluminescent triggering of the acridinium moiety involves adding hydrogen peroxide to the biological sample prior to the detecting step. Hydrogen peroxide can be provided or supplied to the biological sample before, simultaneously with, or after the addition of specific binding member that comprises the above-described conjugate. The source of the hydrogen peroxide can be one or more buffers or other solutions that are known to contain hydrogen peroxide. In this regard, a solution of hydrogen peroxide can simply be added the biological sample.

In other embodiments, the fluorophore of the conjugate in each of the first, second, third, fourth, fifth, or subsequent specific binding members is different. Any suitable fluorophore known in the art and described herein can be attached to the disclosed compounds. The fluorescent signal from each specific binding member may be visualized and differentiated using any suitable device known in the art, including but not limited to, photo multiplier tubes, photodiode arrays, or charge coupled device cameras. In some embodiments, these devices may be fitted with filters capable of differentiating per wavelength.

In some embodiments, the concentration of an analyte in a sample that may be substantially accurately determined is less than about 5000 fM (femtomolar), less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 500 aM (attomolar), less than about 100 aM, less than about 10 aM, less than about 5 aM, less than about 1 aM, less than about 0.1 aM, less than about 500 zM (zeptomolar), less than about 100 zM, less than about 10 zM, less than about 5 zM, less than about 1 zM, less than about 0.1 zM, or less. For example, the concentration of analyte in the sample that may be substantially accurately determined is between about 5000 fM and about 0.1 fM, between about 3000 fM and about 0.1 fM, between about 1000 fM and about 0.1 fM, between about 1000 fM and about 0.1 zM, between about 100 fM and about 1 zM, between about 100 aM and about 0.1 zM, or a range defined by any of two of the foregoing values.

In some embodiments, the lower limit of detection (e.g., the lowest concentration of an analyte which may be determined in solution) is about 100 fM, about 50 fM, about 25 fM, about 10 fM, about 5 fM, about 2 fM, about 1 fM, about 500 aM (attomolar), about 100 aM, about 50 aM, about 10 aM, about 5 aM, about 1 aM, about 0.1 aM, about 500 zM (zeptomolar), about 100 zM, about 50 zM, about 10 zM, about 5 zM, about 1 zM, about 0.1 zM, or less.

The upper limit of detection (e.g., the upper concentration of an analyte which may be determined in solution) may be at least about 100 fM, at least about 1000 fM, at least about 10 pM (picomolar), at least about 100 pM, at least about 100 pM, at least about 10 nM (nanomolar), at least about 100 nM, at least about 1000 nM, at least about 10 pM, at least about 100 pM, at least about 1000 pM, at least about 10 mM, at least about 100 mM, at least about 1000 mM, or greater.

In some cases, the presence and/or concentration of the analyte in a sample may be detected rapidly, usually in less than about 1 hour, e.g., 45 minutes, 30 minutes, 15 minutes, 10 minutes, 5 minutes, 1 minute, or 30 seconds.

The disclosed method may comprise quality control components. "Quality control components" in the context of immunoassays and kits described herein, include, but are not limited to, calibrators, controls, and sensitivity panels. A "calibrator" or "standard" can be used (e.g., one or more, such as a plurality) in order to establish calibration (standard) curves for interpolation of the concentration of an analyte, such as an antibody. Alternatively, a single calibrator, which is near a reference level or control level (e.g., "low", "medium", or "high" levels), can be used. Multiple calibrators (i.e., more than one calibrator or a varying amount of calibrator(s)) can be used in conjunction to comprise a "sensitivity panel." The calibrator is optionally part of a series of calibrators in which each of the calibrators differs from the other calibrators in the series, such as, for example, by concentration or detection method (e.g., colorimetric or fluorescent detection).

Variations on the Disclosed Methods

The disclosed methods may be adapted as appropriate in view of other methods for analyzing analytes. Examples of well-known variations include, but are not limited to, immunoassay, such as sandwich immunoassay (e.g., monoclonal-polyclonal sandwich immunoassays), immunoassay including enzyme detection (enzyme immunoassay (EIA) or enzyme-linked immunosorbent assay (ELISA)), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, etc. In some instances, the descriptions below may overlap the method described above; in others, the descriptions below may provide alternates.

Immunoassay

The analyte of interest, and/or peptides or fragments thereof, may be analyzed using an immunoassay. Any immunoassay may be utilized. The immunoassay may be an enzyme-linked immunoassay (ELISA), a competitive inhibition assay, such as forward or reverse competitive inhibition assays, or a competitive binding assay, for example. In some embodiments, a detectable label (e.g., such as one or more fluorescent labels) is attached to a capture antibody and/or a detection antibody.

A heterogeneous format may be used. For example, after a sample is obtained from a subject, a first mixture is prepared. The mixture contains the sample being assessed for analyte of interest and a first specific binding member, wherein the first specific binding member and any analyte of interest contained in the sample to form a first specific binding member-analyte of interest complex. Preferably, the first specific binding member is an anti-analyte of interest antibody or a fragment thereof. The order in which the sample and the first specific binding member are added to form the mixture is not critical. Preferably, the first specific binding member is immobilized on a solid phase. The solid phase used in the immunoassay (for the first specific binding member and, optionally, the second specific binding member) can be any solid phase known in the art, such as, but not limited to, a magnetic particle, a bead, a nanobead, a microbead, a nanoparticle, a microparticle, a membrane, a scaffolding molecule, a film, a filter paper, a disc, or a chip (e.g., a microfluidic chip).

After the mixture containing the first specific binding member-analyte of interest complex is formed, any unbound analyte of interest is removed from the complex using any technique known in the art. For example, the unbound analyte of interest can be removed by washing. Desirably, however, the first specific binding member is present in excess of any analyte of interest present in the sample, such that all analyte of interest that is present in the sample is bound by the first specific binding member.

After any unbound analyte of interest is removed, a second specific binding member is added to the mixture to form a first specific binding member-analyte of interest-second specific binding member complex. The second specific binding member is preferably an anti-analyte of interest (such as an antibody) that binds to an epitope on analyte of interest that differs from the epitope on analyte of interest bound by the first specific binding member. Moreover, also preferably, the second specific binding member is labeled with or contains a detectable label (e.g., a detectable label, a tag attached by a cleavable linker, etc.).

The use of immobilized antibodies or fragments thereof may be incorporated into the immunoassay. The antibodies may be immobilized onto a variety of supports, such as magnetic or chromatographic matrix particles, latex particles or modified surface latex particles, polymer or polymer film, plastic or plastic film, planar substrate, a microfluidic surface, pieces of a solid substrate material, and the like.

Sandwich Immunoassay

A sandwich immunoassay measures the amount of antigen between two layers of antibodies (i.e., a capture antibody (i.e., at least one capture antibody) and a detection antibody (i.e. at least one detection antibody)). The capture antibody and the detection antibody bind to different epitopes on the antigen, e.g., analyte of interest. Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte of interest in a sample. More specifically, the at least two antibodies bind to certain epitopes of analyte of interest or an analyte of interest fragment forming an immune complex which is referred to as a "sandwich." One or more antibodies can be used to capture the analyte of interest in the sample (these antibodies are frequently referred to as a "capture" antibody or antibodies), and one or more antibodies with a detectable label (e.g., a fluorescent label, a tag attached by a cleavable linker, etc.) that also bind the analyte of interest (these antibodies are frequently referred to as the "detection" antibody or antibodies) can be used to complete the sandwich. In some embodiments, an aptamer may be used as the second binding member. In a sandwich assay, the binding of an antibody to its epitope desirably is not diminished by the binding of any other antibody in the assay to its respective epitope. In other words, antibodies are selected so that the one or more first antibodies brought into contact with a sample suspected of containing analyte of interest do not bind to all or part of an epitope recognized by the second or subsequent antibodies, thereby interfering with the ability of the one or more second detection antibodies to bind to the analyte of interest.

In one embodiment, a sample suspected of containing analyte of interest can be contacted with at least one capture antibody (or antibodies) and at least one detection antibodies either simultaneously or sequentially. In the sandwich assay format, a sample suspected of containing analyte of interest (such as a membrane-associated analyte of interest, a soluble analyte of interest, fragments of membrane-associated analyte of interest, fragments of soluble analyte of interest, variants of analyte of interest (membrane-associated or soluble analyte of interest) or any combinations thereof)) is first brought into contact with the at least one capture antibody that specifically binds to a particular epitope under conditions which allow the formation of an antibody-analyte of interest complex. If more than one capture antibody is used, a multiple capture antibody-analyte of interest complex is formed. In a sandwich assay, the antibodies, preferably, the at least one capture antibody, are used in molar excess amounts of the maximum amount of analyte of interest or the analyte of interest fragment expected in the sample.

Optionally, prior to contacting the sample with the at least one first capture antibody, the at least one capture antibody can be bound to a solid support which facilitates the separation the antibody-analyte of interest complex from the sample. Any solid support known in the art can be used, including but not limited to, solid supports made out of polymeric materials in the form of planar substrates or beads, and the like. The antibody (or antibodies) can be bound to the solid support by adsorption, by covalent bonding using a chemical coupling agent or by other means known in the art, provided that such binding does not interfere with the ability of the antibody to bind analyte of interest or analyte of interest fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide, azido, alkynyl, and 1-ethyl-3-(3-dimethylaminopropyl)carbodiimide.

After the sample suspected of containing analyte of interest is brought into contact with the at least one capture antibody, the sample is incubated in order to allow for the formation of a capture antibody (or capture antibodies)-analyte of interest complex. The incubation can be carried out at a pH of from about 4.5 to about 10.0, at a temperature of from about 2° C. to about 45° C., and for a period from at least about one minute to about eighteen (18) hours, from about 2-6 minutes, or from about 3-4 minutes.

After formation of the capture antibody (antibodies)-analyte of interest complex, the complex is then contacted with at least one detection antibody (under conditions which allow for the formation of a capture antibody (antibodies)-analyte of interest-detection antibody (antibodies) complex). If the capture antibody-analyte of interest complex is contacted with more than one detection antibody, then a capture antibody (antibodies)-analyte of interest-detection antibody (antibodies) detection complex is formed. As with the capture antibody, when the at least one detection (and subsequent) antibody is brought into contact with the capture antibody-analyte of interest complex, a period of incubation under conditions similar to those described above is required for the formation of the capture antibody (antibodies)-analyte of interest-detection antibody (antibodies) complex. Preferably, at least one detection antibody contains a detectable label (e.g., a fluorescent label, a tag attached by a cleavable linker, etc.). The detectable label can be bound to the at least one detection antibody prior to, simultaneously with or after the formation of the capture antibody (antibodies)-analyte of interest-detection antibody (antibodies) complex. Any detectable label known in the art can be used, e.g., a fluorescent label as discussed herein, and others known in the art.

The order in which the sample and the specific binding member(s) are added to form the mixture for assay is not critical. If the first specific binding member is detectably labeled (e.g., a fluorescent label), then detectably-labeled first specific binding member-analyte of interest complexes form. Alternatively, if a second specific binding member is used and the second specific binding member is detectably labeled (e.g., a fluorescent label), then detectably-labeled complexes of first specific binding member-analyte of interest-second specific binding member form. Any unbound specific binding member, whether labeled or unlabeled, can be removed from the mixture using any technique known in the art, such as washing.

Next, signal indicative of the presence of analyte of interest or a fragment thereof is generated. Based on the parameters of the signal generated, the amount of analyte of interest in the sample can be quantified. Optionally, a standard curve can be generated using serial dilutions or solutions of known concentrations of analyte of interest by mass spectroscopy, gravimetric methods, and other techniques known in the art.

Forward Competitive Inhibition

In a forward competitive format, an aliquot of labeled analyte of interest (e.g., analyte having a fluorescent label) of a known concentration is used to compete with analyte of interest in a sample for binding to analyte of interest antibody.

In a forward competition assay, an immobilized specific binding member (such as an antibody) can either be sequentially or simultaneously contacted with the sample and a labeled analyte of interest, analyte of interest fragment, or analyte of interest variant thereof. The analyte of interest, analyte of interest fragment, or analyte of interest variant can be labeled with any detectable label, including a detectable label comprised of tag attached with a cleavable linker. In this assay, the antibody can be immobilized on to a solid support. Alternatively, the antibody can be coupled to another antibody, such as an antispecies antibody, that has been immobilized on a solid support, such as a microparticle or planar substrate.

Reverse Competition Assay

In a reverse competition assay, an immobilized analyte of interest can either be sequentially or simultaneously contacted with a sample and at least one labeled antibody. The analyte of interest can be bound to a solid support, such as the solid supports discussed above in connection with the sandwich assay format.

One-Step Immunoassay or "Capture on the Fly"

In a capture on the fly immunoassay, a solid substrate is pre-coated with an immobilization agent. The capture agent, the analyte, and the detection agent are added to the solid substrate together, followed by a wash step prior to detection. The capture agent can bind the analyte and comprises a ligand for an immobilization agent. The capture agent and the detection agents may be antibodies or any other moiety capable of capture or detection as described herein or known in the art. The ligand may comprise a peptide tag and an immobilization agent may comprise an anti-peptide tag antibody. Alternately, the ligand and the immobilization agent may be any pair of agents capable of binding together so as to be employed for a capture on the fly assay (e.g., specific binding pair, and others such as are known in the art). More than one analyte may be measured. In some embodiments, the solid substrate may be coated with an antigen and the analyte to be analyzed is an antibody.

In certain other embodiments, in a one-step immunoassay or "capture on the fly", a solid support (such as a microparticle) pre-coated with an immobilization agent (such as biotin, streptavidin, etc.) and at least a first specific binding member and a second specific binding member (which function as capture and detection reagents, respectively) are used. The first specific binding member comprises a ligand for the immobilization agent (for example, if the immobilization agent on the solid support is streptavidin, the ligand on the first specific binding member may be biotin) and also binds to the analyte of interest. The second specific binding member comprises a detectable label and binds to an analyte of interest. The solid support and the first and second specific binding members may be added to a sample (either sequentially or simultaneously). The ligand on the first specific binding member binds to the immobilization agent on the solid support to form a solid support/first specific binding member complex. Any analyte of interest present in the sample binds to the solid support/first specific binding member complex to form a solid support/first specific binding member/analyte complex. The second specific binding member binds to the solid support/first specific binding member/analyte complex and the detectable label is detected. An optional wash step may be employed before the detection. In certain embodiments, in a one-step assay more than one analyte may be measured. In certain other embodiments, more than two specific binding members can be employed. In certain other embodiments, multiple detectable labels can be added. In certain other embodiments, multiple analytes of interest can be detected.

A capture on the fly assay can be performed in a variety of formats as described herein and known in the art. For example, the format can be a sandwich assay such as described above, but alternately can be a competition assay, can employ a single specific binding member, or use other known variations.

Combination Assays

In a combination assay, a solid substrate, such as a microparticle, is co-coated with an antigen and an antibody to capture an antibody and an antigen from a sample, respectively. The solid support may be co-coated with two or more different antigens to capture two or more different antibodies from a sample. The solid support may be co-coated with two or more different antibodies to capture two or more different antigens from a sample.

Additionally, the methods described herein may use blocking agents to prevent either specific or non-specific binding reactions (e.g., HAMA concern) among assay compounds. Once the agent (and optionally, any controls) is immobilized on the support, the remaining binding sites of the agent may be blocked on the support. Any suitable blocking reagent known to those of ordinary skill in the art may be used. For example, bovine serum albumin ("BSA"), phosphate buffered saline ("PBS") solutions of casein in PBS, Tween 20™ (Sigma Chemical Company, St. Louis, Mo.), or other suitable surfactant, as well as other blocking reagents, may be employed.

As is apparent from the present disclosure, the methods disclosed herein, including variations, may be used for diagnosing a disease, disorder or condition in a subject suspected of having the disease, disorder, or condition. For example, the sample analysis may be useful for detecting a disease marker, such as, a cancer marker, a marker for a cardiac condition, a toxin, a pathogen, such as, a virus, a bacterium, or a portion thereof. The methods also may be used for measuring an analyte present in a biological sample. The methods also may be used in blood screening assays to detect a target analyte. The blood screening assays may be used to screen a blood supply.

Device for Analyte Analysis

The methods described herein can be performed using any device suitable for analyte analysis, a variety of which are known in the art and include, for example, peristaltic pump systems (e.g., FISHERBRAND™ Variable-Flow Peristaltic Pumps, ThermoFisher Scientific, Waltham, MA; and peristaltic pump systems available from MilliporeSigma, Burlington, MA), automated/robotic sample delivery systems (commercially available from e.g., Hamilton Robotics, Reno, NV; and ThermoFisher Scientific, Waltham, MA), microfluidics devices, droplet based microfluidic devices, digital microfluidics devices (DMF), surface acoustic wave based microfluidic (SAW) devices, or electrowetting on dielectric (EWOD) digital microfluidics devices (see, e.g., Peng et al., *Lab Chip,* 14(6): 1117-1122 (2014); and Huang et al., *PLoS ONE,* 10(5): e0124196 (2015)), and other automated systems such as KINGFISHER™ instruments (ThermoFisher Scientific, Waltham, MA), ARCHITECT™ analyzers (Abbott, Abbott Park, IL), and other automated instruments known in the art.

In one embodiment, the methods described herein may be performed using a microfluidics device, such as a digital microfluidic (DMF) device. Any suitable microfluidics device known in the art can be used to perform the methods described herein, such as those described in, for example, International Patent Application Publication Nos. WO 2007/136386, WO 2009/111431, WO 2010/040227, WO 2011/137533, WO 2013/066441, WO 2014/062551, and WO 2014/066704, and U.S. Pat. No. 8,287,808. In certain cases, the device may be a lab-on-chip device, where analyte analysis may be carried out in a droplet of the sample containing or suspected of containing an analyte.

In one embodiment, at least two steps of the methods described herein (e.g., 2, 3, or all steps) are carried out in a digital microfluidics device. The terms "digital microfluidics (DMF)," "digital microfluidic module (DMF module)," or "digital microfluidic device (DMF device)" are used interchangeably herein and refer to a module or device that utilizes digital or droplet-based microfluidic techniques to provide for manipulation of discrete and small volumes of liquids in the form of droplets. Digital microfluidics uses the principles of emulsion science to create fluid-fluid dispersion into channels (principally water-in-oil emulsion) and allows for the production of monodisperse drops/bubbles with a very low polydispersity. Digital microfluidics is based upon the micromanipulation of discontinuous fluid droplets within a reconfigurable network. Complex instructions can be programmed by combining the basic operations of droplet formation, translocation, splitting, and merging.

Digital microfluidics operates on discrete volumes of fluids that can be manipulated by binary electrical signals. By using discrete unit-volume droplets, a microfluidic operation may be defined as a set of repeated basic operations, i.e., moving one unit of fluid over one unit of distance. Droplets may be formed using surface tension properties of the liquid. Actuation of a droplet is based on the presence of electrostatic forces generated by electrodes placed beneath the bottom surface on which the droplet is located. Different types of electrostatic forces can be used to control the shape and motion of the droplets. One technique that can be used to create the foregoing electrostatic forces is based on dielectrophoresis which relies on the difference of electrical permittivities between the droplet and surrounding medium and may utilize high-frequency AC electric fields. Another technique that can be used to create the foregoing electrostatic forces is based on electrowetting, which relies on the dependence of surface tension between a liquid droplet present on a surface and the surface on the electric field applied to the surface.

In another embodiment, the methods described herein may be implemented in conjunction with a surface acoustic wave (SAW) based microfluidic device as a front-end assay processing method. The term "surface acoustic wave (SAW)," as used herein, refers generally to propagating acoustic waves in a direction along a surface. "Travelling surface acoustic waves" (TSAWs) enable coupling of surface acoustic waves into a liquid. In some embodiments, the coupling may be in the form of penetration or leaking of the surface acoustic waves into the liquid. In other embodiments, the surface acoustic waves are Rayleigh waves (see, e.g., Oliner, A. A.(ed), Acoustic Surface Waves. Springer (1978)). Propagation of surface acoustic waves may be conducted in a variety of different ways and by using different materials, including generating an electrical potential by a transducer, such as a series or plurality of electrodes, or by streaming the surface acoustic waves through a liquid.

In some embodiments, the DMF device or the SAW device is fabricated by roll to roll based printed electronics method. Examples of such devices are described in International Patent Application Publication Nos. WO 2016/161402 and WO 2016/161400.

Many of the devices described above allow for the detection of a single molecule of an analyte of interest. Other devices and systems known in the art that allow for single molecule detection of one or more analytes of interest also can be used in the methods described herein. Such devices and systems include, for example, Quanterix SIMOA™ (Lexington, MA) technology, Singulex's single molecule counting (SMC™) technology (Alameda, CA, see for example, U.S. Pat. No. 9,239,284), and devices described in, for example, U.S. Patent Application Publication Nos. 2017/0153248 and 2018/0017552.

Kits and Cartridges

Also provided herein is a kit for use in performing the above-described methods. The kit may be used with any of the devices described above. Instructions included in the kit may be affixed to packaging material or may be included as a package insert. The instructions may be written or printed materials but are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The kit may include a cartridge that includes a microfluidics module. In some embodiments, the microfluidics module may be integrated in a cartridge. The cartridge may be disposable. The cartridge may include one or more reagents useful for practicing the methods disclosed above. The cartridge may include one or more containers holding the reagents, as one or more separate compositions, or, optionally, as admixture where the compatibility of the reagents will allow. The cartridge may also include other material(s) that may be desirable from a user standpoint, such as buffer(s), a diluent(s), a standard(s) (e.g., calibrators and controls), and/or any other material useful in sample processing, washing, or conducting any other step of the assay. The cartridge may include one or more specific binding members as described above.

The kit may further comprise reference standards for quantifying the analyte of interest. The reference standards may be employed to establish standard curves for interpolation and/or extrapolation of the analyte of interest concentrations. The kit may include reference standards that vary in terms of concentration level. For example, the kit may include one or more reference standards with either a high concentration level, a medium concentration level, or a low concentration level. In terms of ranges of concentrations for the reference standard, this can be optimized per the assay.

Exemplary concentration ranges for the reference standards include but are not limited to, for example: about 10 fg/mL, about 20 fg/mL, about 50 fg/mL, about 75 fg/mL, about 100 fg/mL, about 150 fg/mL, about 200 fg/mL, about 250 fg/mL, about 500 fg/mL, about 750 fg/mL, about 1000 fg/mL, about 10 μg/mL, about 20 μg/mL, about 50 μg/mL, about 75 μg/mL, about 100 μg/mL, about 150 μg/mL, about 200 μg/mL, about 250 μg/mL, about 500 μg/mL, about 750 μg/mL, about 1 ng/mL, about 5 ng/mL, about 10 ng/mL, about 12.5 ng/mL, about 15 ng/mL, about 20 ng/mL, about 25 ng/mL, about 40 ng/mL, about 45 ng/mL, about 50 ng/mL, about 55 ng/mL, about 60 ng/mL, about 75 ng/mL, about 80 ng/mL, about 85 ng/mL, about 90 ng/mL, about 95 ng/mL, about 100 ng/mL, about 125 ng/mL, about 150 ng/mL, about 165 ng/mL, about 175 ng/mL, about 200 ng/mL, about 225 ng/mL, about 250 ng/mL, about 275 ng/mL, about 300 ng/mL, about 400 ng/mL, about 425 ng/mL, about 450 ng/mL, about 465 ng/mL, about 475 ng/mL, about 500 ng/mL, about 525 ng/mL, about 550 ng/mL, about 575 ng/mL, about 600 ng/mL, about 700 ng/mL, about 725 ng/mL, about 750 ng/mL, about 765 ng/mL, about 775 ng/mL, about 800 ng/mL, about 825 ng/mL, about 850 ng/mL, about 875 ng/mL, about 900 ng/mL, about 925 ng/mL, about 950 ng/mL, about 975 ng/mL, about 1000 ng/mL, about 2 μg/mL, about 3 μg/mL, about 4 μg/mL, about 5 μg/mL, about 6 μg/mL, about 7 μg/mL, about 8 μg/mL, about 9 μg/mL, about 10 μg/mL, about 20 μg/mL, about 30 μg/mL, about 40 μg/mL, about 50 μg/mL, about 60 μg/mL, about 70 μg/mL, about 80 μg/mL, about 90 μg/mL, about 100 μg/mL, about 200 μg/mL, about 300 μg/mL, about 400 μg/mL, about 500 μg/mL, about 600 μg/mL, about 700 μg/mL, about 800 μg/mL, about 900 μg/mL, about 1000 μg/mL, about 2000 μg/mL, about 3000 μg/mL, about 4000 μg/mL, about 5000 μg/mL, about 6000 μg/mL, about 7000 μg/mL, about 8000 μg/mL, about 9000 μg/mL, or about 10000 μg/mL.

The kit may include reagents for labeling the specific binding members, reagents for detecting the specific binding members and/or for labeling the analytes, and/or reagents for detecting the analyte. The kit may also include components to elicit cleavage of a tag, such as a cleavage mediated reagent. For example, a cleavage mediate reagent may include a reducing agent, such as dithiothreitol (DTT) or tris(2-carboxyethyl)phosphine) TCEP. The specific binding members, calibrators, and/or controls can be provided in separate containers or pre-dispensed into an appropriate assay format or cartridge.

The kit may also include quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics and are useful indicators of the integrity of the kit reagents and the standardization of assays.

The kit may also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit may additionally include one or more other controls. One or more of the components of the kit can be lyophilized, in which case the kit can further comprise reagents suitable for the reconstitution of the lyophilized components. One or more of the components may be in liquid form.

The various components of the kit optionally are provided in suitable containers as necessary. The kit further can include containers for holding or storing a sample (e.g., a container or cartridge for a urine, saliva, plasma, cerebrospinal fluid, or serum sample, or appropriate container for storing, transporting or processing tissue so as to create a tissue aspirate). Where appropriate, the kit optionally can contain reaction vessels, mixing vessels, and other components that facilitate the preparation of reagents or the test sample. The kit can also include one or more sample collection/acquisition instruments for assisting with obtaining a test sample, such as various blood collection/transfer devices (e.g., microsampling devices, micro-needles, or other minimally invasive pain-free blood collection methods; blood collection tube(s); lancets; capillary blood collection tubes; other single fingertip-prick blood collection methods; buccal swabs, nasal/throat swabs; 16-gauge or other size needle, circular blade for punch biopsy (e.g., 1-8 mm, or other appropriate size), surgical knife or laser (e.g., particularly hand-held), syringes, sterile container, or canula, for obtaining, storing or aspirating tissue samples; or the like). The kit can include one or more instruments for assisting with joint aspiration, cone biopsies, punch biopsies, fine-needle aspiration biopsies, image-guided percutaneous needle aspiration biopsy, bronchoaveolar lavage, endoscopic biopsies, and laproscopic biopsies.

EXAMPLES

The following examples further illustrate the invention but, of course, should not be construed as in any way limiting its scope.

Reagents used in the following examples were purchased from commercial sources and used as received unless otherwise indicated.

Example 1

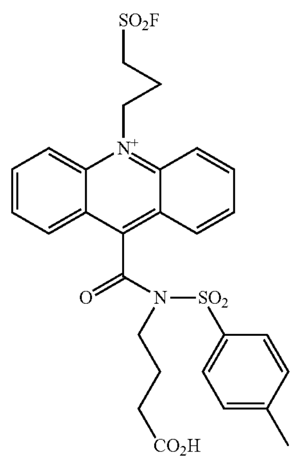 [SMILES: Cc1ccc(S(=O)(=O)N(CCCC(=O)O)C(=O)c2c3ccccc3[n+](CCCS(=O)(=O)F)c3ccccc23)cc1]

1.0 g (1.7 mmoles) of CPSP-acridinium (*J. Org. Chem.* 1998, 63, 5636-5639) was treated with 2 mL of $[COCl]_2$ (23 mmoles) in 25 mL of methylene chloride (DCM) followed by the addition of 5 μL of dimethylformamide. The slurry was stirred for 2 hours at room temperature and a yellow solution was obtained. After this time, the volatile components were removed from the reaction in vacuo on a rotary evaporator to give the di-acid chloride as a yellow gummy foam. The residue was re-dissolved in DCM (25 mL). A saturated aqueous solution of potassium bifluoride was prepared (15 mL) and added to the DCM solution. The two-phase system was stirred vigorously for 2 hours. After this time, the upper aqueous phase of the reaction was removed with a pipette and the lower DCM layer was evaporated in vacuo on a rotary evaporator. The resulting yellow solid was suspended in water (~25 mL) and filtered through a Buchner funnel. The solid was washed with small portions of cold water ~(65 mL). Yield 1.08 g of a yellow solid. MS (M+): calculated for $C_{28}H_{28}FN_2O_7S_2$+: Exact Mass: 587.13; Molecular Weight: 587.66. UPLC/MS measured 587.39.

Example 2

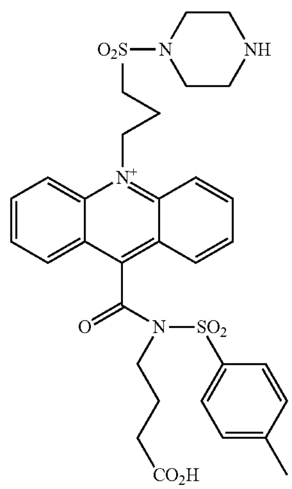 [SMILES: Cc1ccc(S(=O)(=O)N(CCCC(=O)O)C(=O)c2c3ccccc3[n+](CCCS(=O)(=O)N3CCNCC3)c3ccccc23)cc1]

A 25 mL round bottom flask equipped with a magnetic stir bar and nitrogen inlet was charged with 0.1 g (0.17 mmol) of the product from Example 1, DCM (10 mL) and then 0.14 g (1.7 mmol) of piperazine was added to the yellow slurry in one portion which resulted in a clear solution. The reaction was stirred for 5.5 days at room temperature. After this time, a milky white slurry was obtained. The reaction was evaporated to dryness in vacuo and the solids were dissolved in water (5 mL), methanol (5 mL) and 1 N HCl (2 mL). The resulting solution was purified by reverse phase HPLC using a YMC ODS AQ 50×250 mm I.D. steel column with a Waters Separations 2000 system monitored at 254 nm. Recorder chart speed 5 mm/min. A manual step gradient method (flow rate 70 mL/min) was used ACN/$H_2O$/$H_2O$-0.5 TFA. Fractions containing the product were combined and the volatile components were removed in vacuo on a rotary evaporator at 30° C. followed by high vacuum for 18 hours at room temperature. Yield 0.163 g of a yellow glass (titled compound as TFA salt). MS (M+): calculated for $C_{32}H_{37}N_4O_7S_2$+: Exact Mass: 653.21; Molecular Weight: 653.79. UPLC/MS measured 653.33.

Example 3

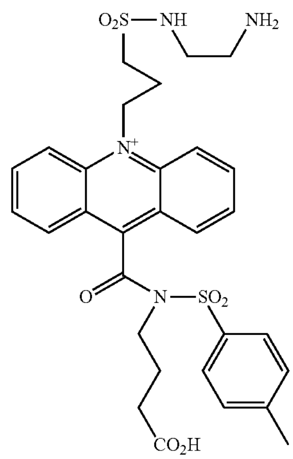 [SMILES: Cc1ccc(S(=O)(=O)N(CCCC(=O)O)C(=O)c2c3ccccc3[n+](CCCS(=O)(=O)NCCN)c3ccccc23)cc1]

The titled compound was prepared using the same procedure outlined for the preparation of Example 2 utilizing 0.1 g (0.17 mmol) of the product from Example 1, DCM (5 mL) and 0.057 mL (0.85 mmol) of ethylene diamine (EDA). Yield 0.027 g of a yellow film (titled compound as TFA salt). MS (M+): calculated for $C_{30}H_{35}N_4O_7S_2$+: Exact Mass: 627.1942; Molecular Weight: 627.7510. UPLC/MS measured 627.43.

Example 4

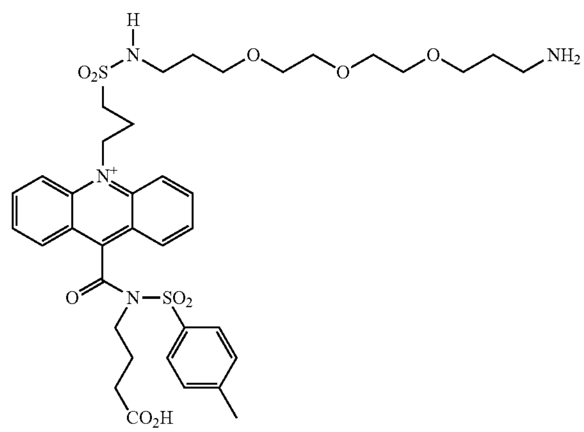 [SMILES: Cc1ccc(S(=O)(=O)N(CCCC(=O)O)C(=O)c2c3ccccc3[n+](CCCS(=O)(=O)NCCCOCCOCCOCCCN)c3ccccc23)cc1]

The titled compound was prepared using the same procedure outlined for the preparation of Example 2 utilizing 0.026 g (0.044 mmol) of the product from Example 1, DCM (5 mL) and 0.1 mL (0.45 mmol) of 4,7,10-trioxa-1,13-tridecanediamine. Yield 0.018 g of a yellow film (titled compound as TFA salt). MS (M+): calculated for $C_{38}H_{51}N_4O_{10}S_2$+: Exact Mass: 787.3041; Molecular Weight: 787.9618. UPLC/MS measured 787.53.

Example 5

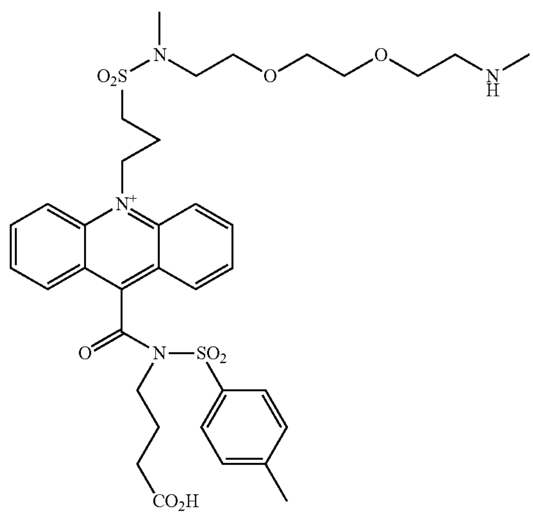 [SMILES: CNCCOCCOCCN(C)S(=O)(=O)CCC[n+]1c2ccccc2c(C(=O)N(CCCC(=O)O)S(=O)(=O)c2ccc(C)cc2)c2ccccc21]

The titled compound was prepared using the same procedure outlined for the preparation of Example 2 utilizing 0.03 g (0.051 mmol) of the product from Example 1, DCM (1 mL) and 0.1 g (0.57 mmol) of 1,8-bis(methylamino)-3,6-dioxaoctane. Yield 0.016 g of a yellow film (titled compound as TFA salt). MS (M+): calculated for $C_{36}H_{47}N_4O_9S_2$+: Exact Mass: 743.2779; Molecular Weight: 743.9092. UPLC/MS measured 743.39.

Example 6

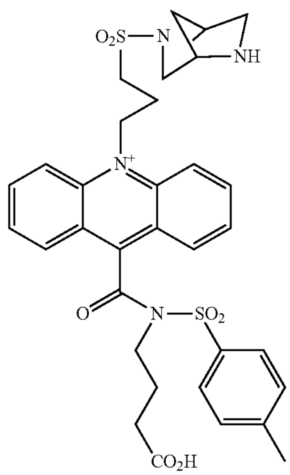 [SMILES: Cc1ccc(S(=O)(=O)N(CCCC(=O)O)C(=O)c2c3ccccc3[n+](CCCS(=O)(=O)NCC3CC(C)CN3)c3ccccc23)cc1]

A 5 mL round bottom flask equipped with a magnetic stir bar and nitrogen inlet was charged with 0.015 g (0.026 mmol) of the product from Example 1, DMF (1 mL), N,N-diisopropylethylamine (DIEA) (0.34 mL, 2 mmol) and then (1S,4S)-(+)-2,5-diazabicyclo[2.2.1]heptane dihydrobromide (0.14 g, 0.52 mmol) was added in one portion. The reaction was stirred for 2 days at room temperature. The entire solution was purified by reverse phase HPLC using a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5 TFA. Fractions containing the product were combined and the volatile components were removed in vacuo on a rotary evaporator at 30° C. followed by high vacuum for 18 hours at room temperature. Yield 0.0084 g of a yellow film (titled compound as TFA salt). MS (M+): calculated for $C_{33}H_{37}N_4O_7S_2$+: Exact Mass: 665.2098; Molecular Weight: 665.7989. UPLC/MS measured 665.20.

Example 7

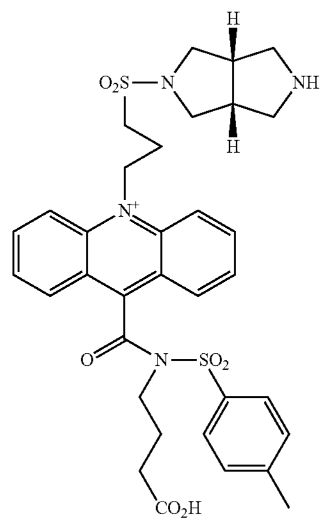 [SMILES: Cc1ccc(S(=O)(=O)N(CCCC(=O)O)C(=O)c2c3ccccc3[n+](CCCS(=O)(=O)N3C[C@H]4CNC[C@H]4C3)c3ccccc23)cc1]

A 5 mL round bottom flask equipped with a magnetic stir bar and nitrogen inlet was charged with 0.015 g (0.026 mmol) of the product from Example 1, DCM (0.5 mL), DIEA (0.17 mL, 1 mmol) and then (cis-racemic0-tert-butyl hexahydropyrrolo[3,4-c]pyrrole-2(1H)-carboxylate (0.055 g, 0.26 mmol) was added to the yellow slurry in one portion. The reaction was stirred for 18 hours at room temperature. The reaction was evaporated to dryness using a stream of nitrogen and then dissolved in a small amount of MeOH. The entire solution was purified by reverse phase HPLC using a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5 formic acid. Fractions containing the product were combined and the volatile components were removed in vacuo on a rotary evaporator at 30° C. followed by high vacuum for 18 hours at room temperature. Yield 0.0205 g of a yellow film (Boc protected amine intermediate). MS (M+): calculated for $C_{39}H_{47}N_4O_9S_2$+: Exact Mass: 779.2779; Molecular Weight: 779.9413. UPLC/MS measured 779.16.

A 4 mL vial equipped with a magnetic stir bar was charged with the Boc-protected amine intermediate and DCM (0.5 mL). Trifluoroacetic acid (TFA) (0.5 mL) was added and the mixture was stirred for 1 hour at RT. The reaction was evaporated to dryness using a stream of nitrogen overnight. The crude product was dissolved in a small amount of MeOH. The entire solution was purified by reverse phase HPLC using a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5 TFA. Fractions containing the product were combined and the volatile components were removed in vacuo on a rotary evaporator at 30° C. followed by high vacuum for 18 hours at room temperature. Yield 0.0175 g of a yellow film (titled compound as TFA salt). MS (M+): calculated for $C_{34}H_{39}N_4O_7S_2$+: Exact Mass: 679.2255; Molecular Weight: 679.8255. UPLC/MS measured 679.24.

Example 8

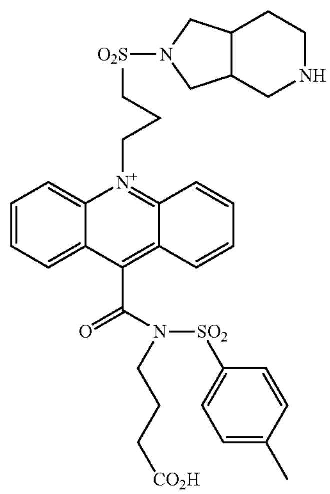 [SMILES: Cc1ccc(S(=O)(=O)N(CCCC(=O)O)C(=O)c2c3ccccc3[n+](CCCS(=O)(=O)N3CC4CCNCC4C3)c3ccccc23)cc1]

The titled compound was prepared using the same procedure outlined for the preparation of Example 7 utilizing 0.015 g (0.026 mmol) of the product from Example 1, 5-Boc-octahydro-pyrrolo[3,4-c]pyridine (0.01 g, 0.044 mmol), DCM (0.5 mL for the amine coupling and 0.5 mL for the de-protection step), DIEA (for amine coupling, 0.17 mL, 1 mmol), and TFA (for Boc deprotection, 0.5 mL). Yield 0.0074 g of a yellow film (Boc protected amine intermediate). MS (M+): calculated for $C_{40}H_{49}N_4O_9S_2$+: Exact Mass: 793.2935; Molecular Weight: 793.9679. UPLC/MS measured 793.20.

Yield 0.0077 g of a yellow film (titled compound as TFA salt). MS (M+): calculated for $C_{35}H_{41}N_4O_7S_2$+: Exact Mass: 693.2411; Molecular Weight: 693.8521. UPLC/MS measured 693.20.

Example 9

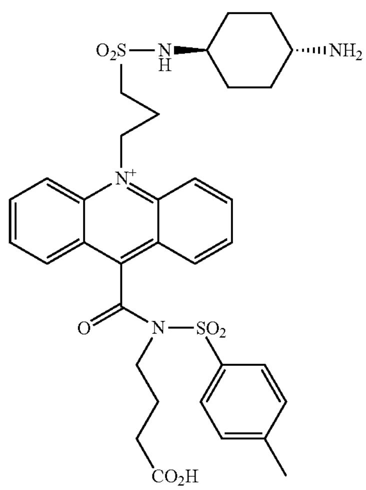 [SMILES: Cc1ccc(S(=O)(=O)N(CCCC(=O)O)C(=O)c2c3ccccc3[n+](CCCS(=O)(=O)N[C@H]3CC[C@H](N)CC3)c3ccccc23)cc1]

A 5 mL round bottom flask equipped with a magnetic stir bar and nitrogen inlet was charged with 0.015 g (0.026 mmol) of the product from Example 1, DCM (0.5 mL) and DIEA (0.17 mL, 1 mmol). trans-1,2-diaminocyclohexane was added to the yellow slurry in one portion. The reaction was stirred for 18 hours at room temperature. The reaction was evaporated to dryness using a stream of nitrogen and then dissolved in a small amount of MeOH. The entire solution was purified by reverse phase HPLC using a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield 0.010 g of a yellow film (titled compound as TFA salt). MS (M+): calculated for $C_{34}H_{41}N_4O_7S_2$+: Exact Mass: 681.2411; Molecular Weight: 681.8414. UPLC/MS measured 681.27.

Example 10

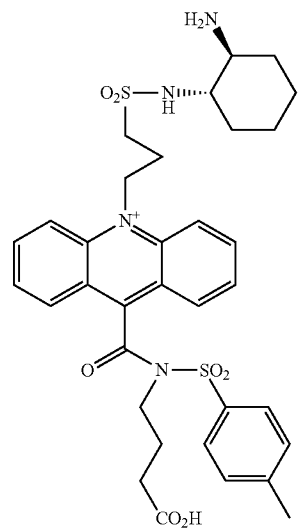 [SMILES: Cc1ccc(S(=O)(=O)N(CCCC(=O)O)C(=O)c2c3ccccc3[n+](CCCS(=O)(=O)N[C@H]3CCCC[C@@H]3N)c3ccccc23)cc1]

The titled compound was prepared using the same procedure outlined for the preparation of Example 9 utilizing 0.015 g (0.026 mmol) of the product from Example 1, DCM (0.5 mL), DIEA (0.17 mL, 1 mmol) and (+−)-trans-1,2-diaminocyclohexane (0.029 g, 0.26 mmol). Yield 0.0154 g of a yellow film (titled compound as TFA salt). MS (M+): calculated for $C_{34}H_{41}N_4O_7S_2$+: Exact Mass: 681.2411; Molecular Weight: 681.8414. UPLC/MS measured 681.34.

Example 11

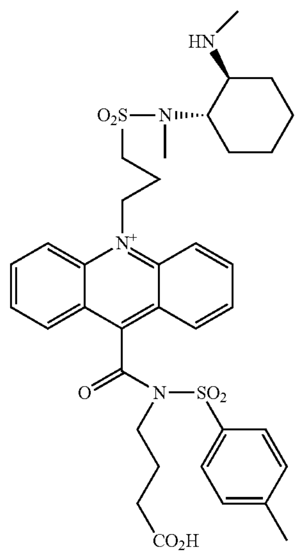 [SMILES: CN[C@H]1CCCC[C@@H]1N(C)S(=O)(=O)CCC[n+]1c2ccccc2c(C(=O)N(CCCC(=O)O)S(=O)(=O)c2ccc(C)cc2)c2ccccc21]

The titled compound was prepared using the same procedure outlined for the preparation of Example 9 utilizing 0.015 g (0.026 mmol) of the product from Example 1, DCM (0.5 mL), DIEA (0.17 mL, 1 mmol) and (S,S)-(+)-n,N'-dimethyl-1,2-cyclohexanediamine (0.037 g, 0.26 mmol). Yield 0.0056 g of a yellow film (titled compound as TFA salt). MS (M+): calculated for $C_{36}H_{45}N_4O_7S_2$+: Exact Mass: 709.2724; Molecular Weight: 709.8946. UPLC/MS measured 709.27.

Example 12

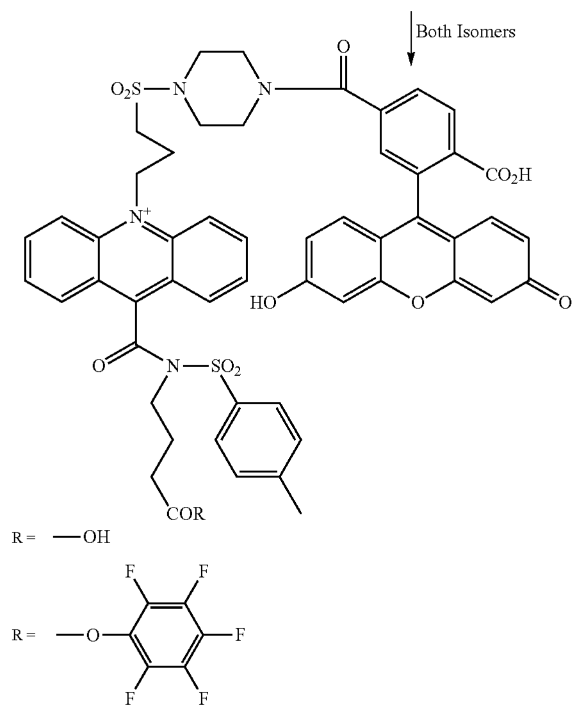

-continued

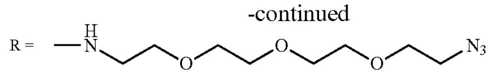

A 5 mL round bottom flask equipped with a magnetic stir bar and nitrogen inlet was charged with 0.005 g (0.0065 mmol) of the product from Example 2, DMF (0.5 mL) and 0.01 g (0.021 mmol) of a mixture of (5)6-carboxyfluorescein-NHS esters followed by the addition of DIEA (0.05 mL, 0.28 mmol). The reaction was stirred at room temperature for 2.5 days. A few drops of water were added and the mixture was stirred at room temperature for 30 minutes. The reaction was diluted with MeOH (2 mL) and purified by reverse phase HPLC using a YMC ODS AQ 30×150 mm steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5 TFA. The fractions containing the products were combined and volatile components were removed in vacuo on a rotary evaporator at 30° C. and dried under high vacuum (1 mm Hg) over 2 hours. Yield 0.0012 g of a yellow film (titled compound). MS (M+): calculated for $C_{53}H_{47}N_4O_{13}S_2$+: Exact Mass: 1011.2576; Molecular Weight: 1012.0887. UPLC/MS measured 1011.39.

A 5 mL round bottom flask equipped with a magnetic stir bar and nitrogen inlet was charged with 0.012 g of the product from the above step, DMF (0.5 mL) and Pyridine ((0.5 mL, 0.62 mmol). Pentafluorophenyl trifluoroacetate (0.05 mL, 0.3 mmol) was then added to the mixture in one portion and the reaction was stirred at RT for 1 hr. The volatile components were removed from the mixture in vacuo and the residue was triturated 5× with 1:1 ether-hexane and the trace volatile components were removed under high vacuum (1 mm Hg) over 2 hours. Yield 0.008 g of a yellow film (titled compound, R=—O-pentafluorophenyl). MS (M+): calculated for $C_{59}H_{46}F_5N_4O_{13}S_2$+: Exact Mass: 1177.2417; Molecular Weight: 1178.1370. UPLC/MS measured 1177.21. The product was split into 2 equal portions for the next reaction and for conjugation.

0.004 g of the pentafluorophenyl ester product from the last step was dissolved in DCM (0.5 mL). Azido-dPEG3-amine (0.1 g, 0.45 mmol) in DCM (0.5 mL) was then added dropwise and the reaction mixture was stirred for one hour at RT. The volatile components were removed from the reaction mixture under a stream of nitrogen over 18 hours. The reaction mixture was diluted with MeOH (1 mL) and water (1 mL) and purified by reverse phase HPLC by elution on a YMC ODS AQ 30×150 mm steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% TFA. Fractions containing the product were combined and the volatile components were removed in vacuo on a rotary evaporator at 30° C. and dried under high vacuum (1 mm Hg) over 18 hours. Yield 0.007 g yellow film (titled compound, R=—O-PEG-Azide). MS (M+): calculated for $C_{61}H_{63}N8O_{15}S_2$+: Exact Mass: 1211.3849; Molecular Weight: 1212.3270. UPLC/MS measured 1211.47.

Example 13

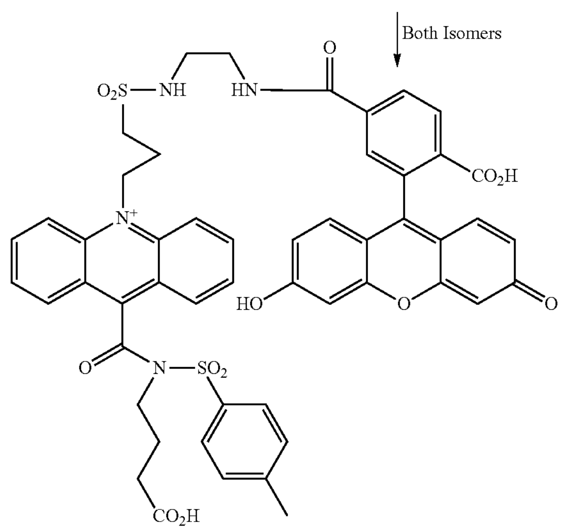 [SMILES: Cc1ccc(S(=O)(=O)N(CCCC(=O)O)C(=O)c2c3ccccc3[n+](CCCS(=O)(=O)NCCNC(=O)c3ccc(C(=O)O)c(-c4c5ccc(=O)cc-5oc5cc(O)ccc45)c3)c3ccccc23)cc1]

The titled compound was prepared using the same procedure outlined for the preparation of Example 12 utilizing 0.039 g (0.049 mmol) of the product from Example 3, DMF (2.0 mL), 0.028 g (0.06 mmol) of a mixture of (5)6-carboxyfluorescein-NHS esters and DIEA (0.1 mL, 0.6 mmol). Yield 0.008 g of a yellow film (titled compound). MS (M+): calculated for $C_{51}H_{45}N_4O_{13}S_2$+: Exact Mass: 985.2419; Molecular Weight: 986.0515. UPLC/MS measured 985.49.

Example 14

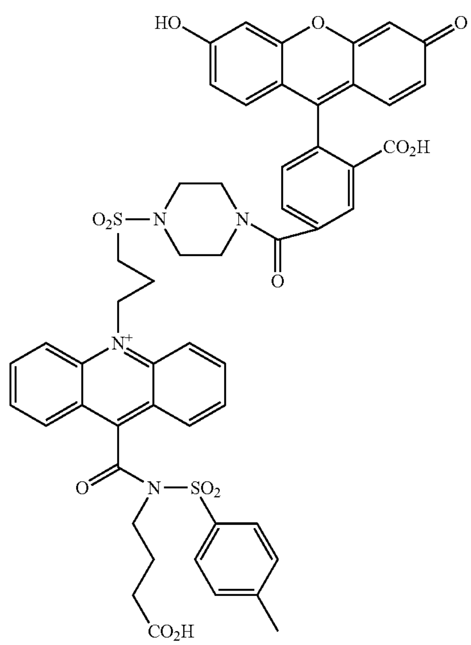 [SMILES: Cc1ccc(S(=O)(=O)N(CCCC(=O)O)C(=O)c2c3ccccc3[n+](CCCS(=O)(=O)N3CCN(C(=O)c4ccc(-c5c6ccc(=O)cc-6oc6cc(O)ccc56)c(C(=O)O)c4)CC3)c3ccccc23)cc1]

The titled compound was prepared using the same procedure outlined for the preparation of Example 12 utilizing 0.01 g (0.013 mmol) of the product from Example 2, DMF (0.25 mL), 0.03 g (0.055 mmol) of 5-carboxyfluorescein-PFP ester (from 5-carboxyfluorescein and pentafluorophenyl trifluoroacetate) and DIEA (0.025 mL, 0.055 mmol). Yield 0.0018 g of a yellow film (titled compound). MS (M+): calculated for $C_{53}H_{47}N_4O_{13}S_2$+: Exact Mass: 1011.2576; Molecular Weight: 1012.0887. UPLC/MS measured 1011.38.

Example 15

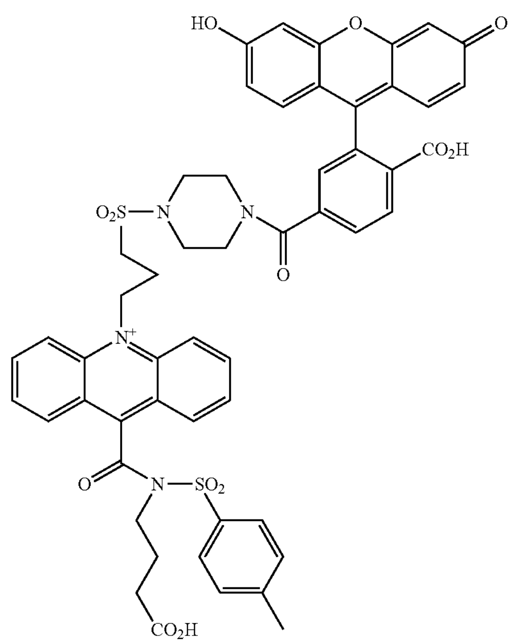 [SMILES: Cc1ccc(S(=O)(=O)N(CCCC(=O)O)C(=O)c2c3ccccc3[n+](CCCS(=O)(=O)N3CCN(C(=O)c4ccc(C(=O)O)c(-c5c6ccc(=O)cc-6oc6cc(O)ccc56)c4)CC3)c3ccccc23)cc1]

The titled compound was prepared using the same procedure outlined for the preparation of Example 12 utilizing 0.01 g (0.013 mmol) of the product from Example 2, DMF (0.25 mL), 0.03 g (0.055 mmol) of 6-carboxyfluorescein-PFP ester (from 6-carboxyfluorescein and pentafluorophenyl trifluoroacetate) and DIEA (0.025 mL, 0.055 mmol). Yield 0.0029 g of a yellow film (titled compound). MS (M+): calculated for $C_{53}H_{47}N_4O_{13}S_2$+: Exact Mass: 1011.2576; Molecular Weight: 1012.0887. UPLC/MS measured 1011.45.

Example 16

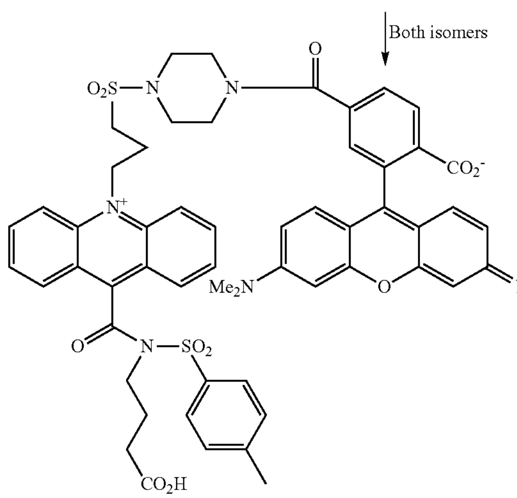

The titled compound was prepared using the same procedure outlined for the preparation of Example 12 utilizing 0.01 g (0.013 mmol) of the product from Example 2, DMF (0.25 mL), 0.011 g (0.021 mmol) of a mixture of (5)6-TAMRA™-NHS esters and DIEA (0.025 mL, 0.055 mmol). Individual product isomers were separated during purification. Yield isomer A from fraction 9: 0.002 g purple film (titled compound). MS (M+): calculated for $C_{57}H_{57}N_6O_{11}S_2$+: Exact Mass: 1065.3521; Molecular Weight: 1066.2255. UPLC/MS measured 1065.55 (weak); M++533.45 (strong).

Yield isomer B from fraction 10: 0.002 g purple film (titled compound). MS (M+): calculated for $C_{57}H_{57}N_6O_{11}S_2$+: Exact Mass: 1065.3521; Molecular Weight: 1066.2255. UPLC/MS measured 1065.48 (weak); M++533.45 (strong).

Example 17

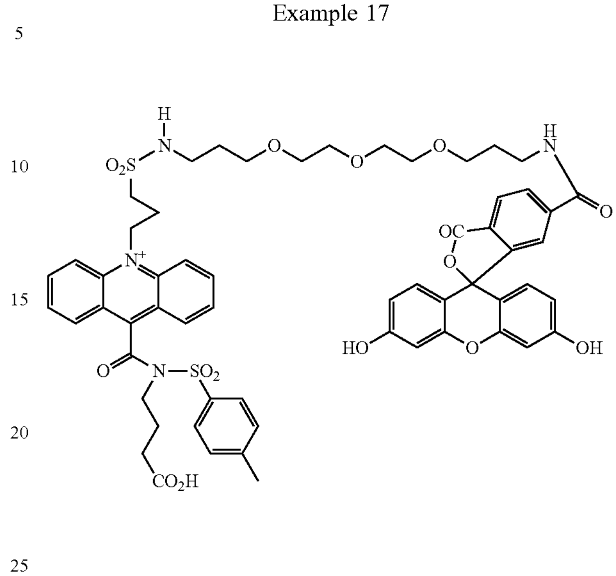

The titled compound was prepared using the same procedure outlined for the preparation of Example 12 utilizing 0.01 g (0.011 mmol) of the product from Example 4, DMF (0.25 mL), 0.014 g (0.026 mmol) of 6-carboxyfluorescein-PFP ester (prepared from 6-carboxyfluorescein and pentafluorophenyl trifluoroacetate) and DIEA (0.025 mL, 0.055 mmol). Yield 0.005 g of a yellow film (titled compound). MS (M+): calculated for $C_{59}H_{61}N_4O_{16}S_2$+: Exact Mass: 1145.3518; Molecular Weight: 1146.2623. UPLC/MS measured 1145.30.

Example 18

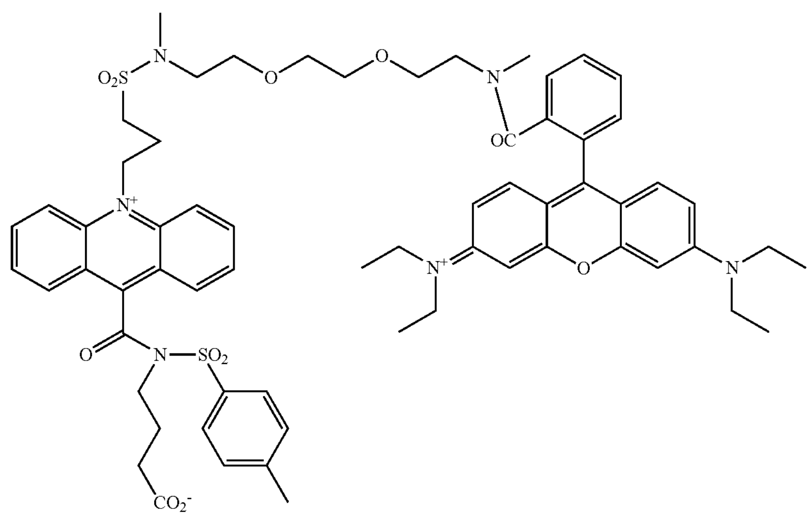

The titled compound was prepared using the same procedure outlined for the preparation of Example 12 utilizing 0.0049 g (0.0057 mmol) of the product from Example 5, DMF (0.25 mL), 0.01 g (0.016 mmol) of rhodamine B-PFP ester (prepared from rhodamine B and pentafluorophenyl trifluoroacetate) and DIEA (0.025 mL, 0.055 mmol). Yield 0.0016 g of a purple film (titled compound). MS (M+): calculated for $C_{64}H_{75}N_6O_{11}S_2$+: Exact Mass: 1167.49; Molecular Weight: 1168.45. UPLC/MS measured 1167.61.

Example 19

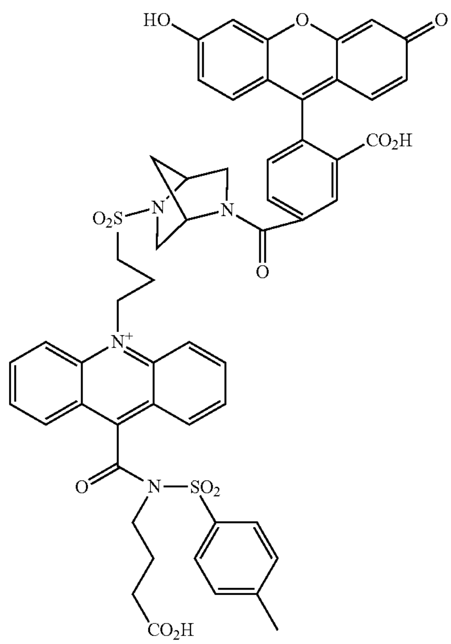 [SMILES: Cc1ccc(S(=O)(=O)N(CCCC(=O)O)C(=O)c2c3ccccc3[n+](CCCS(=O)(=O)N3CC4CC3CN4C(=O)c3ccc(-c4c5ccc(=O)cc-5oc5cc(O)ccc45)c(C(=O)O)c3)c3ccccc23)cc1]

The titled compound was prepared using the same procedure outlined for the preparation of Example 12 utilizing 0.0042 g (0.0054 mmol) of the product from Example 6, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0048 g of an orange yellow film (titled compound). MS (M+): calculated for $C_{54}H_{47}N_4O_{13}S_2$+: Exact Mass: 1023.2576; Molecular Weight: 1024.0994. UPLC/MS measured 1023.22.

Example 20

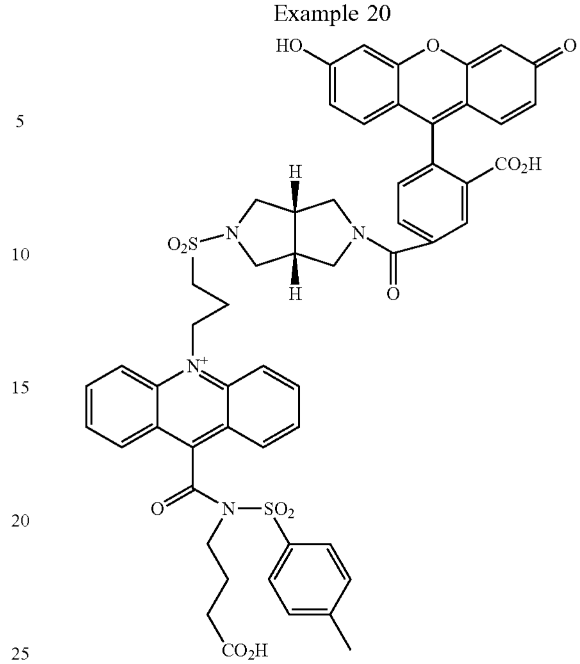

The titled compound was prepared using the same procedure outlined for the preparation of Example 12 utilizing 0.0045 g (0.005 mmol) of the product from Example 7, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0033 g of an orange yellow film (titled compound). MS (M+): calculated for $C_{55}H_{49}N_4O_{13}S_2$+: Exact Mass: 1037.2732; Molecular Weight: 1038.1260. UPLC/MS measured 1037.18.

Example 21

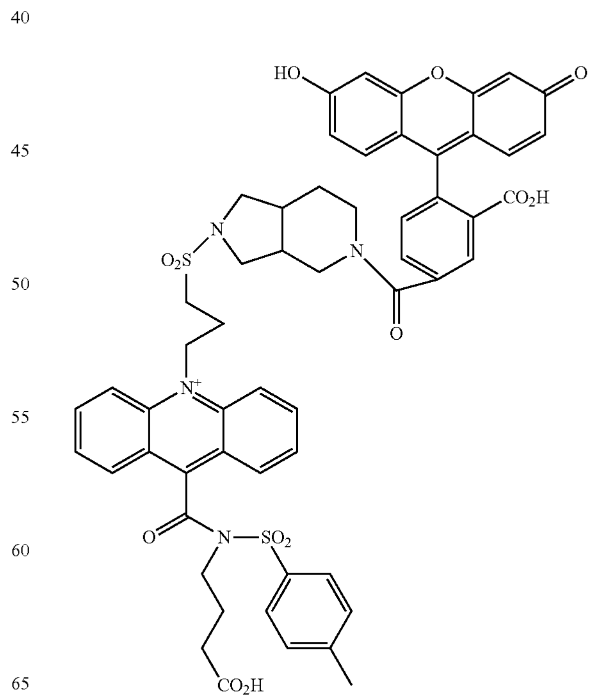

The titled compound was prepared using the same procedure outlined for the preparation of Example 12 utilizing 0.0038 g (0.0042 mmol) of the product from Example 8, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0023 g of an orange yellow film (titled compound). MS (M+): calculated for $C_{54}H_{47}N_4O_{13}S_2$+: Exact Mass: 1051.2889; Molecular Weight: 1052.1526. UPLC/MS measured 1051.30.

Example 22

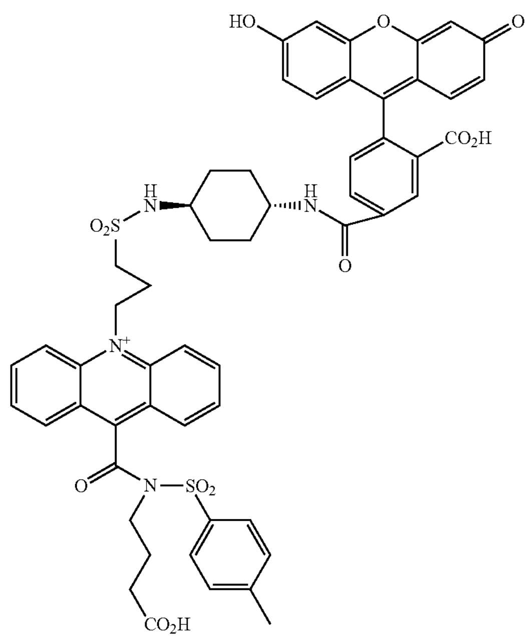 [SMILES: Cc1ccc(S(=O)(=O)N(CCCC(=O)O)C(=O)c2c3ccccc3[n+](CCCS(=O)(=O)N[C@H]3CC[C@H](NC(=O)c4ccc(-c5c6ccc(=O)cc-6oc6cc(O)ccc56)c(C(=O)O)c4)CC3)c3ccccc23)cc1]

The titled compound was prepared using the same procedure outlined for the preparation of Example 12 utilizing 0.005 g (0.0063 mmol) of the product from Example 9, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0042 g of a yellow film (titled compound). MS (M+): calculated for $C_{55}H_{51}N_4O_{13}S_2$+: Exact Mass: 1039.2889; Molecular Weight: 1040.1419. UPLC/MS measured 1039.29.

Example 23

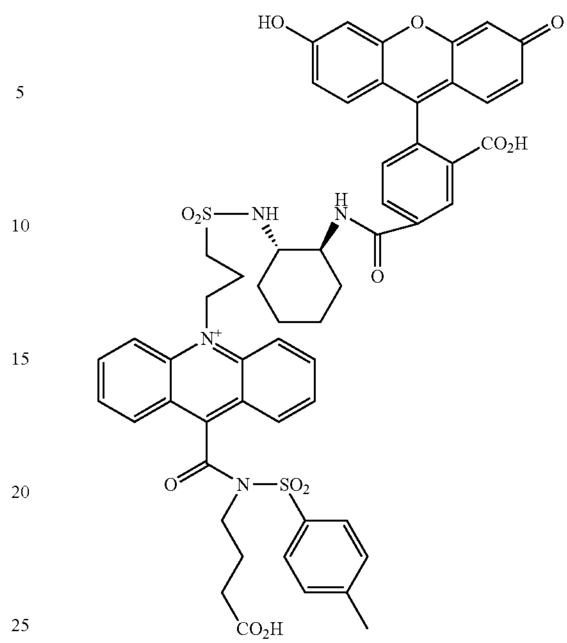

The titled compound was prepared using the same procedure outlined for the preparation of Example 12 utilizing 0.0057 g (0.0072 mmol) of the product from Example 10, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0024 g of a yellow film (titled compound). MS (M+): calculated for $C_{57}H_{55}N_4O_{13}S_2$+: Exact Mass: 1039.2889; Molecular Weight: 1040.1419. UPLC/MS measured 1039.21.

Example 24

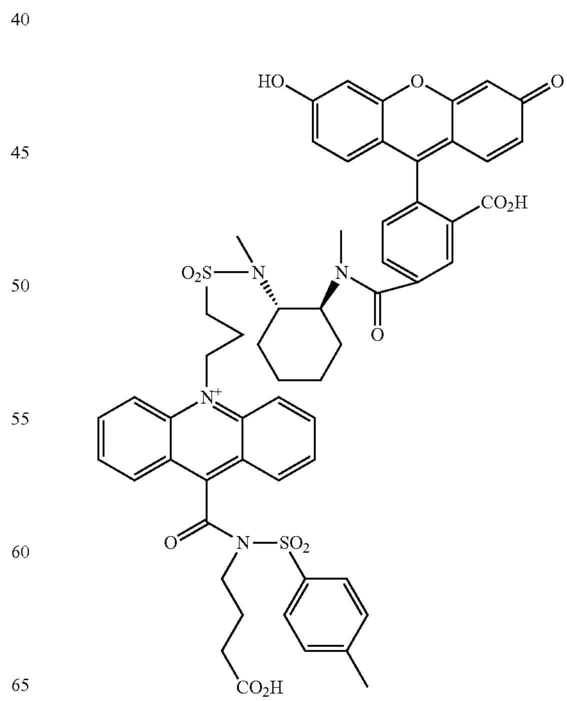

The titled compound was prepared using the same procedure outlined for the preparation of Example 12 utilizing 0.003 g (0.0036 mmol) of the product from Example 11, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0006 g of a yellow film (titled compound). MS (M+): calculated for $C_{57}H_{55}N_4O_{13}S_2$+: Exact Mass: 1067.32; Molecular Weight: 1068.20. UPLC/MS measured 1067.14.

Example 25

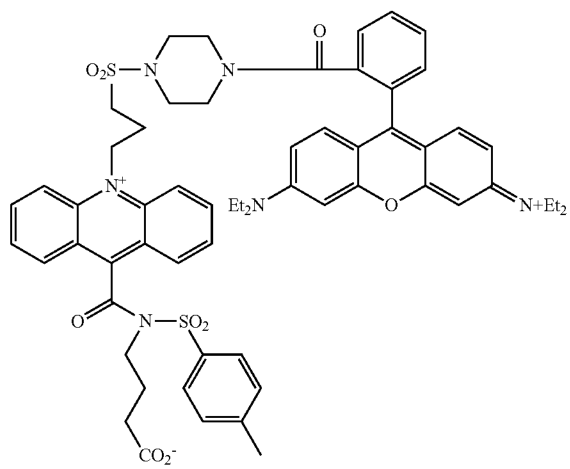

The titled compound was prepared using the same procedure outlined for the preparation of Example 12 utilizing 0.006 g (0.008 mmol) of the product from Example 2, DMF (0.2 mL), 0.008 g (0.013 mmol) of rhodamine B-PFP ester (prepared from rhodamine B and pentafluorophenyl trifluoroacetate) and DIEA (0.01 mL, 0.06 mmol). Yield 0.0031 g of a purple film (titled compound). MS (M+): calculated for $C_{60}H_{65}N_6O_9S_2$+: Exact Mass: 1077.42; Molecular Weight: 1078.33. UPLC/MS measured 1077.51.

Example 26

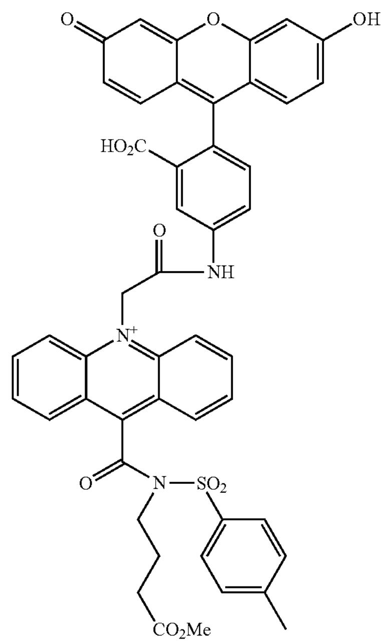 [SMILES: COC(=O)CCCN(C(=O)c1c2ccccc2[n+](CC(=O)Nc2ccc(-c3c4ccc(=O)cc-4oc4cc(O)ccc34)c(C(=O)O)c2)c2ccccc12)S(=O)(=O)c1ccc(C)cc1]

CP-acridine methyl ester (*J. Org. Chem.* 1998, 63, 5636-5639) (0.012 g, 0.025 mmol) and 5-(iodoacetamido)fluorescein (0.015 g, 0.029 mmol) were mixed in a 5 mL round bottom flask equipped with a nitrogen inlet. Without solvent, the flask was heated in an oil bath at 160-170° C. for 15 minutes. After this time, LCMS indicated a complex mixture with the starting materials both present as well as the titled compound as a component. The reaction was taken up in DMF/MeOH/water (~0.5 mL of each) and purified by reverse phase HPLC using a YMC ODS AQ 30×150 mm steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% Formic acid. The volatile components were removed in vacuo on a rotary evaporator at 30° C. and dried under high vacuum (1 mm Hg) over 24 hours. Yield 0.0007 g of a yellow film (titled compound). MS (M+): calculated for $C_{48}H_{38}N_3O_{11}$ S+: Exact Mass: 864.2222; Molecular Weight: 864.8933. UPLC/MS measured 864.43.

Example 27

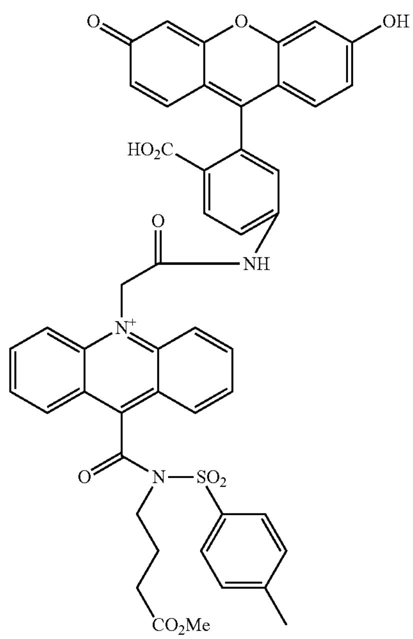 [SMILES: COC(=O)CCCN(C(=O)c1c2ccccc2[n+](CC(=O)Nc2ccc(C(=O)O)c(-c3c4ccc(=O)cc-4oc4cc(O)ccc34)c2)c2ccccc12)S(=O)(=O)c1ccc(C)cc1]

The titled compound was prepared using the same procedure outlined for the preparation of Example 26 utilizing 0.012 g (0.025 mmol) CP-acridinium methyl ester and 0.006 g (0.012 mmol) of 6-(iodoacetamido)fluorescein. Yield 0.0011 g of a yellow film (titled compound). MS (M+): calculated for $C_{48}H_{38}N_3O_{11}S+$: Exact Mass: 864.2222; Molecular Weight: 864.8933. UPLC/MS measured 864.51.

Example 28

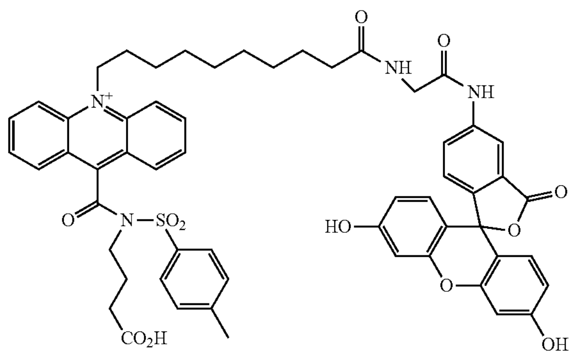 [SMILES: Cc1ccc(S(=O)(=O)N(CCCC(=O)O)C(=O)c2c3ccccc3[n+](CCCCCCCCCC(=O)NCC(=O)Nc3ccc4c(c3)C(=O)OC43c4ccc(O)cc4Oc4cc(O)ccc43)c3ccccc23)cc1]

The above compound was prepared from:

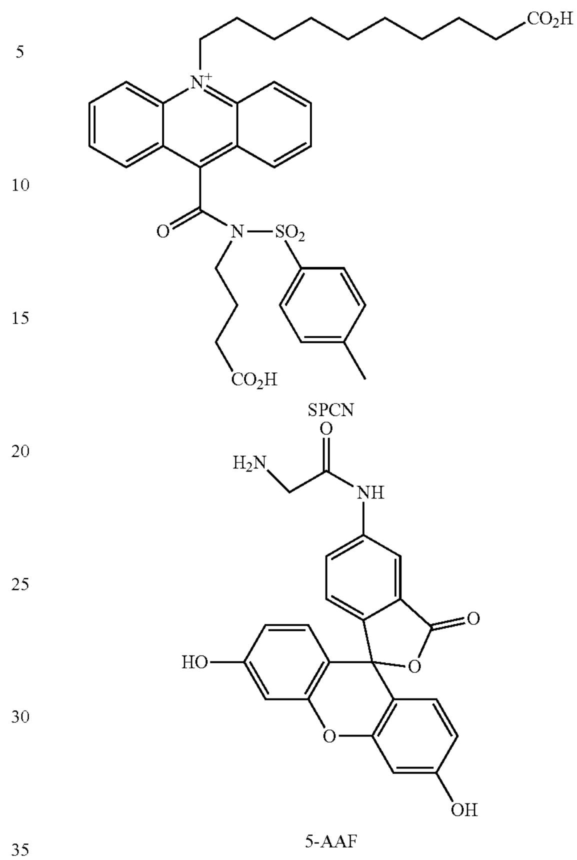

SPCN

5-AAF

SPCN (0.048 g), (*Organic Letters,* 2003, 5(21), 3779), was dissolved in 0.5 mL DMF. 0.128 mL of DIEA was added followed by PyAOP (0.032 g). The reaction was stirred at ambient temperature for 5 minutes (preactivation). 0.032 g 5-acetamidoaminofluorescein (5-AAF) (Chemistry of Materials, 1992, 4(4), 879-84) was dissolved in 1 mL of DMF and 0.064 mL of DIEA. The 5-AAF solution was added to the SPCN solution. After 18 hr, the reaction was treated with 3 mL of water. The solution was purified by HPLC by directly injecting the solution onto a YMC ODS-AQ column (40×100). Elution was at 45 mL/min with a gradient of 5 to 40% acetonitrile over 70 minutes (mobile phase ACN/$H_2O$/$H_2O$-0.5% TFA). The fractions containing the product were frozen and lyophilized. Yield 0.026 g (titled compound). MS consistent with titled compound.

Example 29

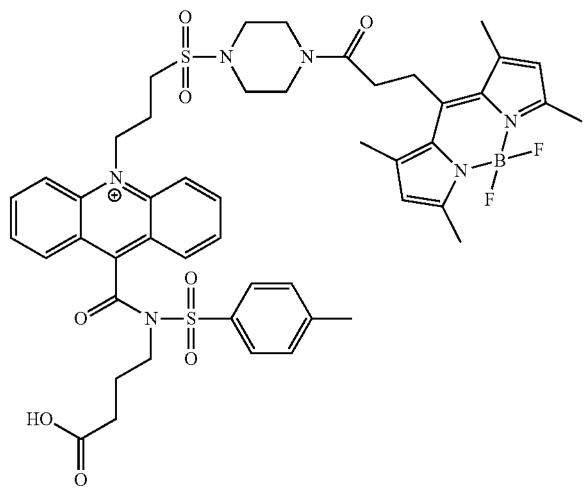

The titled compound was prepared using a similar procedure outlined for the preparation of example 12 utilizing 0.01 g of the product from example 2, DMF (0.5 mL), 0.005 g (0.012 mmol) of BODIPY™ 493/503 NHS Ester (ThermoFisher) and DIEA (0.01 mL, 0.06 mmol). Reaction was stirred overnight. Yield 0.0021 g of a red film (titled compound). MS (M+): calculated for $C_{48}H_{54}BF_2N_6O_8S_2$+; Exact Mass: 955.3500; Molecular Weight: 955.9203. UPLC/MS measured 955.38.

Example 30

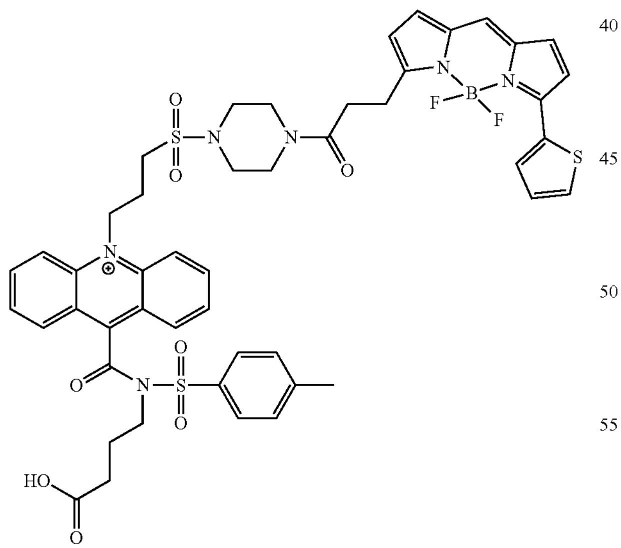

The titled compound was prepared using a similar procedure outlined for the preparation of example 12 utilizing 0.014 g (0.018 mmol) of the product from example 2, DMF (0.5 mL), 0.005 g (0.011 mmol) of BDP 558/568 NHS Ester (Lumiprobe) and DIEA (0.01 mL, 0.06 mmol). Reaction was stirred overnight. Yield 0.0033 g of a purple film (titled compound). MS (M+): calculated for $C_{48}H_{48}BF_2N_6O_8S_3$+; Exact Mass: 981.2751; Molecular Weight: 981.9323. UPLC/MS measured 981.33.

Example 31

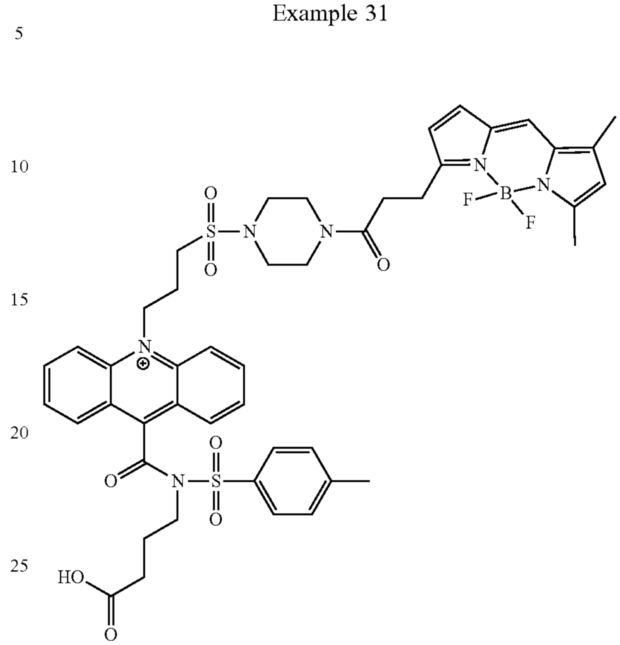

The titled compound was prepared using a similar procedure outlined for the preparation of example 12 utilizing 0.03 g (0.039 mmol) of the product from example 2, DMF (1 mL), 0.01 g (0.025 mmol) of BDP FL NHS Ester (Lumiprobe) and DIEA (0.02 mL, 0.12 mmol). Reaction was stirred overnight. Yield 0.0026 g of a red film (titled compound). MS (M+): calculated for $C_{46}H_{50}BF_2N_6O_8S_2$+; Exact Mass: 927.3187; Molecular Weight: 927.8663. UPLC/MS measured 927.52.

Example 32

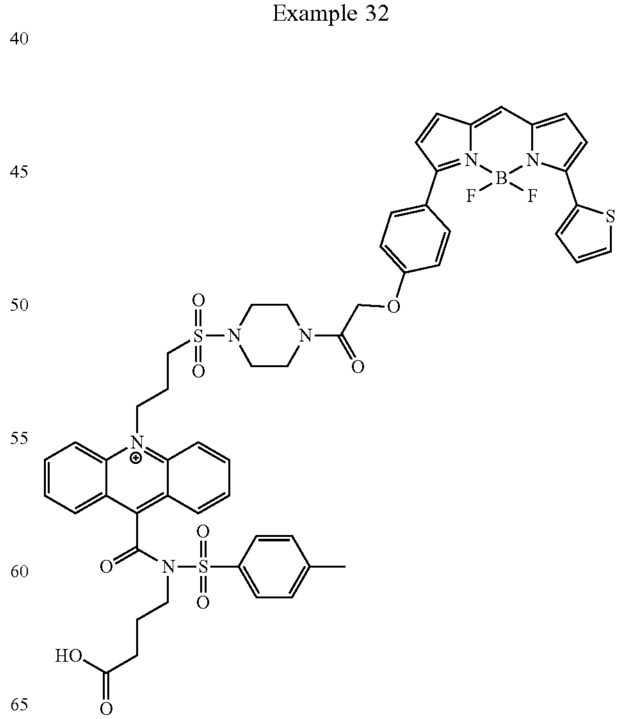

The titled compound was prepared using a similar procedure outlined for the preparation of example 12 utilizing 0.03 g (0.039 mmol) of the product from example 2, DMF (1 mL), 0.014 g (0.027 mmol) of BDP TR NHS Ester (Lumiprobe) and DIEA (0.02 mL, 0.12 mmol). Reaction was stirred overnight. Yield 0.019 g of a blue film (titled compound). MS (M+): calculated for $C_{53}H_{50}BF_2N_6O_9S_3$+; Exact Mass: 1059.2857; Molecular Weight: 1060.0023. UPLC/MS measured 1059.26.

Example 33

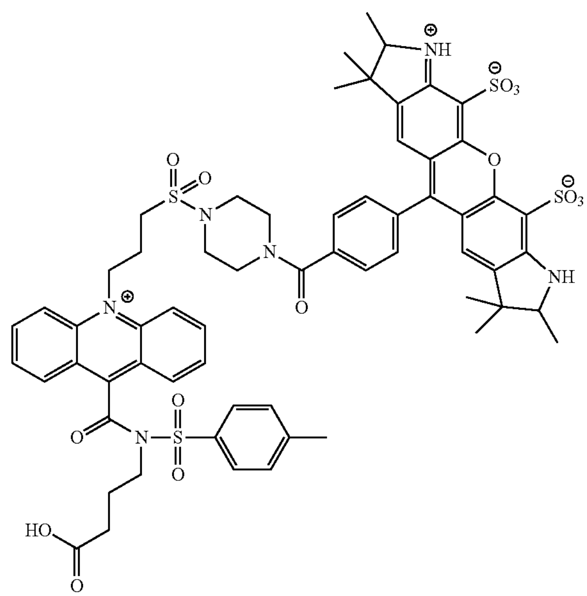

A 4 mL reaction vial equipped with a magnetic stir bar and nitrogen inlet was charged with 0.005 g (0.0069 mmol) of Alexa Fluor 532 carboxylic acid, 0.0029 g of HBTU (0.0076 mmol), DMSO (0.5 mL) and DIEA (0.05 mL, 0.3 mmol). The reaction was stirred at room temperature for 15 minutes before adding a DMSO solution (0.5 mL) containing the product from example 2 (0.015 g, 0.020 mmol). The reaction was stirred overnight. The crude reaction mixture was diluted with MeOH and water. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield 0.0025 g of red film. MS (M+): calculated for $C_{62}H_{64}N_6O_{15}S_4$: Exact Mass: 1260.3312; Molecular Weight: 1261.4610. UPLC/MS measured 1262.42.

Example 34

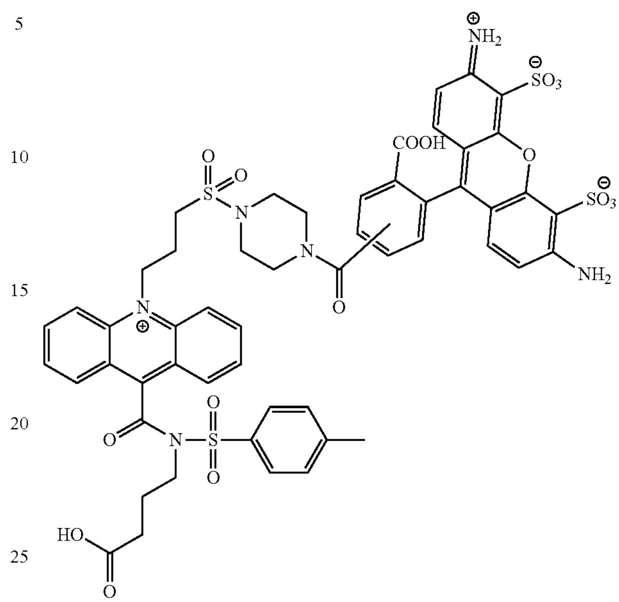

The titled compound was prepared using a similar procedure outlined for the preparation of Example 33 utilizing 0.012 g (0.016 mmol) of the product from Example 2, DMSO (1 mL), 0.005 g (0.0059 mmol) of Alexa Fluor 488 carboxylic acid, 0.0025 g (0.0066 mmol) of HBTU, and DIEA (0.05 mL, 0.3 mmol). Yield 0.002 g of a red film (titled compound 5(6)-mixed isomers). MS (M+): calculated for $C_{53}H_{48}N_6O_{17}S_4$; Exact Mass: 1168.1959; Molecular Weight: 1169.2320. UPLC/MS measured 1169.28.

Example 35

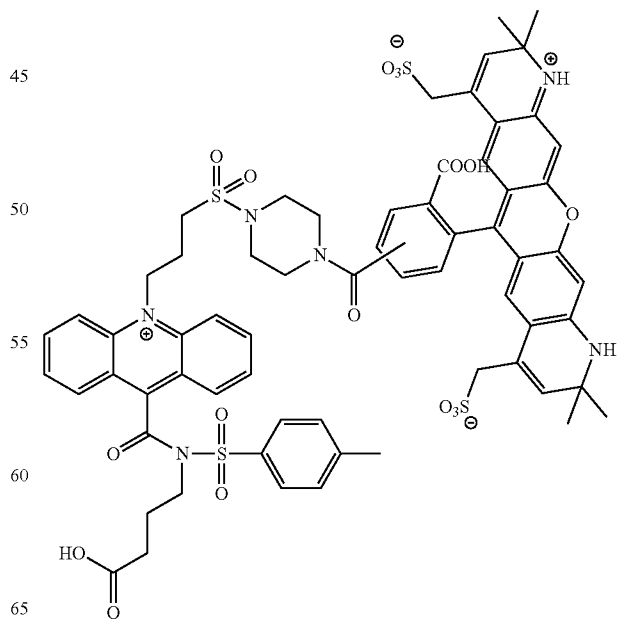

The titled compound was prepared using a similar procedure outlined for the preparation of Example 33 utilizing 0.0085 g (0.011 mmol) of the product from Example 2, DMSO (1 mL), 0.005 g (0.005 mmol) of Alexa Fluor 568 carboxylic acid, 0.0021 g (0.0055 mmol) of HBTU, and DIEA (0.05 mL, 0.3 mmol). Yield 0.0025 g of a purple film (titled compound 5(6)-mixed isomers). MS (M+): calculated for $C_{65}H_{64}N_6O_{17}S_4$; Exact Mass: 1328.3211; Molecular Weight: 1329.4920. UPLC/MS measured 1330.24.

Example 36

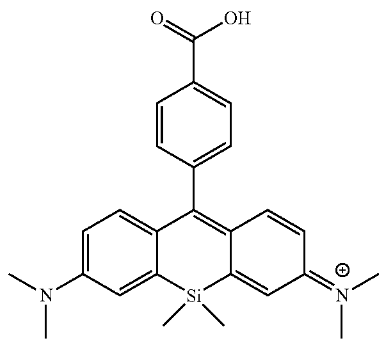

A 20 mL reaction vial equipped with a magnetic stir bar was charged with 0.075 g (0.17 mmol) of Methyl-4-carboxy-siliconrhodamine (*Angew. Chemi. Int. Ed.* 2018, 57, 2436-2440) and aqueous HCl (1 mL, 6 M). The contents were heated to 90° C. for 1 hour. The mixture was cooled to room temperature before diluting with 4:1 $CHCl_3$: methanol solvent mixture. The organic layer was washed with water and then brine before drying over sodium sulfate. The solvent was removed in vacuo. The crude solid was dissolved with MeOH and water. The entire solution was purified by reverse phase HPLC by elution on a YMC ODS AQ 50×250 mm I.D. steel column with a Waters Separations 2000 system monitored at 254 nm. Recorder chart speed 5 mm/min. A manual step gradient method (flow rate 70 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield 0.054 g of blue film. MS (M+): calculated for $C_{26}H_{29}$N202Si+; Exact Mass: 429.1993; Molecular Weight: 429.6145. UPLC/MS measured 429.19.

Example 37

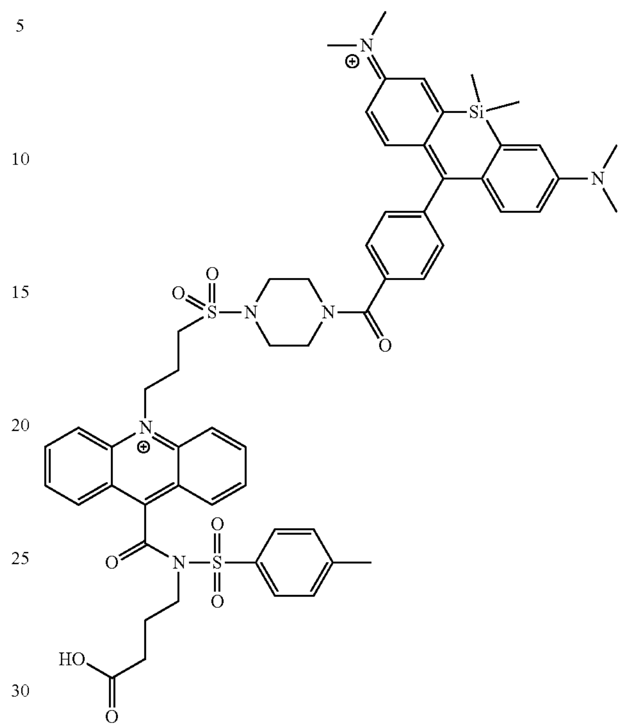

The titled compound was prepared using a similar procedure outlined for the preparation of Example 12 utilizing 0.025 g (0.033 mmol) of the product from Example 2, DMF (1 mL), 0.009 g (0.015 mmol) of 4-carboxy-SiR-PFP ester (example 37 and pentafluorophenyl trifluoroacetate) and DIEA (0.1 mL, 0.6 mmol). Yield 0.004 g of a blue film (titled compound). MS (M+): calculated for $C_{58}H_{64}N_6O_8S_2Si^{2+}$; Exact Mass: 1064.3985; Molecular Weight: 1065.3879. UPLC/MS measured 1064.44 (weak); M++532.46 (strong).

Example 38

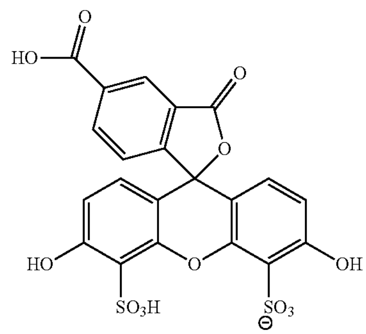

A 20 mL reaction vial equipped with a magnetic stir bar was charged with 0.315 g (0.84 mmol) of 5-carboxyfluorescein and fuming sulfuric acid (5 mL, 30% free $SO_3$ basis), and was heated to 90° C. for 1 hour. The reaction mixture was cooled to room temperature and then carefully added to a beaker containing ice before adding KCl (1 g) resulting in a yellow precipitate. The solid was filtered, washed with cold water and acetone, and dried under high vacuum for 18 hours. The solid was used in the next step without further purification. Yield 0.250 g of a yellow solid. MS (M−): calculated for $C_{21}H_{11}O_{13}S_2-$; Exact Mass: 534.9647; Molecular Weight: 535.4265. UPLC/MS measured 534.93.

Example 39

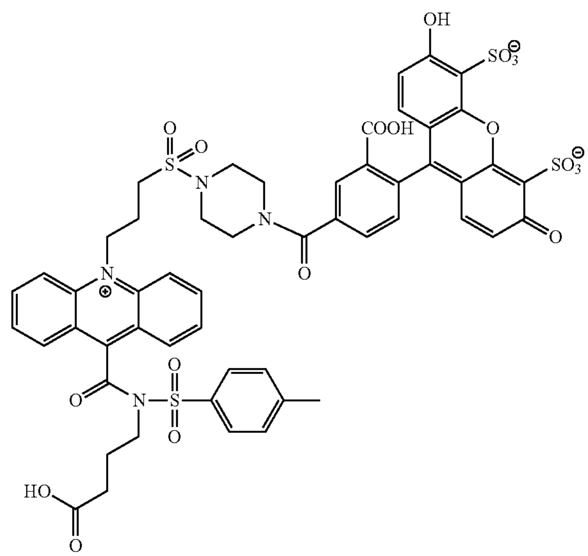

The titled compound was prepared using a similar procedure outlined for the preparation of Example 12 utilizing 0.009 g (0.012 mmol) of the product from Example 2, DMF (0.5 mL), 0.009 g (0.015 mmol) of 5-carboxy-4',5'-disulfo-fluorescein-PFP ester (Example 38 and pentafluorophenyl trifluoroacetate) and DIEA (0.05 mL, 0.3 mmol). Yield 0.007 g of a yellow film. MS (M−): calculated for $C_{53}H_{45}N_4O_{19}S_4^-$; Exact Mass: 1169.1566; Molecular Weight: 1170.1925. UPLC/MS measured 1169.99.

Example 40

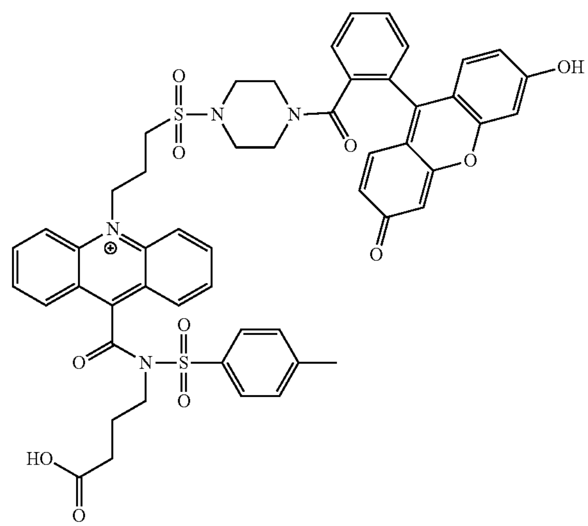 [SMILES: Cc1ccc(S(=O)(=O)N(CCCC(=O)O)C(=O)c2c3ccccc3[n+](CCCS(=O)(=O)N3CCN(C(=O)c4ccccc4-c4c5ccc(=O)cc-5oc5cc(O)ccc45)CC3)c3ccccc23)cc1]

A 4 mL reaction vial equipped with a magnetic stir bar and nitrogen inlet was charged with 0.013 g (0.04 mmol) of fluorescein, 0.014 g of HBTU (0.037 mmol), DMSO (1 mL) and DIEA (0.1 mL, 0.6 mmol). The reaction was stirred at 45° C. for 60 minutes. The solution was then cooled to room temperature before adding a DMSO solution (0.5 mL) containing the product from Example 2 (0.04 g, 0.052 mmol). The reaction was stirred overnight. The crude reaction mixture was diluted with MeOH and water. The entire solution was purified by reverse phase HPLC by elution on a YMC ODS AQ 50×250 mm I.D. steel column with a Waters Separations 2000 system monitored at 254 nm. Recorder chart speed 5 mm/min. A manual step gradient method (flow rate 70 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield 0.002 g of red film. MS (M+): calculated for $C_{52}H_{47}N_4O_{11}S_2+$; Exact Mass: 967.2677; Molecular Weight: 968.0845. UPLC/MS measured 967.32 (weak); M++484.38 (strong).

Example 41

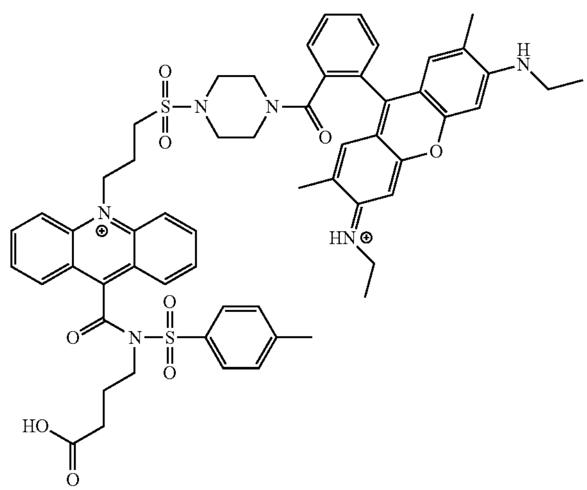 [SMILES: CCNc1cc2oc3c/c(=[NH+]\CC)c(C)cc-3c(-c3ccccc3C(=O)N3CCN(S(=O)(=O)CCC[n+]4c5ccccc5c(C(=O)N(CCCC(=O)O)S(=O)(=O)c5ccc(C)cc5)c5ccccc54)CC3)c2cc1C]

The titled compound was prepared using a similar procedure outlined for the preparation of Example 12 utilizing 0.015 g (0.020 mmol) of the product from Example 2, DMF (0.5 mL), 0.008 g (0.016 mmol) of rhodamine 19-NHS ester (Rhodamine 19 and TSTU) and DIEA (0.05 mL, 0.3 mmol). Yield: 0.002 g of red film. MS (M+): calculated for $C_{58}H_{62}N_6O_9S_2^{2+}$; Exact Mass: 1050.4009; Molecular Weight: 1051.2859. UPLC/MS measured 1049.31 (weak); M++525.46 (strong).

Example 42

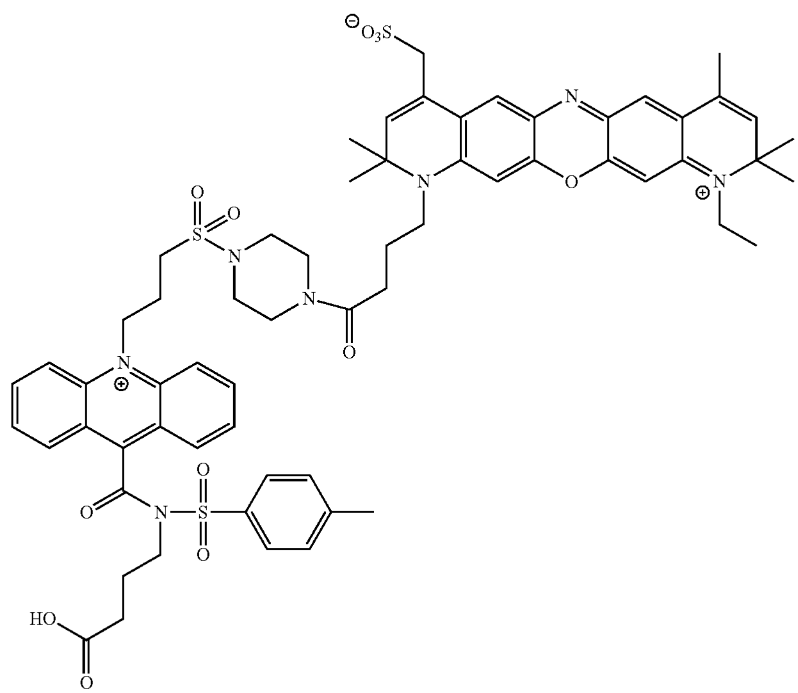

The titled compound was prepared using a similar procedure outlined for the preparation of Example 12 utilizing 0.0065 g (0.0085 mmol) of the product from Example 2, DMF (0.4 mL), 0.002 g (0.003 mmol) of Atto 700 NHS-ester, and DIEA (0.05 mL, 0.3 mmol). Yield: 0.003 g of green film. MS (M+): calculated for $C_{62}H_{70}N_7O_{12}S_3$+; Exact Mass: 1200.4239; Molecular Weight: 1201.4585. UPLC/MS measured 1200.56 (weak); M++600.92 (strong).

Example 43

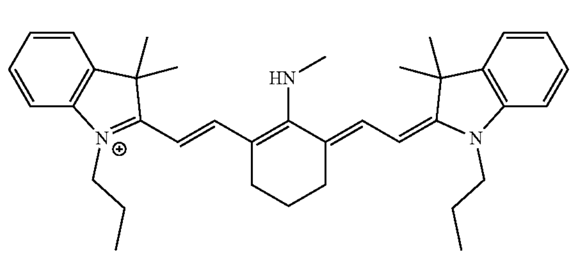 [SMILES: CCCN1/C(=C/C=C2\CCCC(/C=C/C3=[N+](CCC)c4ccccc4C3(C)C)=C2NC)C(C)(C)c2ccccc21]

A 20 mL reaction vial equipped with a magnetic stir bar and nitrogen inlet was charged with 0.2 g (0.30 mmol) of IR 780 iodide, DMF (2 mL), and a solution of methylamine in THF (3 mL, 2 M). This was heated to 80° C. for 1 hour, during which time the color of the solution changed from green to blue. The reaction mixture was cooled to room temperature before triturating the product in diethyl ether. The product was used in the next step without further purification. Yield: 0.160 g of blue powder. MS (M+): calculated for Chemical Formula: $C_{37}H_{48}N_3$+; Exact Mass: 534.3843; Molecular Weight: 534.8115. UPLC/MS measured 534.37.

Example 44

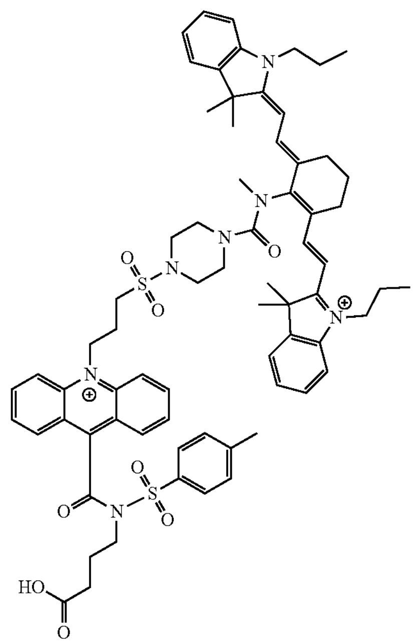 [SMILES: CCCN1/C(=C/C=C2\CCCC(/C=C/C3=[N+](CCC)c4ccccc4C3(C)C)=C2N(C)C(=O)N2CCN(S(=O)(=O)CCC[n+]3c4ccccc4c(C(=O)N(CCCC(=O)O)S(=O)(=O)c4ccc(C)cc4)c4ccccc43)CC2)C(C)(C)c2ccccc21]

In a 20 mL reaction vial equipped with a magnetic stir bar and nitrogen inlet was charged with 0.025 g (0.038 mmol) of the product from Example 43, DCM (10 mL), and 0.033 g (0.114 mmol) of triphosgene. The reaction mixture was cooled to 0° C. in an ice bath before adding 0.3 mL of DIEA. Stirring was continued for 1 hour before the solvent was removed in vacuo. The crude material was then charged with 0.040 g (0.052 mmol) of the product from Example 2, DMF (1 mL), and DIEA (0.1 mL, 0.6 mmol). The reaction mixture was stirred for 36 hours at room temperature. The crude reaction mixture was diluted with MeOH and water. The entire solution was purified by reverse phase HPLC by elution on a YMC ODS AQ 50×250 mm I.D. steel column with a Waters Separations 2000 system monitored at 254 nm. Recorder chart speed 5 mm/min. A manual step gradient method (flow rate 70 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield 0.004 g of green film. MS (M+): calculated for $C_{70}H_{83}N_7O_8S_2^{2+}$; Exact Mass: 1213.5734; Molecular Weight: 1214.5939. UPLC/MS measured 1212.50 (weak); M++607.05 (strong).

Example 45

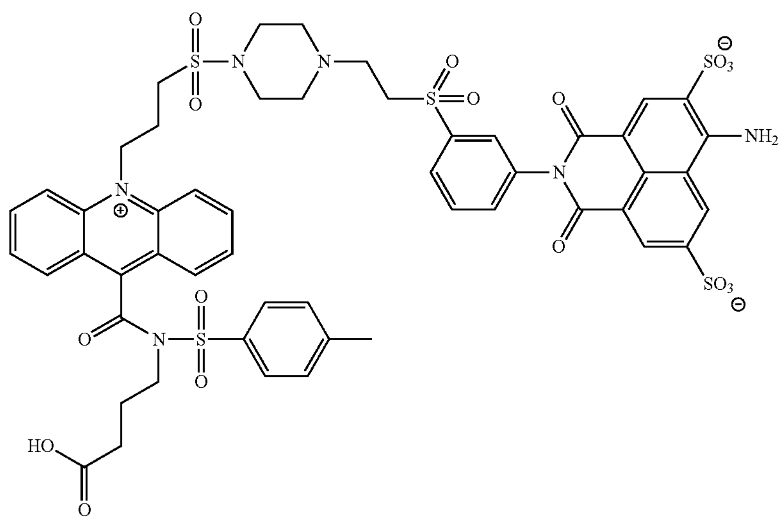

The titled compound was prepared using a similar procedure outlined for the preparation of Example 12 utilizing 0.0165 g (0.021 mmol) of the product from Example 2, DMF (1 mL), 0.008 g (0.015 mmol) of Lucifer Yellow VS dilithium salt, and DIEA (0.05 mL, 0.3 mmol). Yield: 0.009 g of yellow powder. MS (M−): calculated for $C_{52}H_{49}N_6O_{17}S_5^-$; Exact Mass: 1189.1763; Molecular Weight: 1190.2895. UPLC/MS measured 1189.42.

Example 46

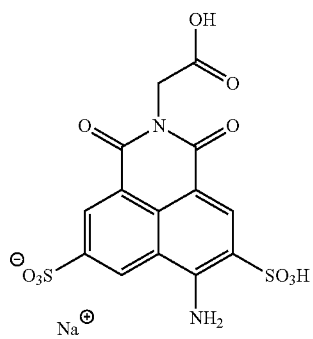

A 4 mL reaction vial equipped with a magnetic stir bar was charged with 0.110 g (0.30 mmol) of Lucifer Yellow anhydride, 0.123 g (1.65 mmol) of glycine, and an aqueous solution of sodium acetate (3 mL, 1M). The mixture was heated to 90° C. and stirred overnight. The crude reaction mixture was diluted with MeOH and water. The entire solution was purified by reverse phase HPLC by elution on a YMC ODS AQ 50×250 mm I.D. steel column with a Waters Separations 2000 system monitored at 254 nm. Recorder chart speed 5 mm/min. A manual step gradient method (flow rate 70 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield: 0.120 g of yellow powder. MS (M−): calculated for $C_{14}H_9N_2O_{10}S_2$; Exact Mass: 428.9704; Molecular Weight: 429.3505. UPLC/MS measured 429.05.

Example 47

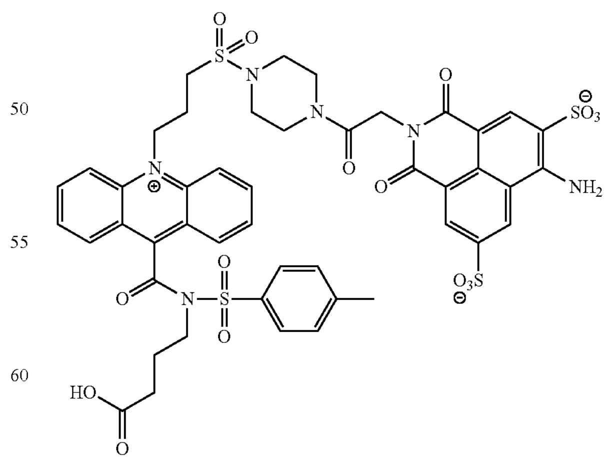

The titled compound was prepared using a similar procedure outlined for the preparation of Example 12 utilizing 0.085 g (0.11 mmol) of the product from Example 2, DMF (1 mL), 0.040 g (0.076 mmol) of the product from Example 46-NHS ester (example 46 and TSTU) and DIEA (0.17 mL, 1 mmol). Yield: 0.018 g of yellow powder. MS (M−): calculated for $C_{46}H_{43}N_6O_{16}S_4$−, Exact Mass: 1063.1624, Molecular Weight: 1064.1165. UPLC/MS measured 1063.24.

Example 48

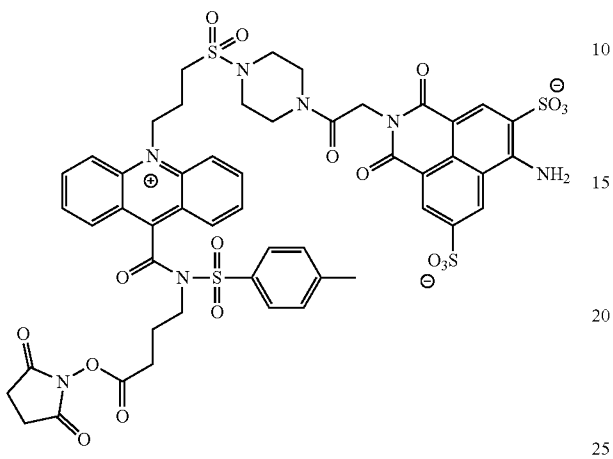

A 4 mL reaction vial equipped with a magnetic stir bar and nitrogen inlet was charged with 0.013 g (0.012 mmol) of the product from Example 47, 0.0055 mg (0.018 mmol) of TSTU, DMSO (0.5 mL), and DIEA (0.05 mL, 0.3 mmol). Mix was stirred for 1 hour at room temperature before being diluted in a small amount of ACN. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.05% formic acid. Fractions containing the product were combined and the volatile components were removed in vacuo on a rotary evaporator at 30° C. followed by high vacuum for 18 hours at room temperature. Yield: 0.008 mg of yellow film. MS (−): calculated for $C_{50}H_{46}N_7O_{18}S_4$−; Exact Mass: 1160.1788; Molecular Weight: 1161.1895. UPLC/MS measured 1160.28.

Example 49

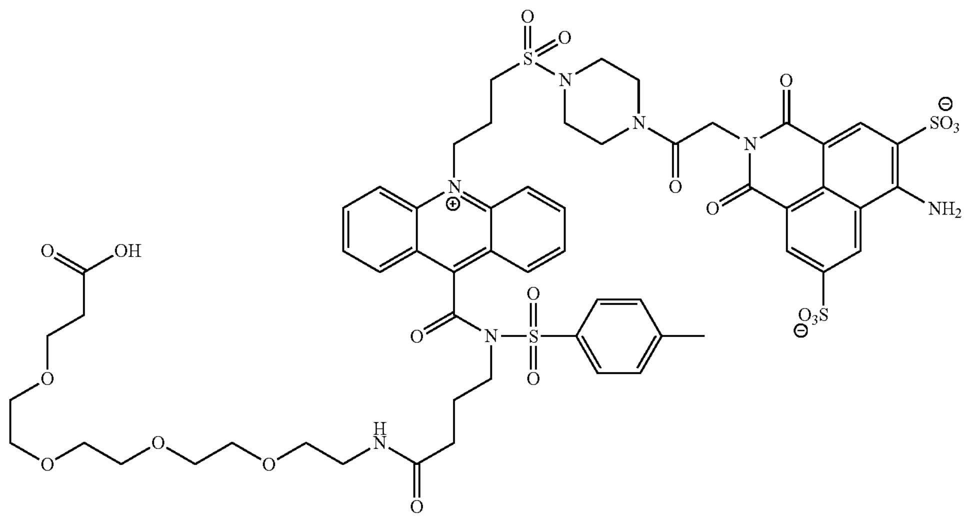

A 4 mL reaction vial equipped with a magnetic stir bar and nitrogen inlet was charged with 0.006 g (0.0052 mmol) of the product from Example 48, 0.020 g (0.062 mmol) of Amino-dPEG®4-t-butyl ester, DMF (0.5 mL), and DIEA (0.1 mL, 0.6 mmol). The mixture was stirred for 1 hour before being diluted in a small amount of ACN. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% formic acid. Fractions containing the product were combined and the volatile components were removed in vacuo on a rotary evaporator at 30° C. followed by high vacuum for 18 hours at room temperature. The purified material was transferred to a 4 mL reaction vial equipped with a stir bar and was dissolved in 1 mL of DCM and 1 mL of TFA. The mixture stirred for 1 hour before removing the solvents in vacuo on a rotary evaporator at 30° C. followed by high vacuum for 18 hours at room temperature. No further purification was necessary. Yield: 0.0088 g of yellow film. MS (−): calculated for $C_{57}H_{64}N_7O_{21}S_4$−; Exact Mass: 1310.3044; Molecular Weight: 1311.4075. UPLC/MS measured 1310.82.

Example 50

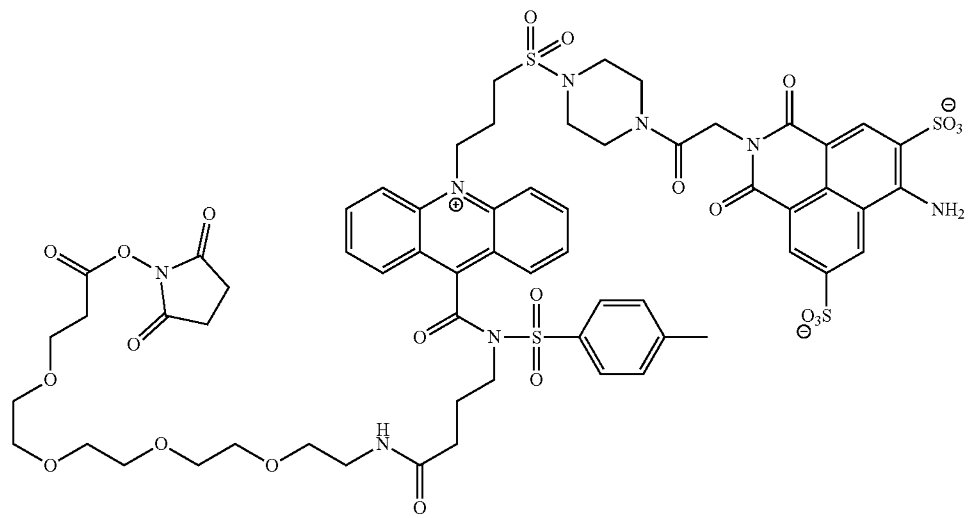

The titled compound was prepared using a similar procedure outlined for the preparation of Example 48 utilizing 0.0088 g (0.0067 mmol) of the product from Example 49, 0.003 g (0.010 mmol) of TSTU, DMF (0.5 mL), and DIEA (0.05 mL, 0.3 mmol). After purification and evaporation, 10% of the material had hydrolyzed back to the carboxylic acid form. Yield: 0.006 g. MS (−): calculated for $C_{61}H_{67}N_8O_{23}S_4$−; Exact Mass: 1407.3207; Molecular Weight: 1408.4805. UPLC/MS measured 1408.50.

Example 51

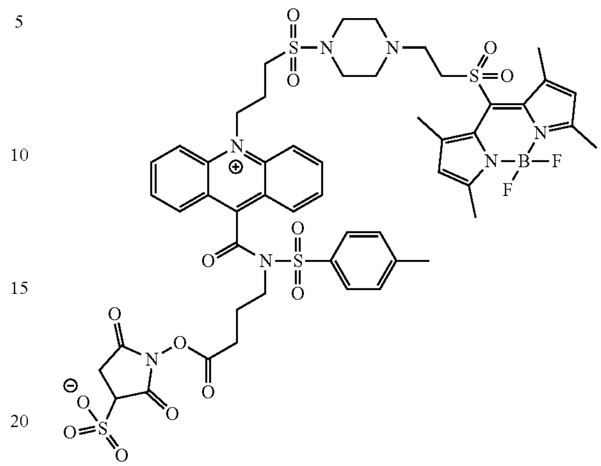

A 4 mL reaction vial equipped with a magnetic stir bar and nitrogen inlet was charged with 0.007 g (0.0072 mmol) of the product from Example 29, 0.0026 g (0.017 mmol) of EDC, 0.0036 g (0.017 mmol) of N-hydroxysulfosuccinimide sodium salt, DMF (0.5 mL), and DIEA (0.01 mL, 0.06 mmol). Reaction was stirred overnight before being diluted in a small amount of ACN. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.05% formic acid. Fractions containing the product were combined and the volatile components were removed in vacuo on a rotary evaporator at 30° C. followed by high vacuum for 18 hours at room temperature. Yield: 0.0025 g. MS (+): calculated for $C_{52}H_{56}$BF2N7013$S_3$; Exact Mass: 1131.3159; Molecular Weight: 1132.0428. UPLC/MS measured (M-F)+1112.20.

Example 52

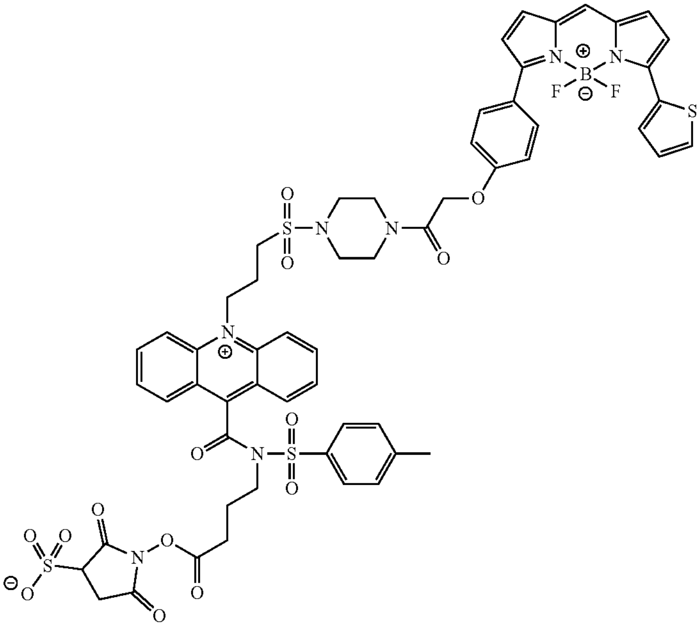

The titled compound was prepared using a similar procedure outlined for the preparation of Example 51 utilizing 0.009 g (0.0085 mmol) of the product from Example 32, 0.0026 g (0.017 mmol) of EDC, 0.0036 g (0.017 mmol) of N-hydroxysulfosuccinimide sodium salt, DMF (0.5 mL), and DIEA (0.01 mL, 0.06 mmol). Yield: 0.0013 g. MS (+): calculated for $C_{57}H_{52}BF_2N_7O_{14}S_4$; Exact Mass: 1235.2516; Molecular Weight: 1236.1248. UPLC/MS measured (M−F)+1216.40.

Example 53

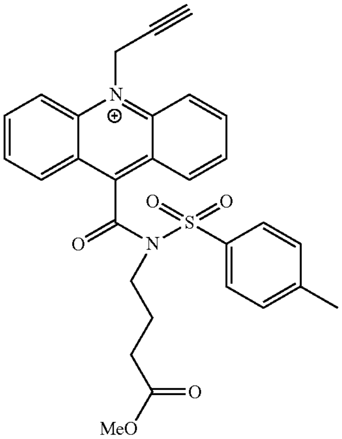 [SMILES: C#CC[n+]1c2ccccc2c(C(=O)N(CCCC(=O)OC)S(=O)(=O)c2ccc(C)cc2)c2ccccc21]

A 100 mL RB flask equipped with a stir bar and nitrogen inlet was charged with propargyl triflate (*J. Org Chem.*, 1977, 42, 3109-3113) (20.98 mmol) and $CH_2Cl_2$ (25 mL). To this solution was added 2,6-di-tert-butylpryridine (6.96 mL, 31.45 mmol) followed by the acridine (*J. Org Chem.*, 1998, 63, 5636-5639) (1.00 g, 2.10 mmol) and stirred for 18 h. The mixture was concentrated in vacuo. The residue was purified by reverse phase HPLC using a gradient method of 10% to 90% Acetonitrile/$H_2O$ with 0.5% TFA. The desired fractions were collected, pooled, frozen and lyophilized to afford 1.213 g of the title compound as a yellow solid (quant.). Yield: 1.213 g of yellow solid. MS (+): calculated for $C_{29}H_{27}N_2O_5S^+$; Exact Mass: 515.6; Molecular Weight: 515.6. UPLC/MS measured (M)+514.85.

Example 54

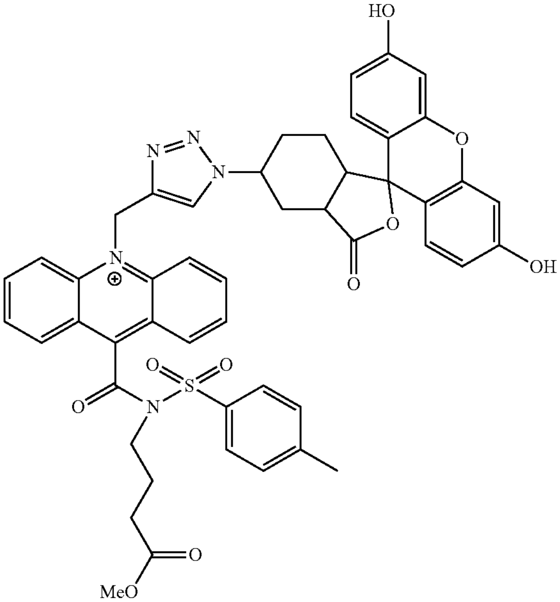 [SMILES: COC(=O)CCCN(C(=O)c1c2ccccc2[n+](Cc2cn(C3CCC4C(C3)C(=O)OC43c4ccc(O)cc4Oc4cc(O)ccc43)nn2)c2ccccc12)S(=O)(=O)c1ccc(C)cc1]

A 50 mL Rb flask equipped with a stir bar and nitrogen inlet was charged with the product of Example 53 (0.014 g, 0.027 mmol), 5-azidofluorescein (*J. Am. Chem. Soc.* 2012, 134, 17428-17431) (0.010 g, 0.027 mmol) and a solution of DMF:$H_2O$ (2 mL, 1:1). To this mixture was added a solution of copper(II) sulfate (0.001 g, 0.001 mmol) in $H_2O$ (100 μL) followed by a solution of sodium ascorbate (0.001 g, 0.005 mmol) in $H_2O$ (100 μL) and stirred for 18 h. The mixture was purified by reverse phase HPLC purified using a gradient method of 10% to 90% Acetonitrile/$H_2O$ with 0.5% TFA. The desired fractions were collected, frozen and lyophilized to afford 14 mg of the title compound (58%). Yield: 0.014 g. MS (+): calculated for $C_{49}H_{39}N_5O_{11}S^+$; Exact Mass: 888.23; Molecular Weight: 888.92. UPLC/MS measured (M)+888.46.

Example 55

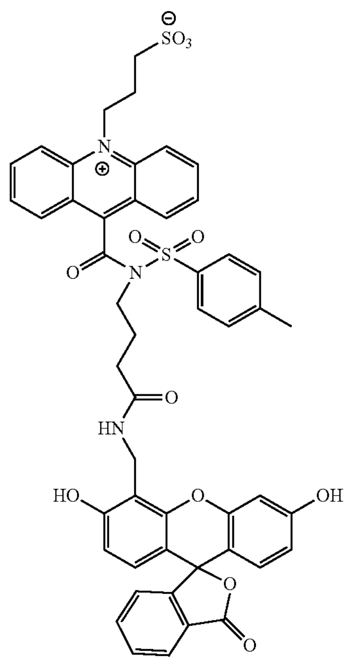

A 25 mL RB flask equipped with a stir bar and nitrogen inlet was charged with CPSP (0.020 g, 0.034 mmol), HBTU (0.014 g, 0.037 mmol), HOBt (0.005 g, 0.037 mmol) and DMF (2 mL). To this mixture was added DIEA (0.030 mL, 0.171 mmol) and stirred for 30 min. To this mixture was added 4'-aminomethylfluorescein (U.S. Pat. No. 4,510,251, 1985) (0.034 g, 0.094 mmol) and stirred for 18 h. The mixture was concentrated in vacuo. The residue was purified by reverse phase HPLC using a gradient method of 10% to 90% Acetonitrile/$H_2O$ with 0.5% TFA. The desired fractions were collected, frozen and lyophilized to afford 0.010 g of the title compound as a yellow-orange solid (32%). Yield: 0.010 g of a yellow-orange solid. MS (+): calculated for $C_{49}H_{41}N_3O_{12}S_2^+$; Exact Mass: 927.21; Molecular Weight: 928.00. UPLC/MS measured (M)+928.50.

Example 56

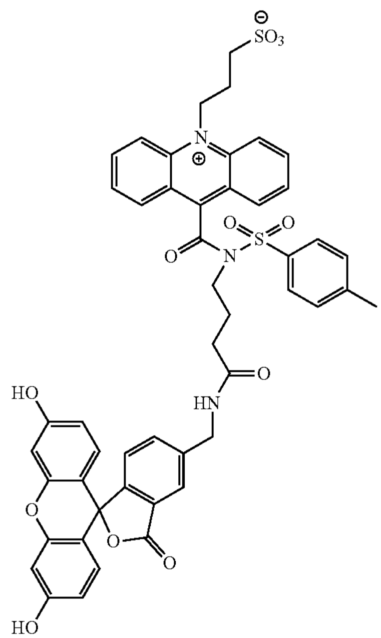

A 25 mL RB flask equipped with a stir bar and nitrogen inlet was charged with CPSP (0.050 g, 0.086 mmol), HBTU (0.036 g, 0.094 mmol), and HOBt (0.013 g, 0.094 mmol) and DMF (2 mL). To this mixture was added DIEA (0.074 mL, 0.428 mmol) and the reaction was stirred for 30 min. To this mixture was added 5-aminomethylfluorescein (*Bioconjugate Chem.* 1992, 3, 430-431) (0.034 g, 0.094 mmol) and stirred for 18 h. The mixture was concentrated in vacuo. The residue was purified by reverse phase HPLC using a gradient method of 10% to 90% Acetonitrile/$H_2O$ with 0.5% TFA. The desired fractions were collected and lyophilized to afford 0.027 g of the title compound as a yellow-orange solid (34%). Yield: 0.027 g of a yellow-orange solid. MS (+): calculated for $C_{49}H_{41}N_3O_{12}S_2^+$; Exact Mass: 927.21; Molecular Weight: 928.00. UPLC/MS measured (M+H)+ 929.45.

Example 57

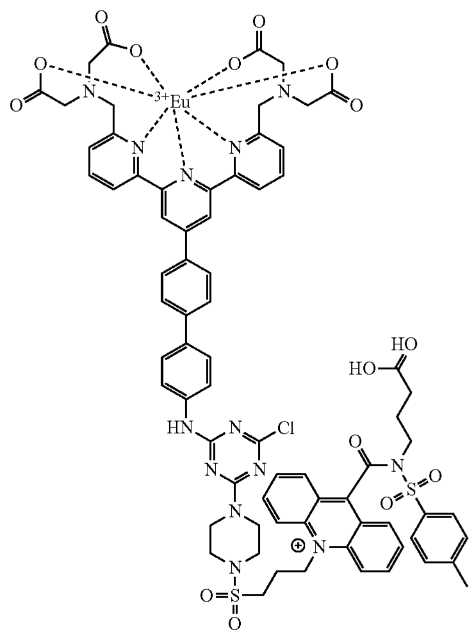

A 4 mL reaction vial equipped with a magnetic stir bar and nitrogen inlet was charged with 0.007 g (0.0072 mmol) of the product from Example 2, 0.003 g (0.003 mmol) of DTBTA-$Eu^{3+}$(*Inorg. Chem.,* 2006, 45, 4088-4096), DMF (0.5 mL), and DIEA (0.01 mL, 0.06 mmol). Reaction was stirred overnight before being diluted in a small amount of ACN/$H_2O$. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.05 formic acid. Fractions containing the product were combined and the volatile components were removed in vacuo on a rotary evaporator at 30° C. followed by high vacuum for 18 hours at room temperature. Yield 0.002 g of a light-yellow powder. MS (M+): calculated for $C_{72}H_{65}ClEuN_{13}O_{15}S_2^{4+}$; Exact Mass: 1603.3043; Molecular Weight: 1603.9198. UPLC/MS measured 1604.65.

Example 58

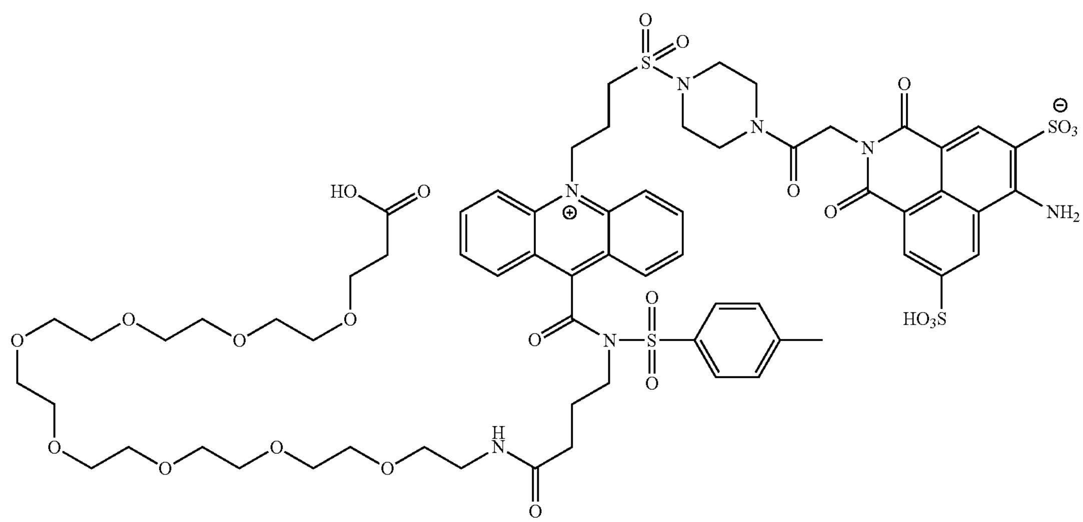

The titled compound was prepared using a similar procedure outlined for the preparation of Example 49 utilizing 0.011 g (0.0095 mmol) of the product from Example 48, 0.045 g (0.090 mmol) of Amino-dPEG®$_8$-t-butyl ester, DMF (0.5 mL), and DIEA (0.1 mL, 0.6 mmol). Yield: 0.006 g of yellow film. MS (−): calculated for $C_{65}H_{81}N_7O_{25}S_4$−; Exact Mass: 1487.4165; Molecular Weight: 1488.6270. UPLC/MS measured 1487.71.

Example 59

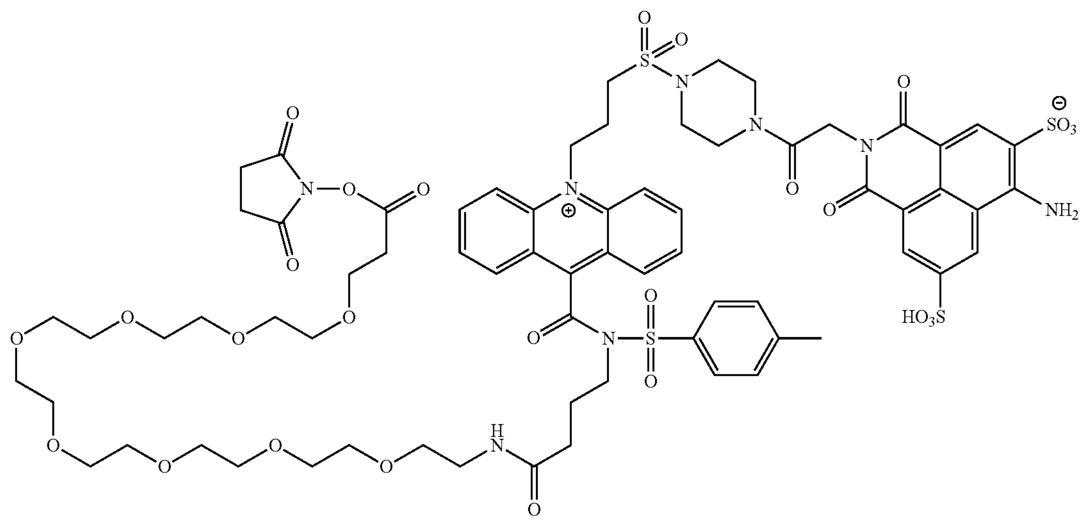

The titled compound was prepared using a similar procedure outlined for the preparation of Example 48 utilizing 0.006 g (0.0067 mmol) of the product from Example 58, 0.002 g (0.0067 mmol) of TSTU, DMF (0.5 mL), and DIEA (0.03 mL, 0.17 mmol). Yield: 0.004 g MS (−): calculated for $C_{69}H_{84}N_8O_{27}S_4$−; Exact Mass: 1584.4329; Molecular Weight: 1585.7000. UPLC/MS measured 1584.75.

Example 60

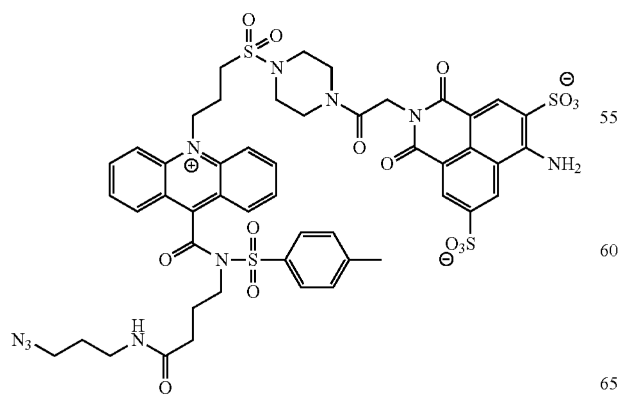

A 4 mL reaction vial equipped with a magnetic stir bar and nitrogen inlet was charged with 0.006 g (0.0052 mmol) of the product from Example 48, 0.025 g (0.25 mmol) of 3-azido-1-propanamine, DMF (0.5 mL), and DIEA (0.1 mL, 0.6 mmol). The mixture was stirred for 1 hour before being diluted in a small amount of ACN. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% formic acid. Fractions containing the product were combined and the volatile components were removed in vacuo on a rotary evaporator at 30° C. followed by high vacuum for 18 hours at room temperature. Yield: 0.003 g of yellow film. MS (−): calculated for $C_{49}H_{50}N_{10}O_{15}S_4$−; Exact Mass: 1145.2267; Molecular Weight: 1146.2265. UPLC/MS measured 1145.63.

Example 61

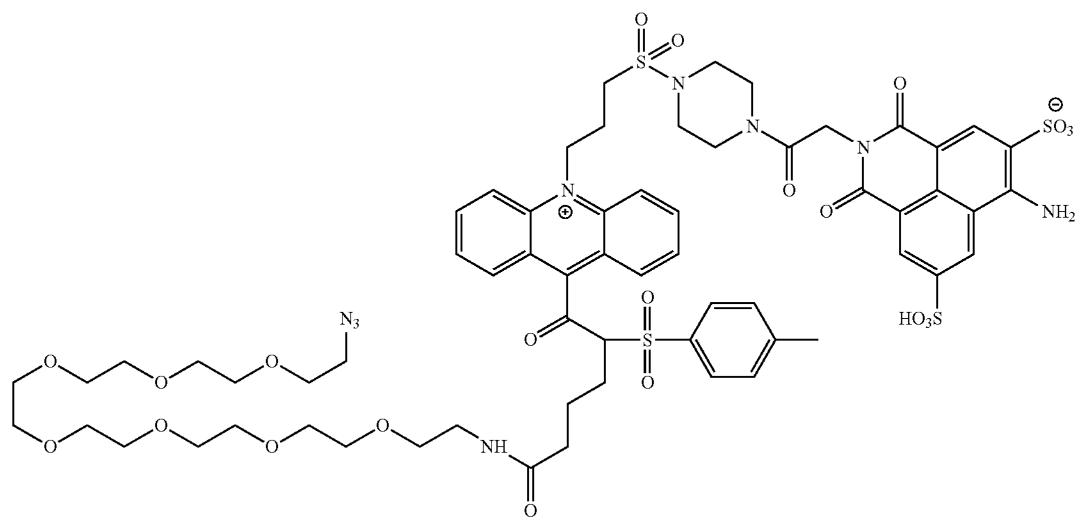

The titled compound was prepared using a similar procedure outlined for the preparation of Example 60 utilizing 0.006 g (0.0052 mmol) of the product from Example 48, 0.030 g (0.076 mmol) of azido-dPEG®7-amine, DMF (0.5 mL), and DIEA (0.1 mL, 0.6 mmol). Yield: 0.004 g of yellow film. MS (−): calculated for $C_{62}H_{76}N_{10}O_{22}S_4$; Exact Mass: 1440.4018; Molecular Weight: 1441.5780. UPLC/MS measured 1440.82.

Example 62

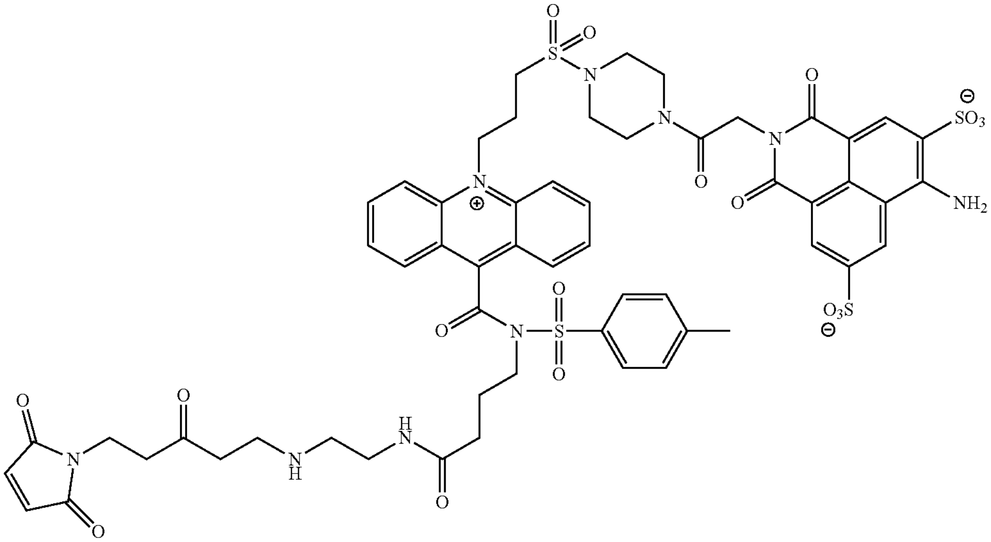

The titled compound was prepared using a similar procedure outlined for the preparation of Example 60 utilizing 0.0075 g (0.0065 mmol) of the product from Example 48, 0.020 g (0.076 mmol) of MPS-EDA (Quanta Biodesign), DMF (0.5 mL), and DIEA (0.1 mL, 0.6 mmol). Yield: 0.002 g of yellow film. MS (−): calculated for $C_{55}H_{54}N_9O_{18}S_4-$; Exact Mass: 1256.2475; Molecular Weight: 1257.3225. UPLC/MS measured 1256.53

Example 63

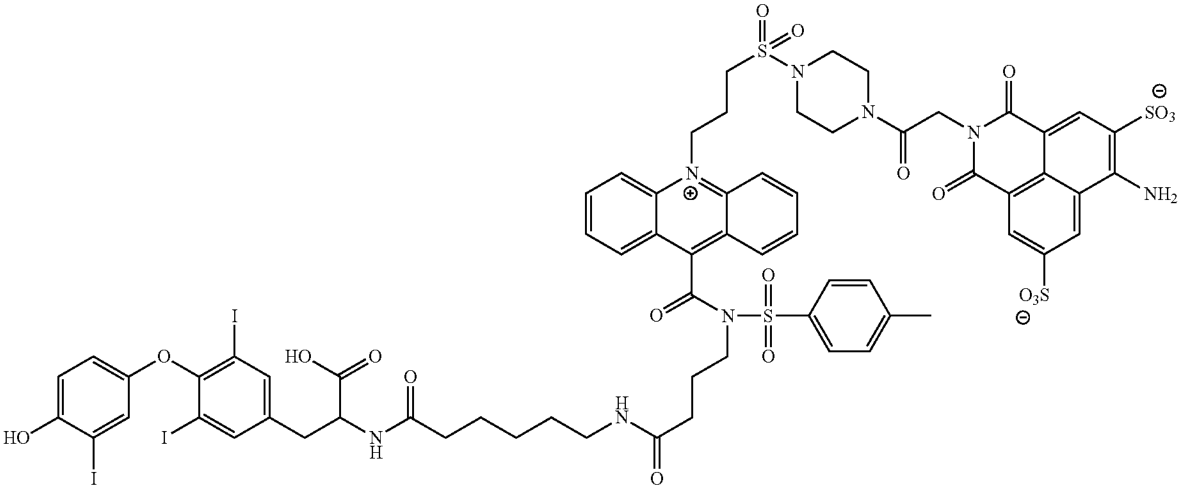

The titled compound was prepared using a similar procedure outlined for the preparation of Example 60 utilizing 0.006 g (0.0052 mmol) of the product from Example 48, 0.005 g (0.0067 mmol) of 2-(6-aminohexanamido)-thyroxine (*Bioconjugate Chem.* 1997, 8, 133-145), DMF (0.5 mL), and DIEA (0.01 mL, 0.06 mmol). Yield: 0.005 g of yellow film. MS (−): calculated for $C_{67}H_{65}I_3N_8O_{20}S_4-$; Exact Mass: 1810.0332; Molecular Weight: 1811.2464. UPLC/MS measured 1810.59 (weak); $M^{2-}$904.99 (strong).

Example 64

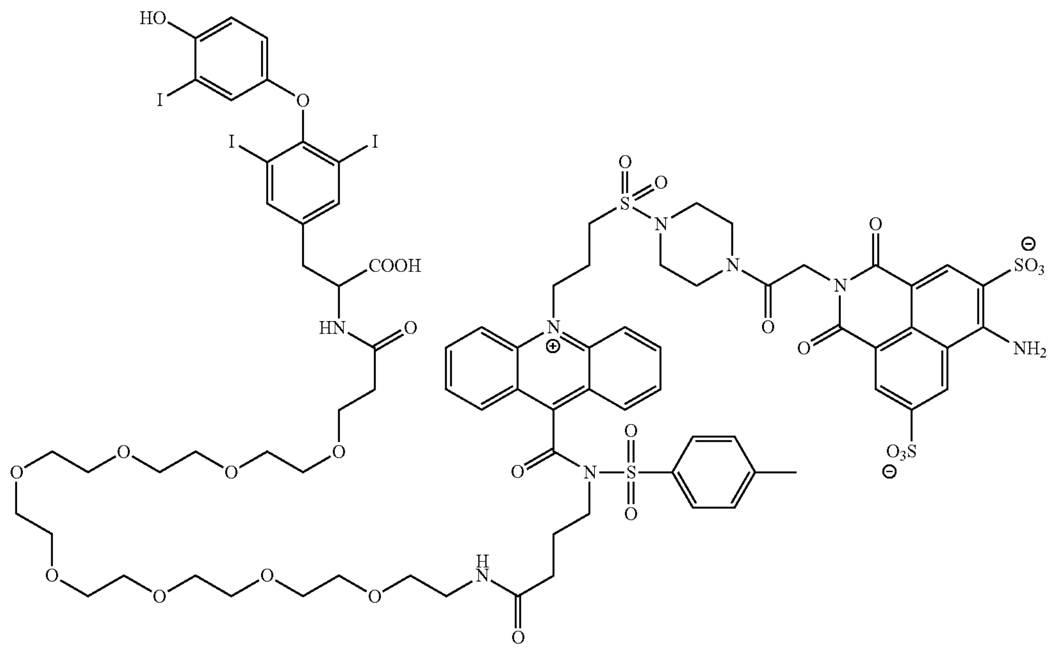

A 4 mL reaction vial equipped with a magnetic stir bar and nitrogen inlet was charged with 0.004 g (0.0025 mmol) of the product from Example 59, 0.0082 g (0.013 mmol) of thyroxine, DMF (0.5 mL), and DIEA (0.01 mL, 0.06 mmol). The mixture was stirred for 1 hour before being diluted in a small amount of ACN. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% formic acid. Fractions containing the product were combined and the volatile components were removed in vacuo on a rotary evaporator at 30° C. followed by high vacuum for 18 hours at room temperature. Yield: 0.002 g of yellow film. MS (−): calculated for $C_{80}H_{90}I_3N_8O_{28}S_4^-$; Exact Mass: 2119.1887; Molecular Weight: 2120.5820. UPLC/MS measured $M^{2-}$1059.82

Example 65

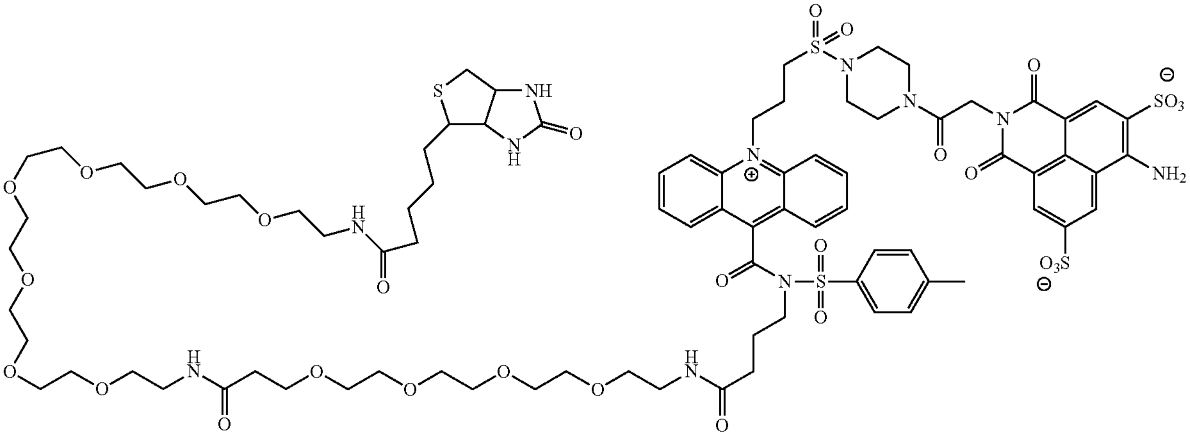

The titled compound was prepared by treating a solution of Example 50, (0.0018 g, 0.0013 mmol) in DMF (0.25 mL) with a solution of biotin-dPEG7-NH2 (Quanta BioDesign catalog #10826, 0.030 g, in DMF (1 mL). The reaction was stirred for 1 hour at room temperature. The resulting solution was purified by reverse phase HPLC using a YMC ODS AQ 30×150 mm I.D. steel column with a Waters Separations 2000 system monitored at 254 nm. Recorder chart speed 5 mm/min. A manual step gradient method (flow rate 40 mL/min) was used ACN/H2O/H2O-0.5 TFA. Fractions containing the product were combined and the volatile components were removed in vacuo on a rotary evaporator at 30° C. followed by high vacuum for 18 hours at room temperature. Yield 0.0024 g of a yellow film. MS (−): calculated for $C_{83}H_{112}N_{11}O_{29}S_5-$; Exact Mass: 1886.6236; Molecular Weight: 1888.16. UPLC/MS measured 1887.59.

Example 66

Chemiluminescence Data

Protocol for measurement of full chemiluminescence spectrum in the visible wavelength range. Equipment: ANDOR® Shamrock 303i imaging spectrograph, 50 lines/mm ruled grating, 600 nm blaze, aluminum with MgF2 coating, 100 μm entrance slit. ANDOR® iXon$^{EM}$+512×512 CCD camera, model DU-897E-CSO-#BV, back illuminated sensor with 550 nm AR coating. CCD detector chip is E2V Tech CCD97 with electron multiplying readout, with 16 $\mu m^2$ pixel. Thermoelectric cooling was to −70° C. Pixel (column) binning along the vertical (image of slit) for maximum sensitivity was selected covering most of the extent of the chip. Detection wavelength was calibrated using the spectrograph's software by several mercury lines of an Ar—Hg pen lamp, and the resulting spectral dispersion at the detector was approximately 1 nm/pixel. Integration was 5 seconds, which is usually about 5 decay lifetimes of chemiluminescence. Software: ANDOR® Solis for Spectroscopy: X3964, version 4.3. Reagents: ARCHITECT® pretrigger solution, 6E23-65, with detergent, acid, and hydrogen peroxide; ARCHITECT® trigger solution, $6C_{55-60}$, with detergent and base. Method: A Hi-Tech Rapid Kinetics Accessory, model SFA-11 was used to mix solutions in the chamber in less than 20 ms per the user manual. The software data acquisition was triggered by hotkey, and two 2.5 mL syringes were pushed manually to achieve 50:50 mixing in the cuvette. The delay from start of integration to mixing was estimated as less than 0.5 sec. The cuvette was oriented giving a 2 mm path length. Samples were typically tested at 500 nanomolar concentration as determined by UV absorbance at the appropriate wavelength per fluorophore.

Protocol for luminometer plate reader measurement of chemiluminescence at multiple wavelengths. Equipment: Berthold Mithras LB940 microplate reader; Optical filters, Semrock Brightline single-band bandpass, multilayer dielectric, 442/46 nm, 531/46 nm; White 96-well plate, MICROFLUOR® I, Thermo 6905. Software: Mikrowin 2000 v. 4.41. Reagents: ARCHITECT® pretrigger solution, 6E23-65, with detergent, acid, and hydrogen peroxide; ARCHITECT® trigger solution, $6C_{55-60}$, with detergent and base. 50 μL of test compound in ARCHITECT® Pretrigger solution was placed in a well of the 96-well plate, separate wells were filled for each wavelength measurement. Method: Samples were typically tested at 20-200 pM concentration as determined by absorbance at the appropriate wavelength per fluorophore. In the luminometer, an optical filter of the appropriate wavelength was chosen for the readout. 75 μL of ARCHITECT® Trigger solution was injected into each well just prior to detection. Light counts were measured by the photomultiplier tube with 0.1 sec intervals over 10 sec. Readings were measured in triplicate. Results of the above assays are presented in Table 1.

TABLE 1

| Chemiluminescence Data | | | | |
|---|---|---|---|---|
| Compound | Emission Wavelength Maximum** | Emission 400-500 nm Region | Emission 500-800 nm Region | Relative Intensity† |
| Example 12 | 535 nm | 1% | 99% | 87%‡ |
| Example 13 | 535 nm | 1% | 99% | 40%‡ |
| Example 14 | 532 nm | 3% | 97% | 264% |
| Example 15 | 527 nm | 3% | 97% | 325% |
| Example 16 | 580 nm | 5% | 95% | 324% |
| Example 17 | 525 nm | 3% | 97% | 57% |
| Example 18 | 587 nm | 3% | 97% | 114% |
| Example 19 | 530 nm | 3% | 97% | 297% |
| Example 20 | 530 nm | 2% | 98% | 255% |
| Example 21 | 528 nm | 3% | 97% | 240% |
| Example 22 | 531 nm | 3% | 97% | 291% |
| Example 23 | 532 nm | 2% | 98% | 284% |
| Example 24 | 529 nm | 3% | 97% | 133% |
| Example 25 | 586 nm | 23% | 77% | 98% |
| Example 26 | 526 nm | 18% | 82% | 331% |
| Example 27 | 524 nm | 3% | 97% | 280% |
| Example 28 | 535 nm | 1% | 99% | n.d. |
| Example 29 | 508 nm | 9% | 91% | 165% |
| Example 30 | 574 nm | 9% | 91% | 151% |
| Example 31 | 514 nm | 5% | 95% | 210% |
| Example 32 | 624 nm | 3% | 97% | 207% |
| Example 33 | 557 nm | 40% | 60% | 57% |
| Example 34 | 521 nm | 13% | 87% | 81% |
| Example 35 | 601 nm | 2% | 98% | 167% |
| Example 37 | 439 nm (676 nm) | 87% | 13% | 58% |
| Example 39 | 518 nm | 7% | 93% | 231% |
| Example 40 | 534 nm | 1% | 99% | 334% |
| Example 41 | 560 nm | 10% | 90% | 161% |
| Example 42 | 720 nm | 16% | 84% | 116% |
| Example 44 | 441 nm (817 nm) | 96% | 4% | 37% |
| Example 45 | 537 nm | 9% | 91% | 86% |
| Example 47 | 532 nm | 9% | 91% | 72% |
| Example 54 | 535 nm | 3% | 97% | 37%‡ |
| Example 55 | 440 nm (n.d.) | 94% | 6% | 70%‡ |
| Example 56 | 440 nm (n.d.) | 95% | 5% | 71%‡ |
| Example 57 | 614 nm* | 49% | 51% | 118%‡ |

†Relative total light output from 400-800 nm of the example compound in comparison to CPSP acridinium at a similar concentration (based on literature extinction coefficients of the fluorophore only) as measured by the Andor Shamrock 303i imaging spectrograph, unless otherwise noted. The calculation does not consider differences in measurement efficiency of the CCD camera across the wavelength span or changes in extinction coefficient of the fluorophores when directly linked to acridinium. The calculation was made to simply compare individual compounds within the series shown. Measurements were performed in Architect Pretrigger and Trigger solutions (see methods description).

†Noted measurements were performed on a Berthold Mithras LB940 microplate reader luminometer.

*Four peaks were observed representative of Europium complex photon emission (590, 614, 650, and 690 nm)

**Emission Wavelength maximum listed in parenthesis denote the wavelength of the shifted-emission band observed when the shifted band was not the maximum emission band.

n.d. = not determined

Example 67

Fluorophore attachment point and linker length were examined using an acetamide linker and isolated 5 and 6 carboxy isomers of fluorescein. The data, shown in FIG. 1, demonstrate that shifted emission is dictated by fluorophore attachment point which may lead to differing overall orientation of the two species or species aggregation, and altered ability to shift emission in the short linker configuration.

The 5 and 6 carboxy isomers of fluorescein were further examined using a piperazine linker. Data are shown in FIG.

2. Shifted emission was observed at near 100% efficiency, however differences in intensity were noted between the 5 and 6-isomer moieties. Intensity differences may be attributed to hinderance of the chemical reaction which drives chemiluminescence, an unfavorable orientation possibly leading to quenching or a non-radiative decay pathway, or compound aggregation leading to altered absorbance/emission profiles. These results illustrate that selection of fluorophore attachment point is an important factor for shifted emission.

Figure 3:
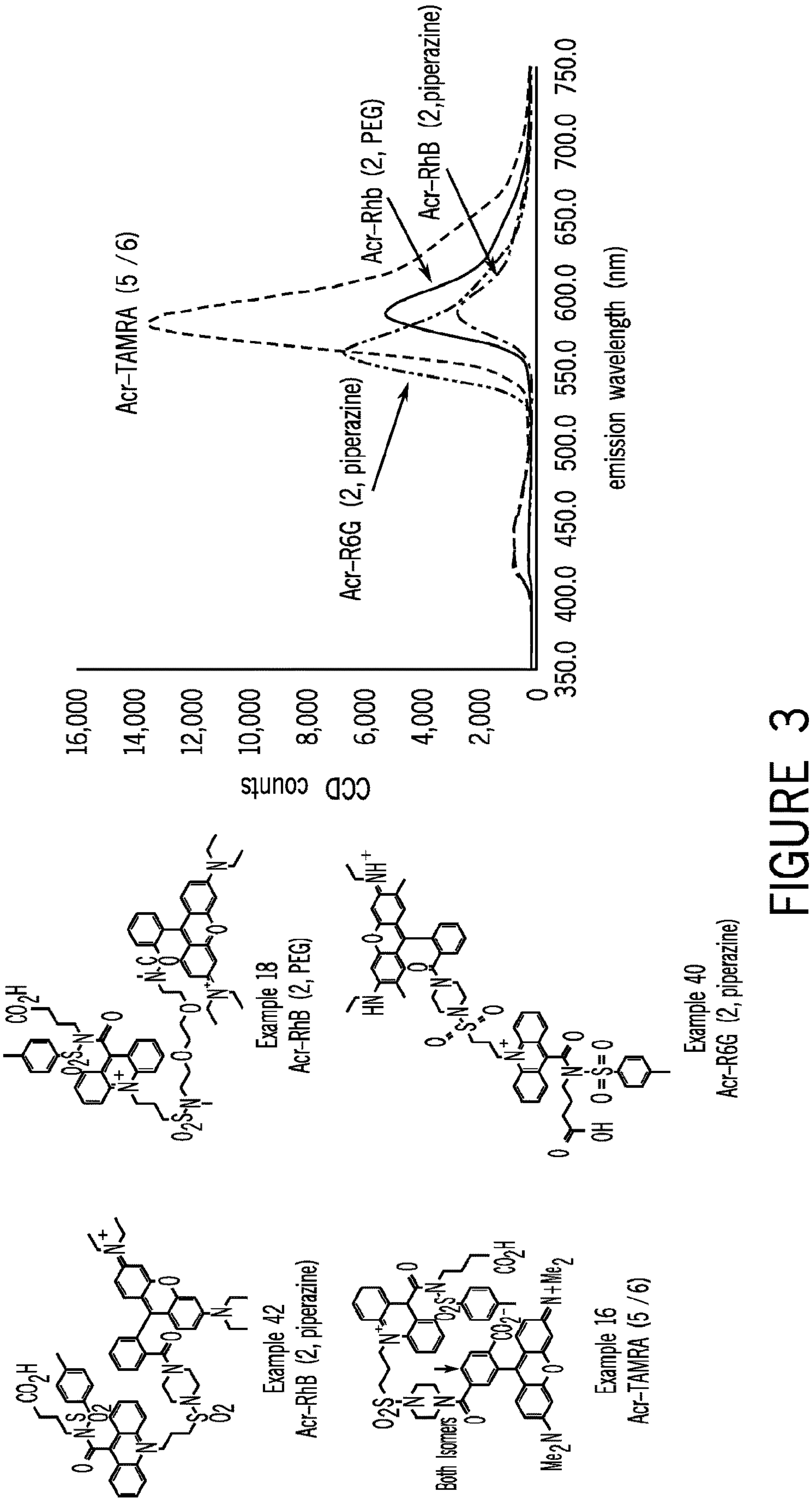
FIG. 3 shows structures and fluorescence data for 5/6-carboxy and 2-carboxy isomers of rhodamine attached to a substituted acridinium moiety via various linkers.

Fluorophore attachment point and linker length were also examined for emission efficiency using both a 5/6 carboxy rhodamine dye mixture and a 2 carboxy rhodamine dye. Data are shown in FIG. 3. The 5/6 carboxy rhodamine showed efficient shifted emission while the 2 carboxy rhodamine showed efficient shifted emission in most circumstances with some discrepancies depending on linker type. For example, 2-carboxy Rhodamine B showed efficient stable shifted emission when linked to acridinium through a dimethyl-PEG(2)-diamine linker while the same 2-carboxy Rhodamine B showed increasing levels of acridone emission within the measuring interval when linked to acridinium through a piperazine linkage. These findings indicate the construct may not be stable under the triggering conditions employed. In contrast, 2 carboxy Rhodamine 6G appeared to produce stable shifted emission when linked to acridinium through a piperazine linkage, although shifted emission was only 90% with 10% blue light observed.

Figure 4:
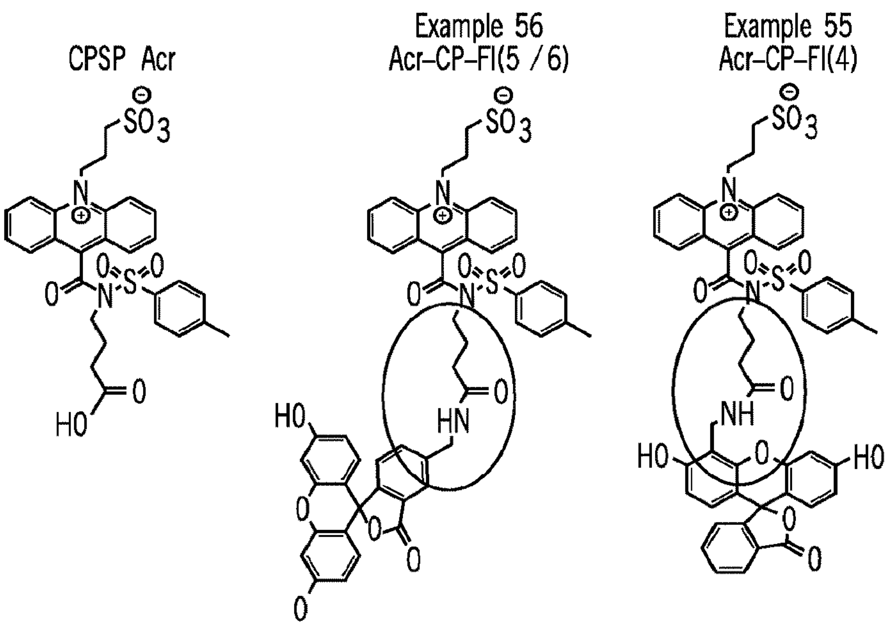
FIG. 4 shows structures and emission data for substituted acridinium moieties linked to fluorophores via a different attachment point.

Initiator attachment point was examined by varying the position of the fluorophore between the sulfopropyl moiety to that of the carboxypropyl moiety of carboxypropyl sulfopropyl acridinium. Attachment to the carboxypropyl group positions the fluorophore on the leaving group of acridinium/acridone molecule. Therefore, on triggering, the fluorophore would dissociate from the resulting acridone moiety. Two fluorescein compounds were attached to acridinium via a xanthene ring attachment point or a phenyl ring attachment point to examine two different molecular orientations. Emission was measured on a luminometer fitted with 442 nm and 531 nm filters. Data are shown in FIG. 4. The fluorescein compounds prepared with carboxypropyl initiator attachment failed to show shifted emission and produced similar wavelength light to that of an acridinium control. Carboxy propyl modification with the preferred piperazine linkage was also attempted and resulted in emission similar to an acridinium control. FIG. 4 shows that the light output and distribution in each filter channel matched that of an acridinium control compound for a selection of the prepared carboxy propyl compounds.

Linker type and linker length were examined using diamine linkers of various length and rigidity. A rigid linker may hold the initiator and acceptor in an orientation favorable for shifted emission while the longer linker has the flexibility to bend and twist into a favorable orientation. Data are shown in FIG. 5. Shifted emission was observed at near 100% efficiency for each of the compounds. However, a difference in intensity was noted for the ethylenediamine linker. Intensity differences may be attributed to hinderance of the chemical reaction which drives chemiluminescence, or an unfavorable orientation possibly leading to quenching or a non-radiative decay pathway. These data illustrate that selection of linker may be an important factor for shifted emission.

This example demonstrates that several structural factors are important in developing chemiluminescent acridinium compounds with shifted wavelength emission. The stability of fluorophores to triggering conditions is of significant importance. For example, linkage of cyanine and silicon rhodamine dyes to acridinium resulted in brief shifted emission followed by acridone emission indicating possible construct instability in the triggering matrix. Water solubility is another element needed for function in aqueous based usage such as immunoassays. Overall, selection of linker length, fluorophore attachment point, and initiator attachment drive shifted emission. Without wishing to be limited by theory, these three criteria appear to dictate fluorophore and initiator orientation relative to one another and therefore efficiency of shifted emission.

Example 68

HIV p24 mAb—Acridinium-Lucifer Yellow Conjugate. A stock solution of compound from Example 48 was prepared by reconstituting the dried powder in dimethyl sulfoxide (DMSO). Two 100× dilutions of the stock solution were prepared using a pH 5.5 MES buffer. Concentration was determined by reading absorbance at 370 nm using a Cary 60 UV-Vis spectrophotometer.

Approximately 0.3 mg of HIV p24 mAb was added to 35 μL of 10 mM phosphate buffered saline (PBS) and the pH was adjusted using 5 μL of spiking buffer (250 mM PBS with 7.5% CHAPS, pH 8) to achieve a final reaction pH of 7.5 and a final CHAPS concentration of 0.5% in separate reaction vessels. The vessels were protected from light and the compound from Example 48 stock solution was added to each reaction vessel to achieve a molar input ratio of 6, 9, or 12 over moles of mAb. The reaction vessels were lightly vortexed and then statically incubated overnight, approximately 20 hours, protected from light. After this time, the reaction vessels were centrifuged to separate insoluble aggregates and the protein remaining in the supernatant was was purified by HPLC on a TSKGel G3000SWxl column with a mobile phase of 10 mM PBS pH 6.3. A flow rate of 1 mL/min was used and the eluent was monitored with a Photodiode array detector at 280 nm, 370 nm, and 431 nm. Protein and Example 48 label concentrations were determined by UV-Vis (280 and 370 nm, respectively). Label to protein incorporation ratio (IR) was determined by dividing the molar concentration of Example 48 to that of the HIV mAb. Final IR values of 2.0, 2.5, and 3.0 were achieved for the 1:6, 1:9, 1:12 molar input ratios, respectively. Protein conjugates were stored at 2-8° C. protected from light until time of use.

Label to protein incorporation ratio was determined by dividing the corrected A280 concentration (A280 absorbance minus A280 contribution of acridinium) by the A370 absorbance of acridinium. Protein conjugates were stored at 2-8° C. until time of use.

Example 69

Anti-Human IgM mAb—Acridinium-Lucifer Yellow Conjugate. A stock solution of compound from Example 48 was prepared by reconstituting the dried powder in DMSO. Two 100× dilutions of the stock solution were prepared using a pH 5.5 MES buffer. Concentration was determined by reading absorbance at 370 nm using a Cary 60 UV-Vis spectrophotometer.

Approximately 0.3 mg of Anti-Human IgM mAb was added to 35 μL of 10 mM phosphate buffered saline (PBS) and the pH was adjusted using 5 μL of spiking buffer (250 mM PBS with 7.5% CHAPS, pH 8) to achieve a final reaction pH of 7.5 and a final CHAPS concentration of 0.5%. The vessel was protected from light and compound from Example 48 stock solution was added to achieve a molar input ratio of 8.5 over moles of mAb. The reaction vessel was lightly vortexed and then statically incubated for 5 hours, protected from light. After this time, the reaction vessel was centrifuged to separate insoluble aggregates and the protein remaining in the supernatant was purified by HPLC on a TSKGel G3000SWxl column with a mobile phase of 10 mM PBS pH 6.3. A flow rate of 1 mL/min was used and the eluent was monitored with a Photodiode array detector at 280 nm, 370 nm, and 431 nm. Protein and Example 48 label concentrations were determined by UV-Vis (280 and 370 nm, respectively). Label to protein incorporation ratio (IR) was determined by dividing the molar concentration of Example 48 to that of the HIV mAb. A final IR value of 2.6 was achieved for the 1:8.5 molar input ratio. Protein conjugate was stored at 2-8° C. protected from light until time of use.

Example 70

Anti-Human IgG mAb—Acridinium-Fluorescein Conjugate. A stock solution of active ester compound from Example 12 was prepared by reconstituting the dried powder in DMSO to 5 mg/mL by dry weight.

Approximately 2 mg of anti-Human IgG antibody was added to approximately 890 μL of 10 mM phosphate buffered saline pH 8.0 in separate reaction vessels. The vessels were protected from light and active ester of Example 12 solution was added to each reaction vessel to achieve a molar input ratio of 3, 5, or 7 over moles of mAb. The reaction vessels were lightly vortexed and then statically incubated overnight, approximately 16 hours, protected from light. After this time, the reaction vessels were centrifuged to separate insoluble aggregates and the protein remaining in the supernatant was desalted using PD10 G25 desalting columns with a mobile phase of 10 mM PBS pH 6.3. Triggerable counts were measured by adding 70 ng/mL conjugate to ARCHITECT® Pre-Trigger and Trigger on a Mithras LB 940 luminometer. Protein conjugates were stored at 2-8° C. protected from light until time of use.

Example 71

HIV p24 mAb—Acridinium-Fluorescein Conjugate. A 10 mg/mL stock solution of DBCO-PEG-NHS (Click Chemistry Tools A134) was prepared by reconstituting the dried powder in dimethyl sulfoxide (DMSO). The HIV p24 mAb was desalted using a zeba spin column and the antibody concentration was determined by UV-Vis absorbance at 280 nm. The reaction vessel was protected from light and the DBCO solution was added to achieve a molar input ratio of 8 over moles of mAb. The reaction vessel was lightly vortexed and then statically incubated overnight (approximately 20 hours). The resulting solution as purified by HPLC. The DBCO-antibody concentration was again determined by UV-Vis absorbance at 280 nm. A stock solution of the azide compound from Example 12 was prepared at 3.2 pM by dry weight in DMSO. The DBCO-antibody was reacted with the Example 12 azide by incubating 50 μL DBCO-antibody solution with 50 μL Example 12 azide solution in a reaction vessel protected from light overnight (20 hours) at room temperature. Label to protein incorporation ratio (IR) was determined by dividing the molar concentration of Example 12 to that of the HIV mAb. A final IR value of approximately 2.0 was achieved. Protein conjugate was stored at 2-8° C. protected from light until time of use.

Example 72

HIV p24 mAb—Acridinium-BODIPY 493 Conjugate. A stock solution of compound from Example 51 was prepared by reconstituting the dried powder in DMSO. Two 100× dilutions of the stock solution were prepared using a pH 5.0 MES buffer. Concentration was determined by reading absorbance at 370 nm using a Cary 60 UV-Vis spectrophotometer.

Approximately 0.3 mg of HIV p24 mAb was added to approximately 40 μL of 10 mM phosphate buffered saline (PBS) in separate reaction vessels. The vessels were protected from light and compound from Example 51 stock solution was added to each reaction vessel to achieve a molar input ratio of 5, 10, or 15 over moles of mAb. The reaction vessels were lightly vortexed and then statically incubated overnight, approximately 16 hours, protected from light. After this time, the reaction vessels were centrifuged to separate insoluble aggregates and the protein remaining in the supernatant was purified by HPLC on a TSKGel G3000SWxl column with a mobile phase of 10 mM PBS pH 6.3. A flow rate of 1 mL/min was used and the eluent was monitored with a Photodiode array detector at 280 nm, 370 nm, and 431 nm. Protein and Example 51 label concentrations were determined by UV-Vis (280 and 370 nm, respectively). Label to protein incorporation ratio (IR) was determined by dividing the molar concentration of Example 51 to that of the HIV mAb. The soluble conjugate aggregates produced IR values of 8.8, 7.9, and 8.4 for the 1:5, 1:10, 1:15 molar input ratios, respectively, representing a saturation point for IR with the input ratios investigated. Protein conjugates were stored at 2-8° C. protected from light until time of use.

Example 73

HIV p24 mAb—Acridinium-BODIPY TEXAS RED (TR) Conjugate. A stock solution of compound from Example 52 was prepared by reconstituting the dried powder in DMSO. Two 100× dilutions of the stock solution were prepared using a pH 5.5 MES buffer. Concentration was determined by reading absorbance at 370 nm using a Cary 60 UV-Vis spectrophotometer.

Approximately 0.3 mg of HIV p24 mAb was added to approximately 7.5 μL of 10 mM phosphate buffer in separate reaction vessels. The vessels were protected from light and compound from Example 52 stock solution was added to each reaction vessel to achieve a molar input ratio of either 1:10. DMSO was added in increasing amounts up to 30% reaction volume to help solubilize the Example 52 compound. The final reaction volume was 25 μL. The reaction vessels were lightly vortexed and then statically incubated overnight, approximately 16 hours, protected from light. After this time, the reaction vessels were centrifuged to separate insoluble aggregates and the protein remaining in the supernatant was purified by HPLC on a TSKGel G3000SWxl column with a mobile phase of 10 mM PBS pH 6.3. A flow rate of 1 mL/min was used and the eluent was monitored with a Photodiode array detector at 280 nm, 370 nm, and 431 nm. Soluble aggregates were observed and isolated for further testing. Protein conjugates were stored at 2-8° C. protected from light until time of use.

Example 74

HIV p24 mAb—PEG-Acridinium-Lucifer Yellow Conjugate. A stock solution of compound from Example 50 was prepared by reconstituting the dried powder in DMSO. Two 100× dilutions of the stock solution were prepared using a pH 5.5 MES buffer. Concentration was determined by reading absorbance at 370 nm using a Cary 60 UV-Vis spectrophotometer.

Approximately 0.3 mg of HIV p24 mAb was added to 35 μL of 10 mM phosphate buffered saline (PBS) and the pH was adjusted using 5 μL of spiking buffer (250 mM PBS with 7.5% CHAPS, pH 8) to achieve a final reaction pH of 7.5 and a final CHAPS concentration of 0.5%. The vessel was protected from light and compound from Example 50 stock solution was added to the reaction vessel to achieve a molar input ratio of 20 over moles of mAb. The reaction vessel was lightly vortexed and then statically incubated overnight, approximately 16 hours, protected from light. After this time, the reaction vessel was centrifuged to separate insoluble aggregates and the protein remaining in the supernatant was purified by HPLC on a TSKGel G3000SWxl column with a mobile phase of 10 mM PBS pH 6.3. A flow rate of 1 mL/min was used and the eluent was monitored with a Photodiode array detector at 280 nm, 370 nm, and 431 nm. Protein and Example 50 label concentration was determined by UV-Vis (280 and 370 nm, respectively). Label to protein incorporation ratio (IR) was determined by dividing the molar concentration of Example 50 to that of the HIV mAb. A final IR value of 4.0 was achieved for the 1:20 molar input ratio. Protein conjugates were stored at 2-8° C. protected from light until time of use.

Example 75

Anti-human IgG MAB—Lucifer Yellow-CPSP-PEG4 Acridinium Conjugate. A stock solution of Lucifer Yellow-CPSP-PEG4 active ester (Example 50) was prepared by reconstituting the dried powered in DMSO to 9.3 mg/mL.

Approximately 1 mg of anti-Human IgG mAb was dialyzed against 50 mM potassium phosphate 150 mM potassium chloride pH 8.0 at a ratio of 0.2 L/mL. After dialysis, 0.7 mg of antibody was added to 60 μL of potassium phosphate buffer containing cyclodextrin (30% in reaction), pH 8.0 in a light protected reaction vessel. Lucifer Yellow-CPSP-PEG4 acridinium solution was added to the reaction vessel to achieve a molar input ratio of 10 over moles of mAb. The reaction vessel was lightly vortexed and incubated statically overnight, approximately 22 hours, protected from light. The reaction vessel was centrifuged to separate insoluble aggregates and the remaining supernatant was purified via SEC-HPLC on a G3000 column with a mobile phase of 10 mM PBS pH 6.3. The conjugate IR was determined via UV-VIS, measuring A280 and A370. The protein conjugate was stored at 2-8° C.

Example 76

Anti-TSH MAB—Lucifer Yellow-CPSP-PEG4 Acridinium Conjugate. A stock solution of Lucifer Yellow-CPSP-PEG4 active ester (Example 50) was prepared by reconstituting the dried powered in DMSO to 9.3 mg/mL.

Approximately 3 mg of anti-TSH mAb was desalted over Zeba desalting columns into phosphate buffer pH 8.0. After desalting, 2.6 mg of antibody was added to 200 μL of phosphate buffer containing cyclodextrin (30% in reaction), pH 8.0 in a light protected reaction vessel. Lucifer Yellow-CPSP-PEG4 acridinium solution was added to the reaction vessel to achieve a molar input ratio of 7.5 over moles of mAb. The reaction vessel was lightly vortexed and incubated statically overnight, approximately 18 hours, protected from light. The reaction vessel was centrifuged to separate insoluble aggregates and the remaining supernatant was purified via SEC on a Sephacryl 5-300 column with a mobile phase of 10 mM PBS pH 6.3. The conjugate IR was determined via UV-VIS, measuring A280 and A370. The protein conjugate was stored at 2-8° C.

Example 77

Anti-NGAL mAb biotin-Acridinium-Lucifer Yellow (LY). A stock solution of biotin active ester (purchased) and acridinium lucifer yellow (Example 48) were prepared by reconstituting the dried powders in DMSO to 10 mg/mL by dry weight, separately.

Approximately 200 μg of anti-NGAL IgG antibody was added to approximately 100 μL of 10 mM phosphate buffered saline pH 8.0. The vessels were protected from light and active ester of biotin solution was added to achieve a molar input ratio of 5 times over moles of mAb. The reaction vessels were lightly vortexed and then statically incubated overnight, approximately 16 hours, protected from light. The solution was then loaded onto a desalting column (Zeba Spin desalting column from Thermo Scientifics). The concentration of the labeled antibody was determined by measuring the absorption spectrum at A280 nm. The extinction coefficient for A280 was 1.45/mg/mL. The purified protein was then reacted with active ester of acridinium-lucifer yellow at molar ratio of 1:0.5 (mAb:Acridinium-LY) for another 16 hours. The amount of acridinium-LY used in labeling was purposely kept low. It is preferable to remove the unreacted acridinium-LY with another desalting column, but the product can also be used without further purification. Protein conjugates were stored at 2-8° C. protected from light until time of use.

Example 78

Multiplexing Assay Evaluation—Cytomegalovirus (CMV) IgG and IgM Assay. CMV IgG and IgM antibody detection kits (Total CMV) were assembled by diluting an anti-Human IgG antibody—Acridinium-Fluorescein conjugate (70 ng/mL, Example 70) for CMV IgG antibody detection and an anti-Human IgM antibody—acridinium conjugate (25 ng/mL) for CMV IgM antibody detection in ARCHITECT® CMV IgG conjugate diluent containing MES buffer. The experimental conjugate bottle was paired with Abbott on-market CMV microparticles and assay specific diluent (ASD) (Abbott list number 6C15). Microparticle processing was performed using 96-well plates on a KingFisher instrument and luminescent reads were performed on a Mithras LB 940 luminometer. Briefly, a 96-well plate was prepared with microparticles, ASD, and sample in row 1 and incubated with shaking for approximately 18 minutes. Rows 2-4 were charged with 200 μL wash buffer and the particles were washed 3 times following sample incubation. Microparticles were transferred to row 5 containing conjugate and incubated for 4 minutes. Microparticles were washed an additional 3 times using 200 μL wash buffer in rows 6 through 8. Finally, microparticles were transferred to row 9 containing 100 μL ARCHITECT® pre-trigger and incubated for 5 minutes. Following incubation, 33 μL of reaction mixture was transferred to a fresh 96-well plate in triplicate and placed on the Mithras LB 940 luminometer. An injector on the luminometer was programed to dispense ARCHITECT® Trigger to each well followed by a 10 second chemiluminescent light collection with or without wavelength filters. Triplicate reaction wells were used to read with no filter, green filter, and blue filter. A 442/46 nm filter was used to capture blue light and an 531/46 nm filter was used to capture green light. Relative light units (RLU) reads for each well were generated by summing the total light output for the first 3 seconds of the read window.

Figure 6:
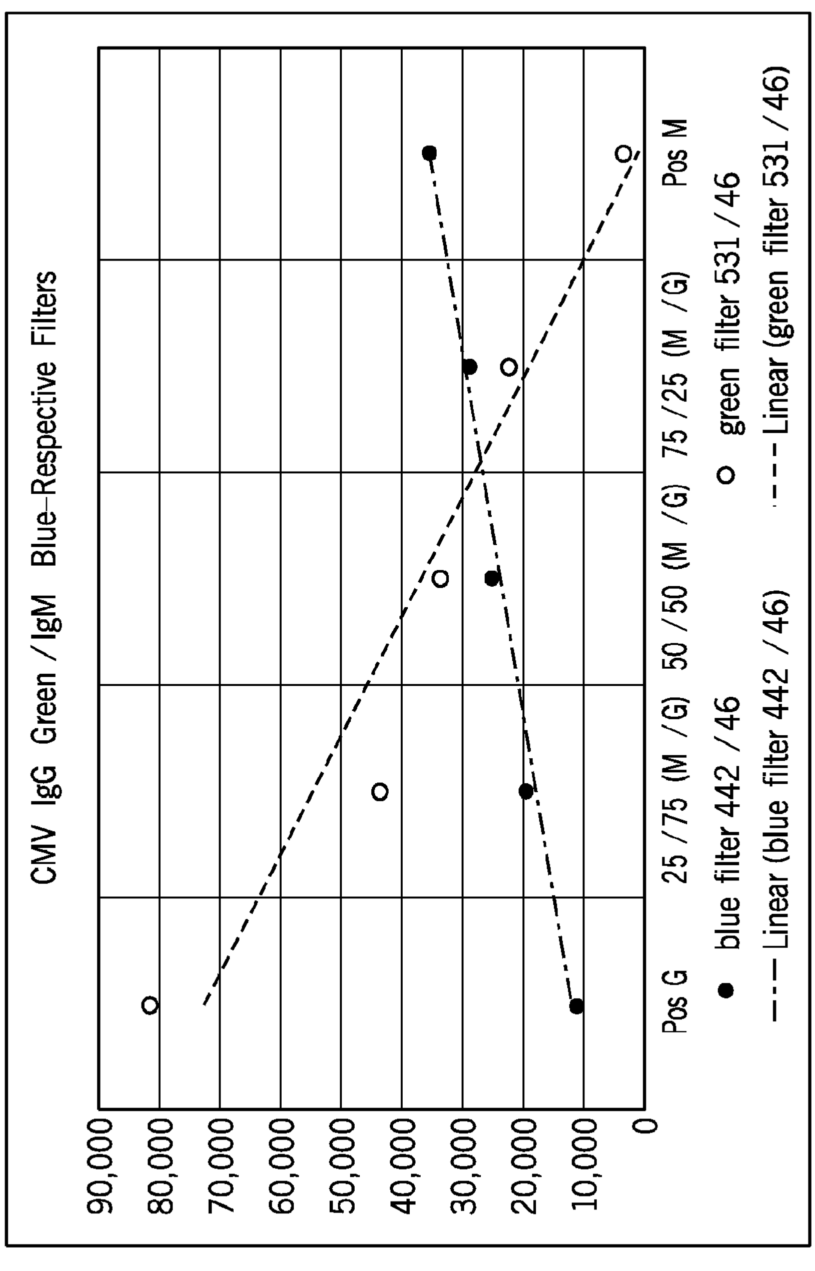
FIG. 6 shows results of a cytomegalovirus IgG and IgM multiplexing assay, as described in Example 78.

A multiplexing test was performed in which an CMV IgG only sample (ARCHITECT® CMV positive control) was combined with a known CMV IgM only containing sample in relative quantities. Samples were created containing IgM to IgG ratios of 0:100, 25:75, 50:50, 75:25, and 100:0. Signal produced with no filter, green filter, and blue filter was processed and analyzed. Results, shown in FIG. 6, demonstrated that the assembled reagent kit can differentiate mixed IgM and IgG signals in a single sample.

Example 79

Multiplexing Assay Evaluation—HIV Antigen and Antibody Combination Assay. HIV Antigen and Antibody detection kits (HIV Combo) were assembled by diluting an HIV p24 mAb—Acridinium-Fluorescein conjugate (125 ng/mL, Example 71) for HIV antigen detection and an HIV Antigen-Acridinium conjugate (50 ng/mL) for HIV antibody detection in ARCHITECT® HIV Combo conjugate diluent containing phosphate buffer, bovine serum albumin, and surfactants. The experimental conjugate bottle was paired with Abbott on-market HIV Combo microparticles and assay specific diluent (Abbott list number 2P36). Assay testing was performed on an Abbott ARCHITECT® automated immunoassay analyzer modified with a two-channel optics configuration. Briefly, a dual photomultiplier tube (PMT) assembly was constructed in which a dichroic mirror with wavelength cutoff of 500 nm was used to reflect low wavelength light (blue) to a vertical PMT while higher wavelength light (green) passed through the mirror to a second PMT. Appropriate filters were placed after the dichroic mirror to additionally filter light prior to reaching the respective PMTs. Hardware on the ARCHITECT® instrument was used to read the output from the reflected (blue) PMT, while a separate counter module and laptop computer interface were used to compile signal from the in-line (green) PMT. A custom IDL code was developed to automatically process the signal from the in-line PMT. Assay testing was performed using the on-market ARCHITECT® HIV Combo assay file which performs a 2-step immunoassay using CMIA technology. Briefly, sample, ARCHITECT® Wash Buffer, assay diluent, and microparticles are combined in the first step. HIV p24 antigen and HIV antibodies present in the sample bind to the HIV antigen and HIV p24 mAb coated microparticles. After washing, the acridinium-labeled conjugates are added and bind to the HIV p24 antigen and HIV antibodies captured on the microparticles. Following another wash cycle, pre-trigger and trigger solutions are added to the reaction mixture to promote the chemiluminescent signal which is measured as relative light units (RLU).

Figure 7:
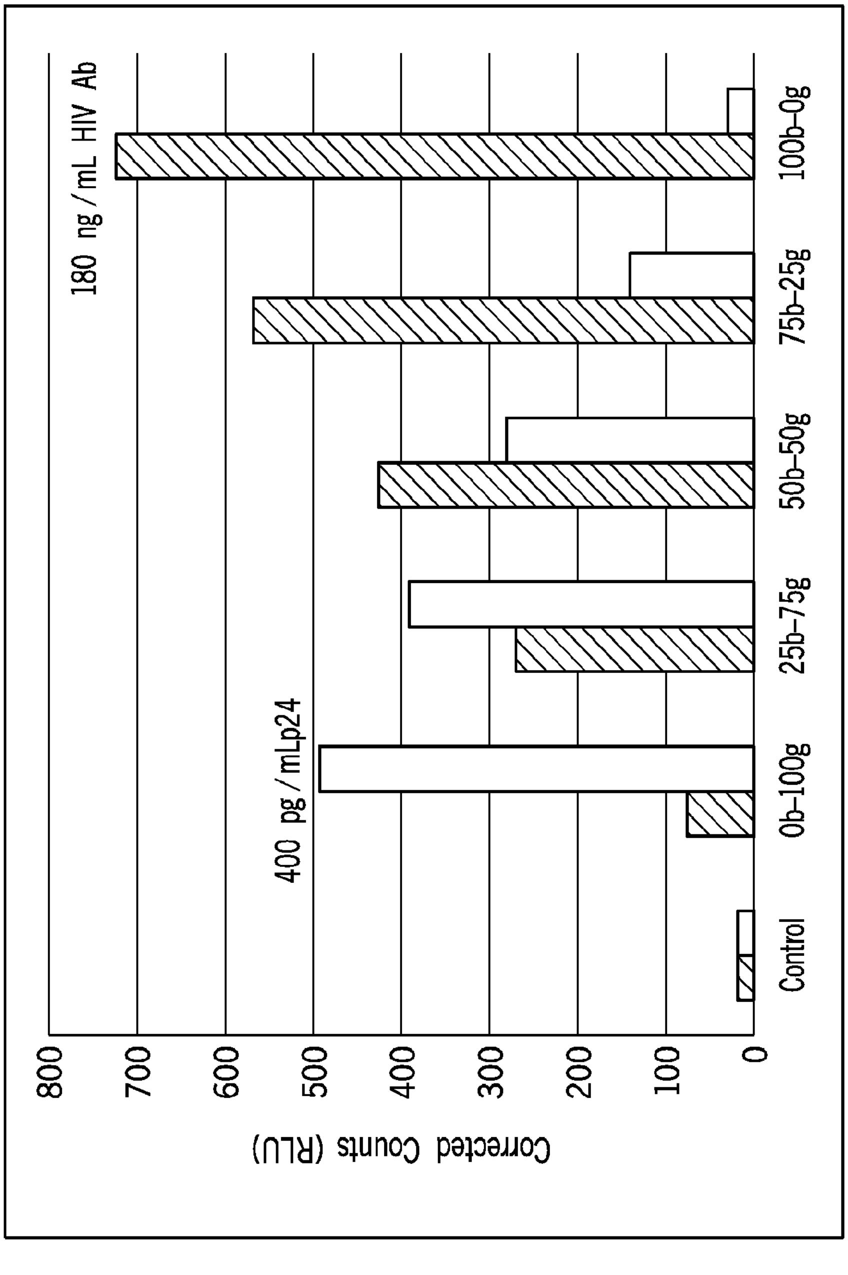
FIG. 7 shows results of an HIV antigen and antibody combination multiplexing assay, as described in Example 79.

A multiplexing test was performed in which normal human plasma was spiked with increasing or decreasing levels of HIV antibody and HIV p24 antigen. Samples were created containing 400, 300, 200, 100, and 0 pg/mL p24 antigen paired with 0, 45, 90, 135, and 180 ng/mL anti-HIV antibody. The samples represent mixture ratios of 0:100, 25:75, 50:50, 75:25, and 100:0 percent normalized sample quantities. Signal produced in both data channels was processed and analyzed. Results, shown in FIG. 7, demonstrated that the assembled reagent kit and two channel PMT setup can differentiate mixed antigen and antibody signals in a single sample.

Example 80

Multiplexing Assay Evaluation—Lyme disease IgG and IgM Assay. Lyme disease IgG and IgM antibody detection kits (total Lyme) were assembled by preparing an anti-human IgG antibody-acridinium-lucifer yellow conjugate solution (25 ng/mL, Example 69) for Lyme IgG antibody detection and an anti-human IgM antibody-acridinium conjugate solution (15 ng/mL) for Lyme IgM antibody detection in Lyme IgG conjugate diluent (containing MES, detergent, and protein stabilizers). The kit was comprised of the experimental conjugates, microparticles coated with recombinant antigens derived from the Variable major protein-like sequence, expressed (VlsE) of *Borrelia burgdorferi*, and an assay specific diluent at pH 7.5. Assay testing was performed on an Abbott ARCHITECT® automated immunoassay analyzer modified with a two-channel optics configuration. Briefly, a dual photomultiplier tube (PMT) assembly was constructed in which a dichroic mirror with wavelength cutoff of 500 nm was used to reflect low wavelength light (blue) to a vertical PMT while higher wavelength light (green) passed through the mirror to a second PMT. Appropriate filters were placed after the dichroic mirror to additionally filter light prior to reaching the respective PMTs. Hardware on the ARCHITECT® instrument was used to read the output from the reflected (blue) PMT, while a separate counter module and laptop computer interface were used to compile signal from the in-line (green) PMT. A custom computer program (IDL code) was developed to automatically process the signal from the in-line PMT. Assay testing was performed using an assay file which performs a 2-step immunoassay using CMIA technology. Briefly, sample, ARCHITECT® Wash Buffer, assay diluent, and microparticles are combined in the first step. Human anti-Lyme IgG and IgM antibodies present in the sample bind to the Lyme antigen coated microparticles. After washing, the anti-human acridinium-labeled conjugates are added and bind to the human antibodies captured on the microparticles. Following another wash cycle, pre-trigger and trigger solutions are added to the reaction mixture to produce the chemiluminescent signal, which is measured as relative luminescence units (RLU).

Figure 8:
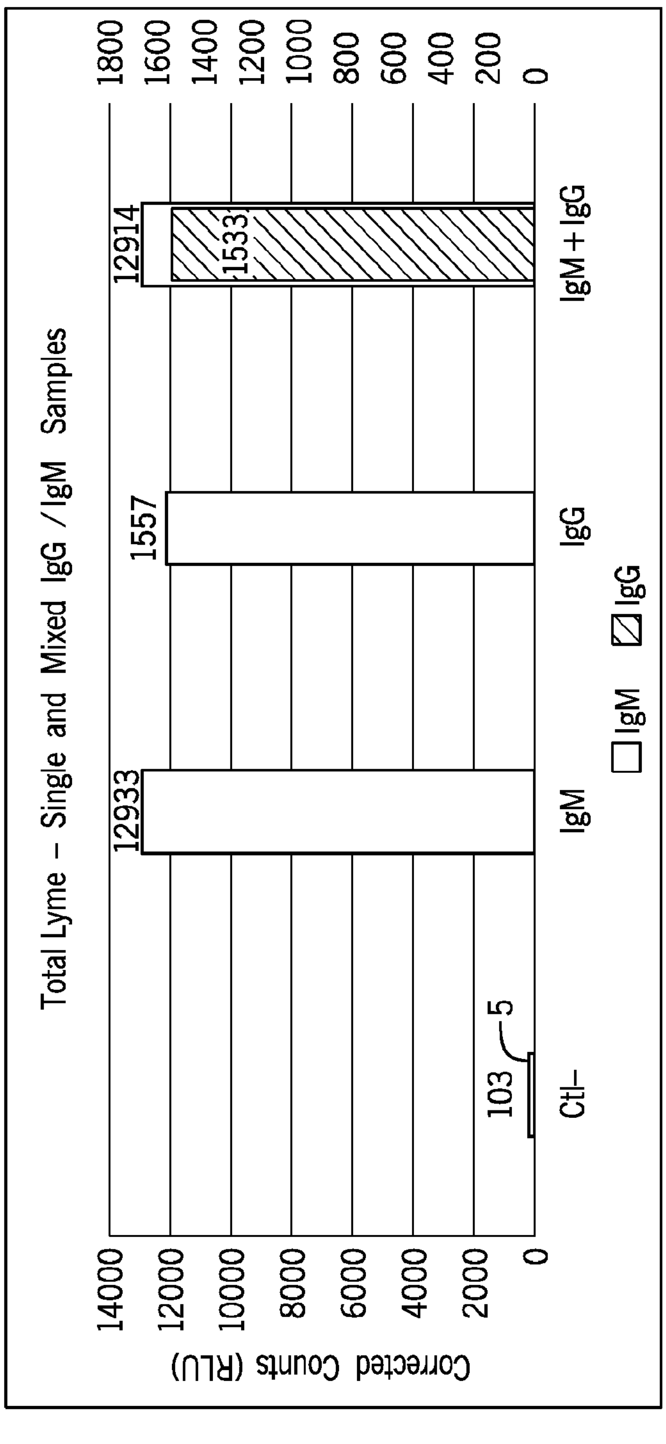
FIG. 8 shows results of shows results of a Lyme disease IgG and IgM multiplexing assay, as described in Example 80.

A multiplexing test was performed in which a Lyme IgG-only sample was combined with a Lyme IgM-only containing sample in a 1:1 ratio and the mixed sample's results were compared to those of single constituent samples. Signal produced in the respective green and blue channels was processed and analyzed. Results, shown in FIG. 8, demonstrated that the assembled reagent kit can differentiate mixed IgM and IgG signals in a single sample.

Example 81

Free T4 and Thyroid Stimulating Hormone Combination Assay—Free T4 and Thyroid Stimulating Hormone (TSH) detection kits (FT4/TSH) were assembled by preparing a T3-Acridinium-Lucifer Yellow conjugate solution (750 ng/mL, Example 64) for T4 detection in ARCHITECT®-free T4 conjugate diluent containing detergent and MES buffer. A microparticle bulk solution was created by combining anti-T4 antibody-coated microparticles with anti-TSH antibody-coated microparticles in ARCHITECT®-free T4 microparticle diluent containing Tris buffer, bovine serum albumin, and detergent. The experimental T4 conjugate and FT4/TSH microparticle bottles were paired with Abbott on-market TSH conjugate (anti-TSH antibody labeled with acridinium) and an assay specific diluent composed of Tris buffer, pH 7.4. Assay testing was performed on an Abbott ARCHITECT® automated immunoassay analyzer modified with a two-channel optics configuration. Briefly, a dual photomultiplier tube (PMT) assembly was constructed in which a dichroic mirror with wavelength cutoff of 500 nm was used to reflect low wavelength light (blue) to a vertical PMT while higher wavelength light (green) passed through the mirror to a second PMT. Appropriate filters were placed after the dichroic mirror to additionally filter light prior to reaching the respective PMTs. Hardware on the ARCHITECT® instrument was used to read the output from the reflected (blue) PMT, while a separate counter module and laptop computer interface were used to compile signal from the in-line (green) PMT. A custom computer program (IDL code) was developed to automatically process the signal from the in-line PMT. Assay testing was performed using CMIA technology and a 4-bottle assay file which adds conjugate reagents at different steps creating a 1-step immunoassay and a 2-step immunoassay sequentially. Briefly, sample, ARCHITECT® Wash Buffer, assay diluent, microparticles, and experimental T4 conjugate are combined in the first step. The T4 in the sample competes with the T3 acridinium-lucifer yellow conjugate for binding to the anti-T4 microparticles, and TSH in the sample binds to the anti-TSH coated microparticles. After washing, the acridinium-labeled anti-TSH antibody conjugate is added and binds to the TSH captured on the microparticles. Following another wash cycle, pre-trigger and trigger solutions are added to the reaction mixture to promote the chemiluminescent signal, which is measured as relative luminescence units (RLU).

Figure 9:
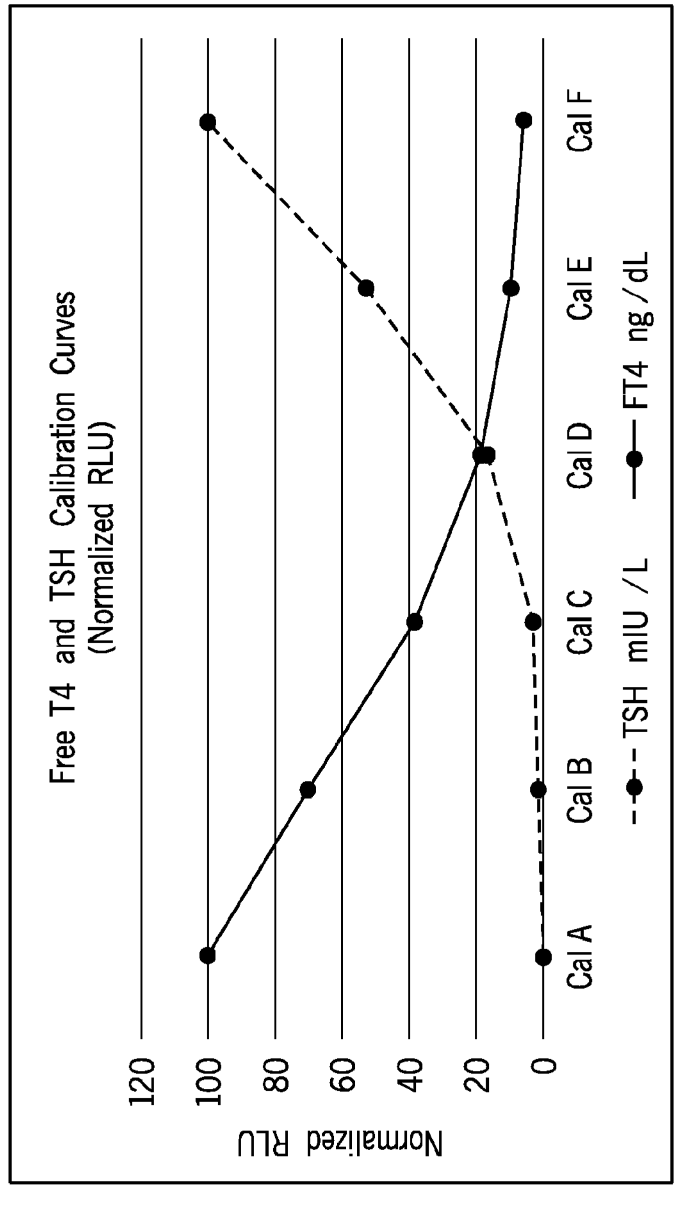
FIG. 9 shows results of a free T4 and thyroid stimulating hormone combination multiplexing assay, as described in Example 81.

Assay performance was measured by calibration curve shape and the ability to read single constituent controls for Free T4 and TSH. (FT4 calibrator levels used were 0, 0.5, 1, 2, 3.5, and 6 ng/dL. TSH calibrator levels used were 0, 0.5, 2, 10, 40, and 100 mIU/L.) Signal produced in both data channels was processed and analyzed. Results, shown in FIG. 9 and Table 2, demonstrated that the assembled reagent kit and two channel PMT setup can calibrate and read Free T4 and TSH controls within standard specification limits.

TABLE 2

Free T4 and TSH Single Constituent Controls (including Specification Limits)

| TSH | mIU/L | Target | LSL | USL |
|---|---|---|---|---|
| Low | 0.11 | 0.1 | 0.065 | 0.135 |
| Medium | 6.17 | 6 | 3.9 | 8.1 |
| High | 30.45 | 30 | 19.5 | 40.5 |
| **Free T4** | **ng/dL** | **Target** | **LSL** | **USL** |
| Low | 0.66 | 0.65 | 0.42 | 0.85 |
| Medium | 1.09 | 1.2 | 0.86 | 1.62 |
| High | 2.21 | 2.8 | 1.82 | 3.78 |

The invention claimed is:

1. A compound of formula (I), or a salt thereof:

(I)

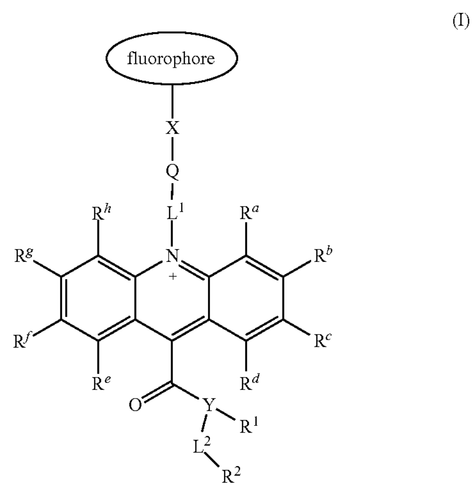

wherein: X is ethylenediamine, 4,7,10-trioxa-1,13-tridecanediamine,

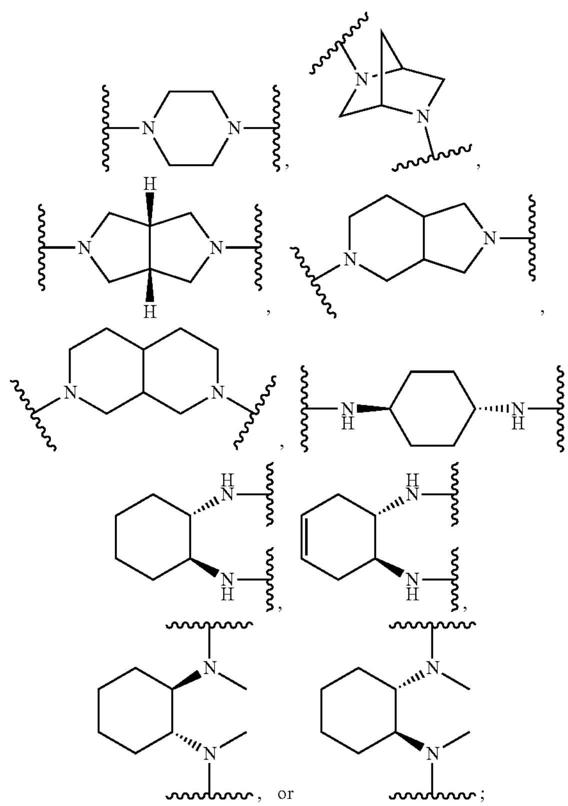

, , , , , , , or ;

Y is nitrogen, oxygen, or sulfur, wherein when Y is nitrogen, R' is —$SO_2$-A, wherein A is phenyl that is unsubstituted or substituted with 1 or 2 substituents from $C_1$-$C_4$ alkyl, and when Y is oxygen or sulfur, R' is absent;

Q is —$SO_2$— or —CO—;

$L^1$ and $L^2$ are each independently a $C_1$-$C_4$ alkylene;

$R^2$ is —COOZ;

Z is hydrogen or $C_1$-$C_4$ alkyl; and $R^a$, $R^b$, $R^c$, $R^d$, $R^e$, $R^f$, $R^g$, and $R^h$ are each hydrogen.

2. The compound of claim 1, or a salt thereof, wherein X is

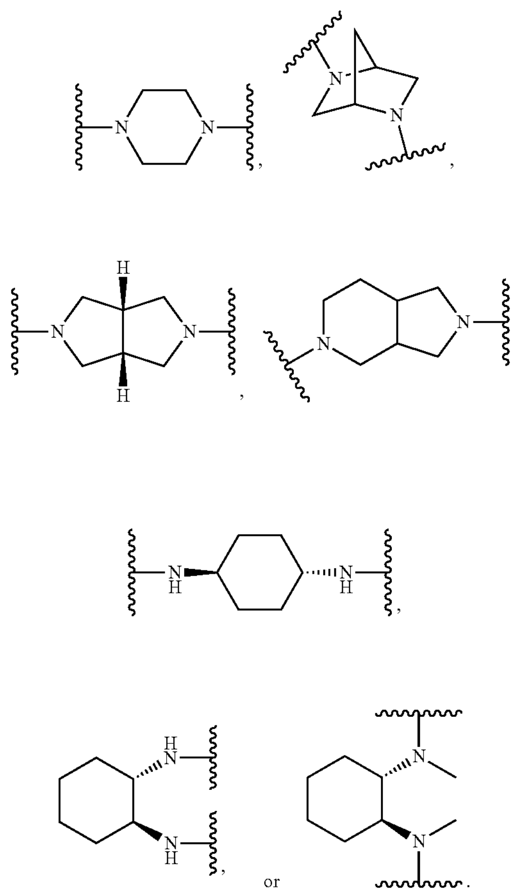

3. The compound of claim 1, or a salt thereof, wherein X is:

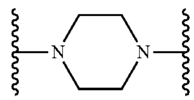

4. The compound of claim 1, or a salt thereof, wherein Y is nitrogen.

5. The compound of claim 4, or a salt thereof, wherein A is phenyl that is substituted with 1 substituent from $C_1$-$C_4$ alkyl.

6. The compound of claim 1, or a salt thereof, wherein Q is $-SO_2-$.

7. The compound of claim 1, or a salt thereof, wherein Z is hydrogen.

8. The compound of claim 1, or a salt thereof, wherein $L^1$ is $-CH_2CH_2CH_2-$, $L^2$ is $-CH_2CH_2CH_2-$, or both $L^1$ and $L^2$ are $-CH_2CH_2CH_2-$.

9. The compound of claim 1, or a salt thereof, wherein the compound has formula (Ia):

(Ia)

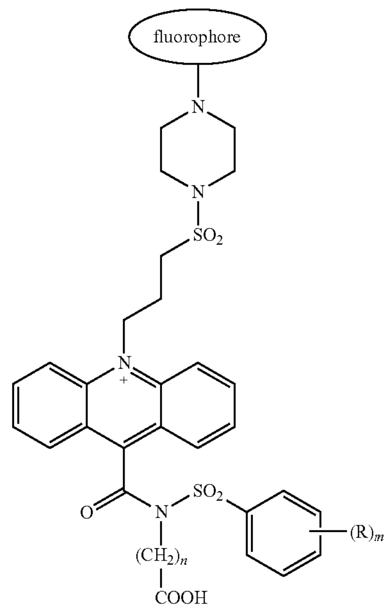

wherein:

each R is independently selected from the group consisting of $C_1$-$C_4$ alkyl;

m is 0, 1, or 2; and n is 2, 3, or 4.

10. The compound of claim 9, or a salt thereof, wherein m is 1 and R is $C_1$-$C_4$ alkyl.

11. The compound of claim 9, or a salt thereof, wherein m is 1 and R is methyl.

12. The compound of claim 9, or a salt thereof, wherein n is 3.

13. The compound of claim 9, or a salt thereof, wherein the compound has formula (Ib):

(Ib)

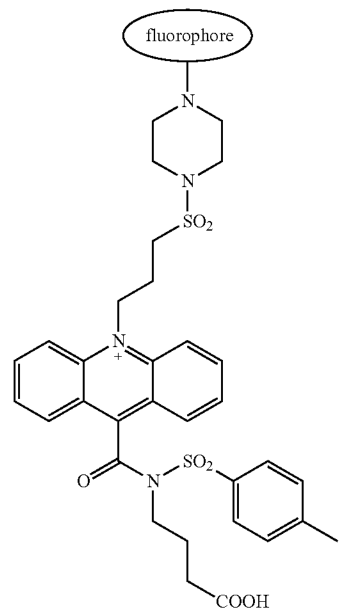

14. The compound of claim 1, or a salt thereof, wherein the fluorophore is a fluorescein, a rhodamine, a boron-dipyrromethene, a cyanine, an oxazine, a thiazine, a coumarin, a naphthalimide, a rhodol, a naphthalene, a squaraine, a porphyrin, a flavin, or a lanthanide-based dye.
15. The compound of claim 1, or a salt thereof, wherein the fluorophore is
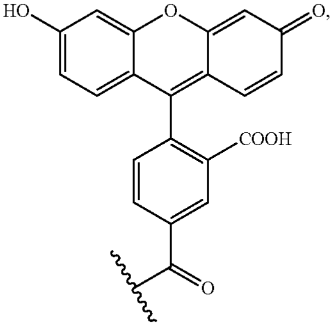
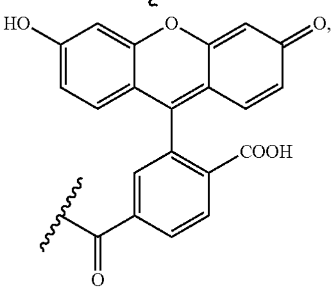
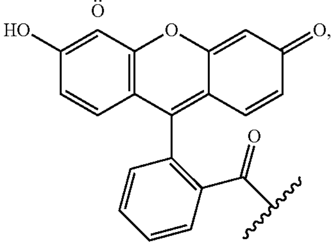
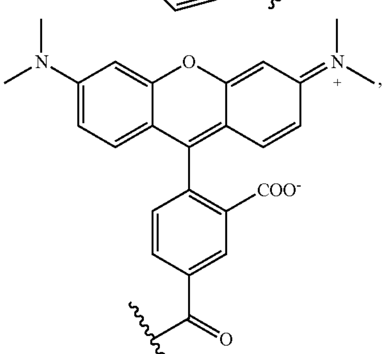
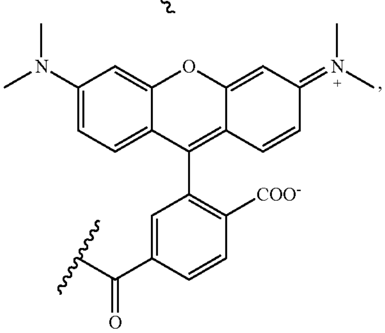
-continued
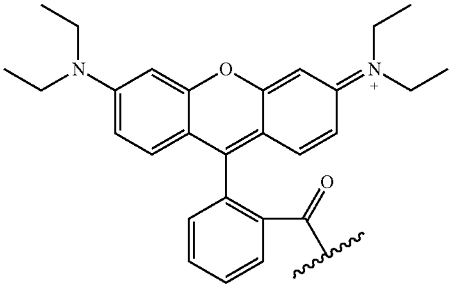
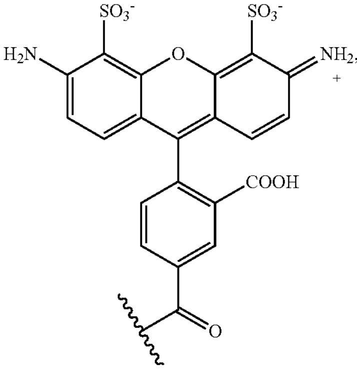
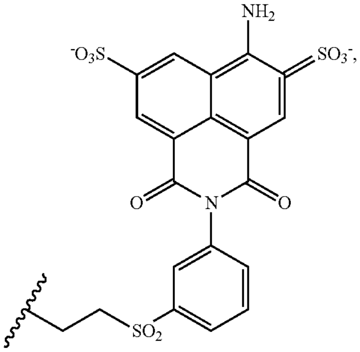
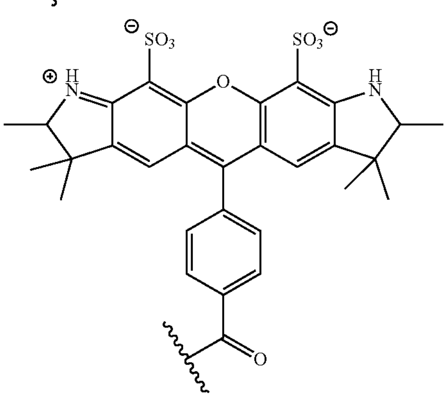
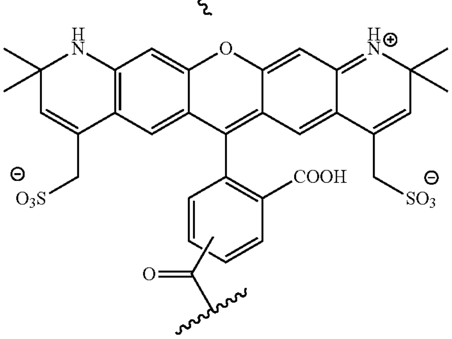

-continued
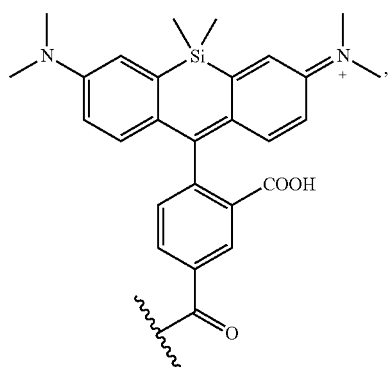
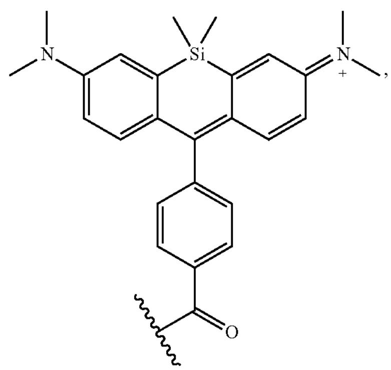
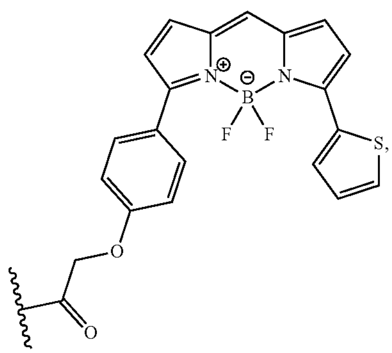
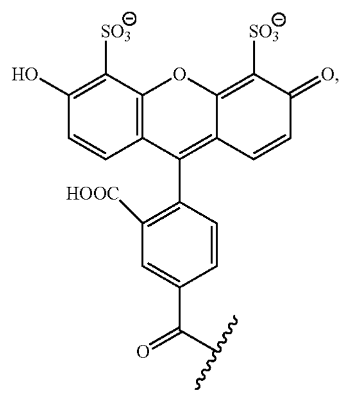
-continued
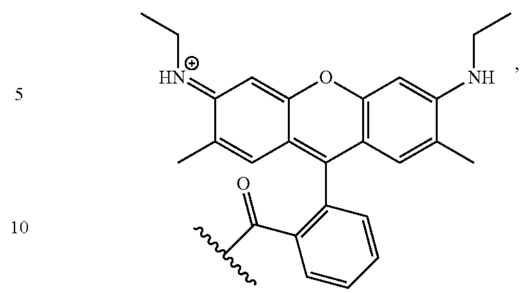
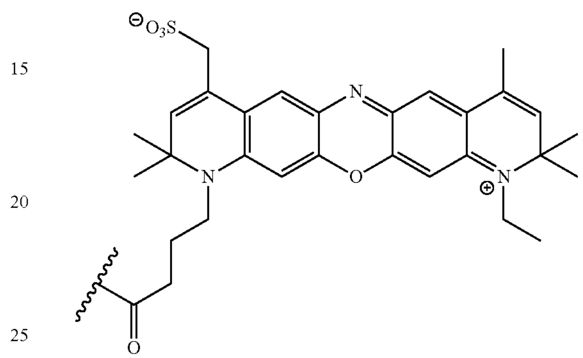
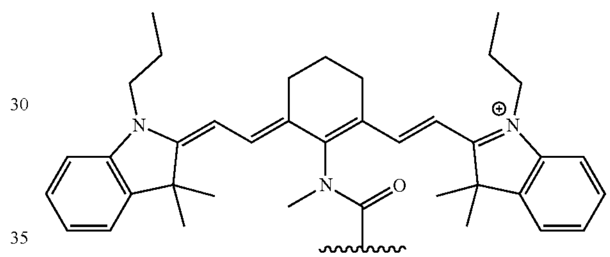
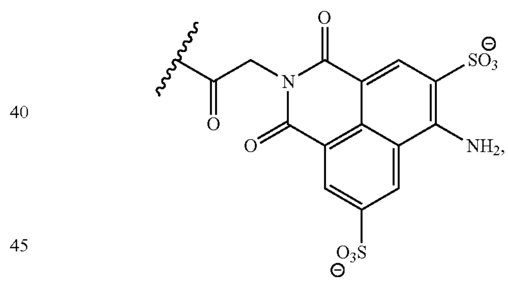
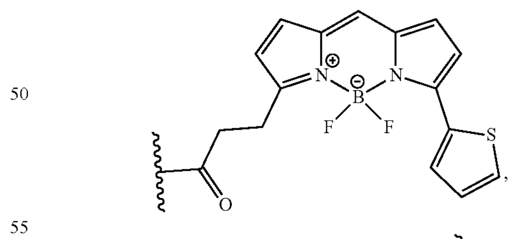
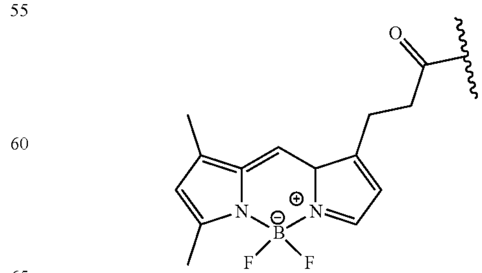

-continued

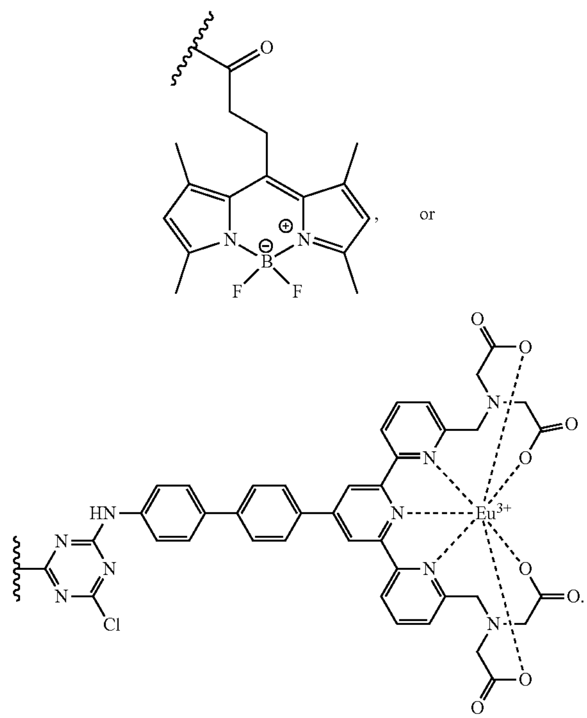

or

16. A conjugate of formula (II), or a salt thereof:

(II)

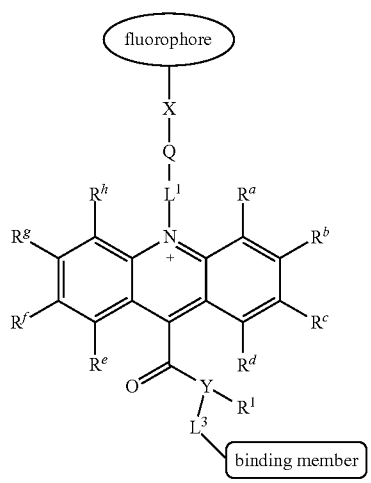

wherein: X is ethylenediamine, 4,7,10-trioxa-1,13-tridecanediamine,

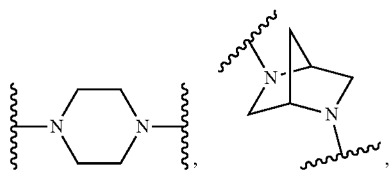

-continued

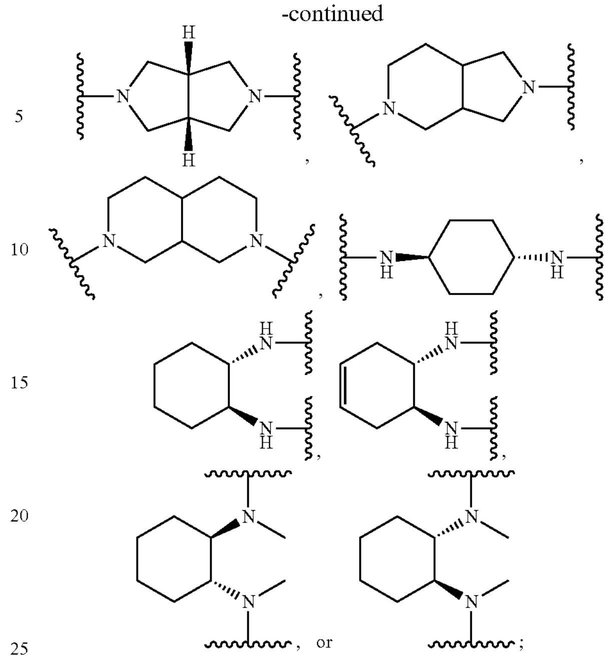

or

Y is nitrogen, oxygen or sulfur, wherein when Y is nitrogen, R' is —$SO_2$-A, wherein A is phenyl that is unsubstituted or substituted with 1 or 2 substituents from $C_1$-$C_4$ alkyl, and when Y is oxygen or sulfur, R' is absent;

Q is —$SO_2$— or —CO—;

L' is a $C_1$-$C_4$ alkylene;

$L^3$ is a $C_1$-$C_4$ alkylene linker;

$R^a$, $R^b$, $R^c$, $R^d$, $R^e$, $R^f$, $R^g$, and $R^h$ are each hydrogen; and the binding member is a molecule capable of binding to a target analyte.

17. A method of detecting an analyte of interest in a biological sample, the method comprising the steps of:

a) contacting a biological sample with at least one specific binding member that binds to an analyte of interest to form at least one complex, wherein the specific binding member comprises the conjugate of claim 16, or a salt thereof; and b) detecting the presence or absence of a signal from the specific binding member, wherein detection of the signal indicates that the analyte is present in the sample and the absence of the signal indicates that the analyte is not present in the sample.

18. A method of detecting two or more analytes of interest in a biological sample, the method comprising the steps of:

a) contacting the biological sample either simultaneously or sequentially with (i) at least one first specific binding member that binds to a first analyte of interest to form at least one first complex; and (ii) at least one second specific binding member that binds to a second analyte of interest to form at least one second complex, wherein each of the first and second specific binding members comprise the conjugate of claim 16, or a salt thereof, and wherein the fluorophore of the conjugate in each of the first and second specific binding members is different; and b) detecting the presence or absence of a signal from each of the first and second specific binding members, wherein (i) detection of a signal from the first specific binding member indicates that the first analyte is present in the sample and the absence of a signal from the first specific binding member indicates that the first analyte is not present in the sample; and (ii) detection of a signal from the second specific binding member indicates that the second analyte is present in the sample and the absence of a signal from the second specific binding member indicates that the second analyte is not present in the sample.

19. A method of detecting two or more analytes of interest in a biological sample, the method comprising the steps of:

a) contacting the biological sample with at least one first specific binding member and at least one second specific binding member, wherein the at least one first specific binding member and the at least one second specific binding member each specifically bind to a first analyte of interest thereby producing one or more first complexes comprising the first specific binding member-first analyte-second specific binding member, wherein the second specific binding member comprises the conjugate of claim 16, or a salt thereof; and b) contacting the biological sample either simultaneously or sequentially with at least one third specific binding member and at least one fourth specific binding member, wherein the at least one third specific binding member and the at least one fourth specific binding member each specifically bind to a second analyte of interest, thereby producing one or more second complexes comprising the third specific binding member-second analyte-fourth specific binding member, wherein the fourth specific binding member comprises the conjugate of claim 18, and wherein the fluorophore in the conjugate in each of the second and fourth specific binding members is different; and c) detecting the presence or absence of a signal from each of the second and fourth specific binding members, wherein (i) detection of a signal from the second specific binding member indicates that the first analyte is present in the sample and the absence of a signal from the second specific binding member indicates that the first analyte is not present in the sample and further; and (ii) detection of a signal from the fourth specific binding member indicates that the second analyte is present in the sample and the absence of a signal from the fourth specific binding member indicates that the second analyte is not present in the sample.

* * * * *